(12) United States Patent
Fass et al.

(10) Patent No.: US 10,829,561 B2
(45) Date of Patent: Nov. 10, 2020

(54) ANTIBODIES TARGETING QUIESCIN SULFHYDRYL OXIDASE (QSOX1) AND USES OF SAME

(71) Applicant: Yeda Research and Development Co. Ltd., Rehovot (IL)

(72) Inventors: Deborah Fass, Rehovot (IL); Iris Grossman, Rehovot (IL); Tal Ilani, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 180 days.

(21) Appl. No.: 15/961,928

(22) Filed: Apr. 25, 2018

(65) Prior Publication Data

US 2018/0273639 A1    Sep. 27, 2018

Related U.S. Application Data

(63) Continuation of application No. PCT/IL2016/051147, filed on Oct. 25, 2016.

(60) Provisional application No. 62/246,076, filed on Oct. 25, 2015.

(51) Int. Cl.
| C07K 16/40 | (2006.01) |
| A61K 39/395 | (2006.01) |
| C07K 16/18 | (2006.01) |
| A61K 39/00 | (2006.01) |
| A61P 35/00 | (2006.01) |

(52) U.S. Cl.
CPC .......... *C07K 16/40* (2013.01); *A61K 39/395* (2013.01); *C07K 16/18* (2013.01); *A01K 2227/105* (2013.01); *A01K 2267/0306* (2013.01); *A61K 2039/505* (2013.01); *A61P 35/00* (2018.01); *C07K 2317/33* (2013.01); *C07K 2317/565* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2014/0141015 A1 | 5/2014 | Lake et al. |
| 2015/0110786 A1 | 4/2015 | Fass et al. |
| 2017/0247468 A1 | 8/2017 | Fass et al. |
| 2018/0185477 A1 | 7/2018 | Lake et al. |

FOREIGN PATENT DOCUMENTS

| CN | 101503679 | 8/2009 |
| WO | WO 02/06315 | 1/2002 |
| WO | WO 2010/071787 | 6/2010 |
| WO | WO 2010/077921 | 7/2010 |
| WO | WO 2012/040095 | 3/2012 |
| WO | WO 2013/132495 | 9/2013 |
| WO | WO2013132495 | * 9/2013 |
| WO | WO2013132495 | * 4/2015 |
| WO | WO 2017/072757 | 5/2017 |
| WO | WO 2020/035863 | 2/2020 |

OTHER PUBLICATIONS

Tiller et al. "Efficient Generation of Monoclonal Antibodies From Single Human B Cells by Single Cell RT-PCR and Expression Vector Cloning", Journal of Immunological Methods, 329(1-2): 112-124, Available Online Oct. 31, 2007.
Communication Pursuant to Article 94(3) EPC dated Oct. 16, 2015 From the European Patent Office Re. Application No. 13716846.4.
Communication Pursuant to Article 94(3) EPC dated May 19, 2017 From the European Patent Office Re. Application No. 13716846.4. (8 Pages).
Communication Pursuant to Article 94(3) EPC dated Aug. 29, 2016 From the European Patent Office Re. Application No. 13716846.4.
Decision on Rejection dated Dec. 4, 2017 From the State Intellectual Property Office of the People's Republic of China Re. Application No. 201380024279.0 and Its Translation Into English. (14 Pages).
International Preliminary Report on Patentability dated Sep. 18, 2014 From the International Bureau of WIPO Re. Application No. PCT/IL2013/050209.
International Search Report and the Written Opinion dated Jun. 5, 2013 From the International Searching Authority Re. Application No. PCT/IL2013/050209.
Office Action and Search Report dated Nov. 2, 2016 From the State Intellectual Property Office of the People's Republic of China Re. Application No. 201380024279.0 and Its Translation Into English. (28 Pages).
Office Action and Search Report dated Mar. 4, 2016 From the State Intellectual Property Office of the People's Republic of China Re. Application No. 201380024279.0 and Its Translation Into English.
Office Action dated Mar. 1, 2018 From the Israel Patent Office Re. Application No. 234483. (3 Pages).
Office Action dated Apr. 17, 2016 From the Israel Patent Office Re. Application No. 234483.
Office Action dated May 27, 2017 From the State Intellectual Property Office of the People's Republic of China Re. Application No. 201380024279.0 and Its Translation Into English. (25 Pages).
Restriction Official Action dated Aug. 18, 2016 From the US Patent and Trademark Office Re. U.S. Appl. No. 14/383,571.
Amiot et al. "Expression of the Secreted FAD-Dependent Sulfydryl Oxidase (QSOX) in the Guinea Pig Central Nervous System", Molecular Brain Research, 125: 13-21, 2004.
Antwi et al. "Analysis of the Plasma Peptidome From Pancreas Cancer Patients Connects a Peptide in Plasma to Overexpression of the Parent Protein in Tumors", Journal of Proteome Research, 8: 4722-4731, 2009.

(Continued)

*Primary Examiner* — Lei Yao

(57) ABSTRACT

An antibody comprising an antigen recognition domain exhibiting species cross reactivity to human QSOX1 and murine QSOX1 is disclosed. Methods of producing the antibody, pharmaceutical compositions comprising the antibody and methods of using the antibody for treating medical conditions are also disclosed.

4 Claims, 14 Drawing Sheets
(9 of 14 Drawing Sheet(s) Filed in Color)
Specification includes a Sequence Listing.

(56) References Cited

OTHER PUBLICATIONS

Coppock et al. "Preferential Gene Expression in Quiescent Human Lung Fibroblasts", Cell Growth & Differentiation, 4: 483-493, Jun. 1993.
Coppock et al. "Regulation of the Quiescence-Induced Genes: Quiescin Q6, Decorin, and Ribosomal Protein S29", Biochemical and Biophysical Research Communications, 269: 604-610, 2000.
Janolino et al. "Isolation and Characterization of Sulfhydryl Oxidase From Bovine Milk", The Journal of Biological Chemistry, 250(7): 2532-2538, Apr. 10, 1975.
Katchman et al. "Quiescin Sulfhydryl Oxidase 1 Promotes Invasion of Pancreatic Tumor Cells Mediated by Matrix Metalloproteinases", Molecular Cancer Research, XP002697583, 9(12): 1621-1631, Oct. 11, 2011. p. 1626, Para 'Role of QSOX1 in Tumour Cell Invasion', p. 1626, Right Col., Para 1, p. 1628, Left Col., Para 5.
Lake et al. (Geltosky) "QSOX1 as an Anti-Neoplastic Drug Target. AzTE Case #M11-003", AzTE Arizona Technology Enterprises, Arizona State University, XP055011559, 1 P., Aug. 30, 2011.
Musard et al. "Identification and Expression of a New Sulfhydryl Oxidase SOx-3 During the Cell Cycle and the Estrus Cycle in Uterine Cells", Biochemical and Biophysical Research Communications, 287: 83-91, 2001.
Ouyang et al. "Loss-of-Function of Nkx3.1 Promotes Increased Oxidative Damage in Prostate Carcinogenesis", Cancer Research, 65: 6773-6779, Aug. 1, 2005.
Portes et al. "Tissue Distribution of Quiescin Q6/Sulfhydryl Oxidase (QSOX) in Developing Mouse", Journal of Molecular Histology, 39: 217-225, 2008.
Song et al. "Loss of Nkx3.1 Leads to the Activation of Discrete Downstream Target Genes During Prostate Tumorigenesis", Oncogene, 28: 3307-3319, Jul. 13, 2009.
Tang "Research Progress in Relations Between MMP-2, MMP-9 and Lung Cancer and Pulmonary Fibrosis", The Practical Journal of Cancer, 24(1): 91-92, Jan. 31, 2009. & English Machine Translation. p. 92, Left Col., Para 1-4.
Tury et al. "Cell-Specific Localization of the Sulphydryl Oxidase QSOX in Rat Peripheral Tissues", Cell and Tissue Research, 323: 91-103, 2006.
Official Action dated Nov. 27, 2018 From the US Patent and Trademark Office Re. U.S. Appl. No. 15/494,585. (30 Pages).
International Search Report and the Written Opinion dated Feb. 2, 2017 From the International Searching Authority Re. Application No. PCT/IL2016/051147.
Alon et al. "Abdesign: Computational Antibody Design Switching Species Preference and Humanizing an Inhibitory Antibody", Protein Science, XP002765920, Poster Abstracts, 23(Suppl.1): 153-154, # POST 12-208, Jul. 1, 2014.
Grossman et al. "An Inhibitory Antibody Blocks the First Step in the Dithiol/Disulfide Relay Mechanism of the Enzyme QSOX1", Journal of Molecular Biology, XP028751684, 425(22): 4366-4378, Jul. 15, 2013. p. 4373.
Grossman et al. "Overcoming a Species-Specificity Barrier in Development of an Inhibitory Antibody Targeting a Modulator of Tumor Stroma", Protein Engineering, Design and Selection, XP055334671, 29(4): 135-147, Advance Access Publication Jan. 26, 2016.
Ilani et al. "A Secreted Disulfide Catalyst Controls Extracellular Matrix Composition and Function", Science, XP055334665, 341(6141): 74-76, Jul. 5, 2013.
ThermoFisher Scientific "QSOX1 Polyclonal Antibosy", ThermoFisher Scientific, XP055334878, Catalog 2013, No. PA5-38009, 2 P., Jan. 2013.
Office Action dated Apr. 8, 2019 From the Israel Patent Office Re. Application No. 261156. (7 Pages).
International Preliminary Report on Patentability dated May 11, 2018 From the International Bureau of WIPO Re. Application No. PCT/IL2016/051147. (10 Pages).
European Search Report and the European Search Opinion dated Apr. 8, 2019 From the European Patent Office Re. Application No. 18181426.0. (9 Pages).
Hecht "IPF Vs. COPD: Learn the Difference", HealthLine, XP055571686, Newsletter, Mar. 15, 2018.
Horan et al. "Partial Inhibition of Integrin AlphaVBeta6 Prevents Pulmonary Fibrosis Without Exacerbating Inflammation", American Journal of Respiratory and Critical Care Medicine, XP002725452, 177(1): 56-65. Published Online Oct. 4, 2007.
Jester et al. "Inhibition of Corneal Fibrosis by Topical Application of Blocking Antibodies to TGF Beta in the Rabbit", Cornea, XP055571610, 16(2): 177-187, Mar. 1997.
International Search Report and the Written Opinion dated Dec. 9, 2019 From the International Searching Authority Re. Application No. PCT/IL2019/050914. (14 Pages).
Requisition by the Examiner dated Dec. 19, 2019 From the Innovation, Science and Economic Development Canada, Canadian Intellectual Property Office Re. Application No. 2,865,486. (4 Pages).
Forsyth et al. "Deep Mutational Scanning of an Antibody Against Epidermal Growth Factor Receptor Using Mammalian Cell Display and Massively Parallel Pyrosequencing", mAbs, XP055645859, 5(4): 523-532, Published Online May 29, 2013.
Koenig et al. "Mutational Landscape of Antibody Variable Domains Reveals a Switch Modulating the Interdomain Conformational Dynamics and Antigen Binding", Proc. Natl. Acad. Sci. USA, PNAS, XP055578865, 114(4): E486-E495, Published Online Jan. 5, 2017.
Official Action dated May 1, 2019 From the US Patent and Trademark Office Re. U.S. Appl. No. 15/494,585. (14 pages).

* cited by examiner

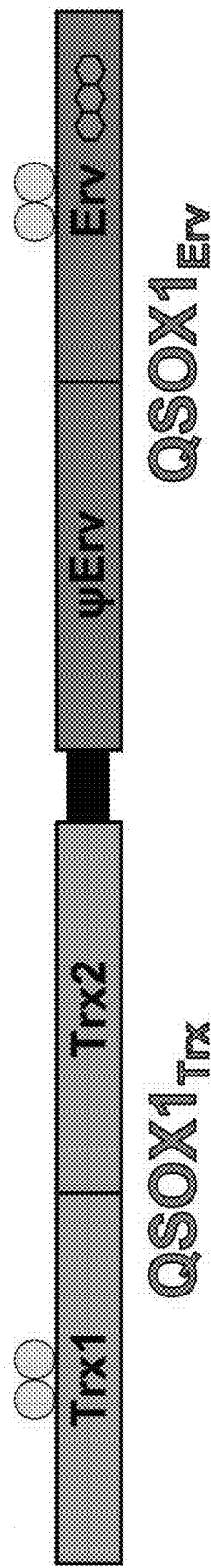
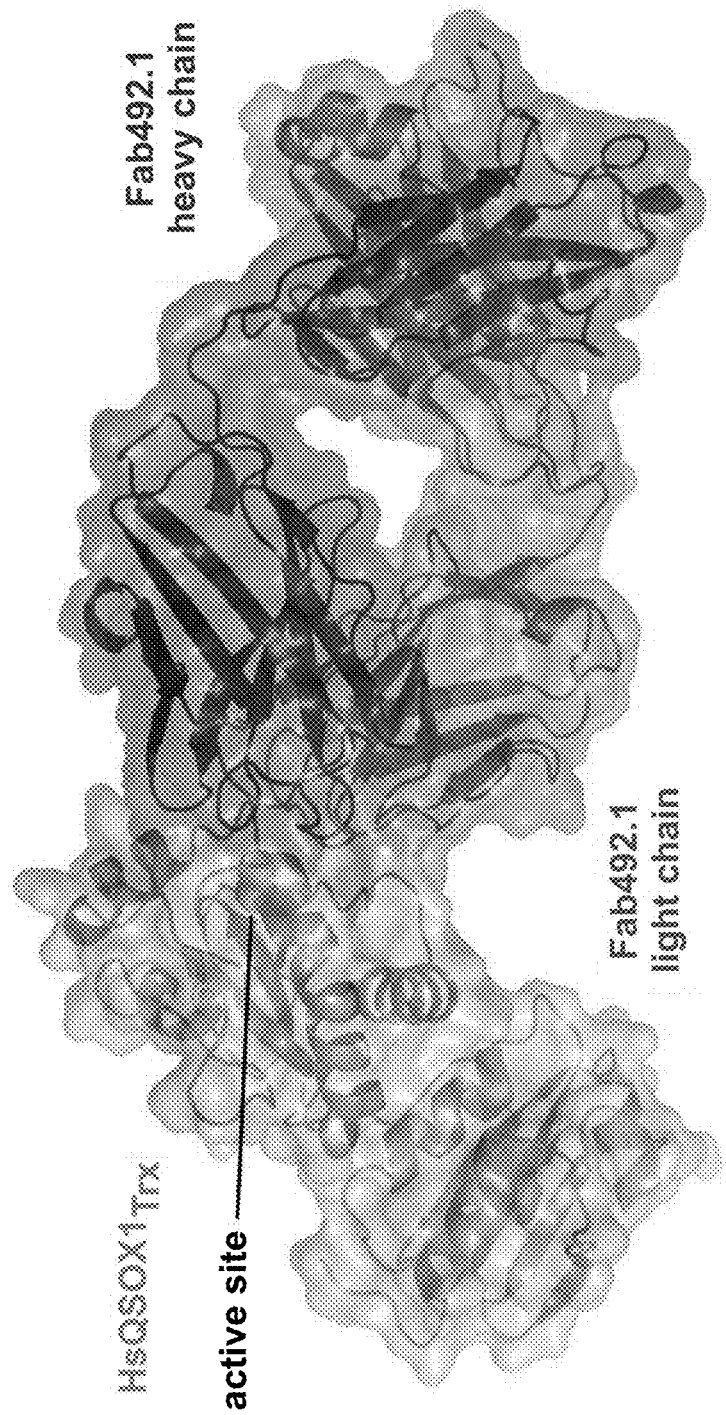
FIG. 1A
FIG. 1B

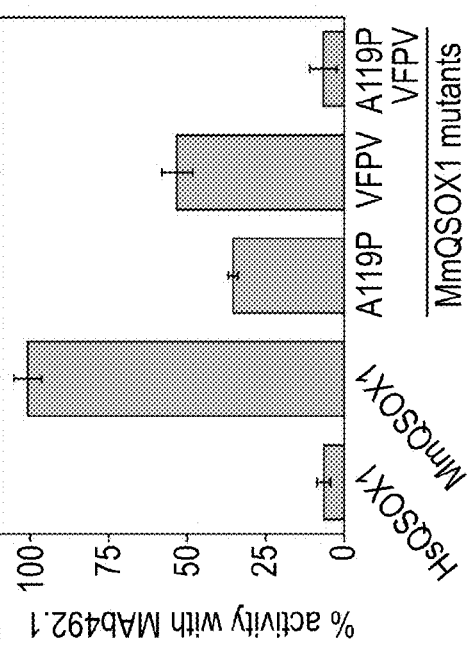
FIG. 2A
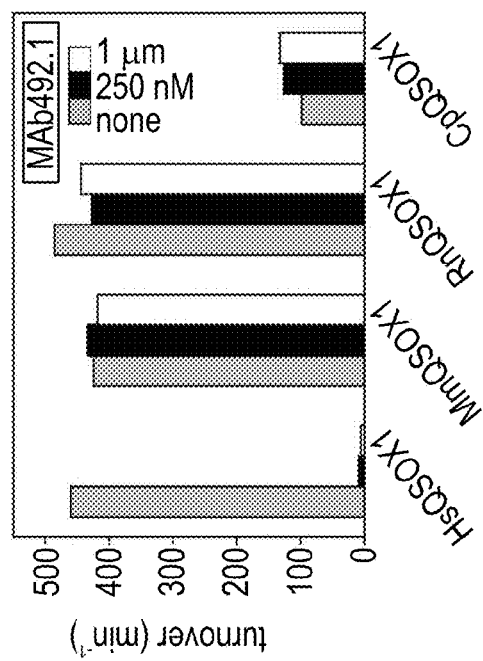
FIG. 2D
| | | | |
|---|---|---|---|
| SEQ ID NO. 5 | HsQSOX1 | 69 | WCGHCIAFAPT 79..106 NSAVCRDFNIPGFPTVRFFKAFTKNGSGAVFPVAGA 141 |
| SEQ ID NO. 6 | MmQSOX1 | 72 | WCGHCIAFAPT 82..109 NSAVCREFNIAGFPTVRFFQAFTKNGSGATLPGAGA 144 |
| SEQ ID NO. 7 | RnQSOX1 | 72 | WCGHCIAFAPT 82..109 NSAVCREFNIAGFPTVRFFKAFSKNGTGTALPAAGA 144 |
| SEQ ID NO. 8 | CpQSOX1 | 70 | WCGHCIAFAPT 80..107 NNAVCRDFNIAGFPSVRFFKAFSKNSTGTTLPVAGA 142 |
FIG. 2B
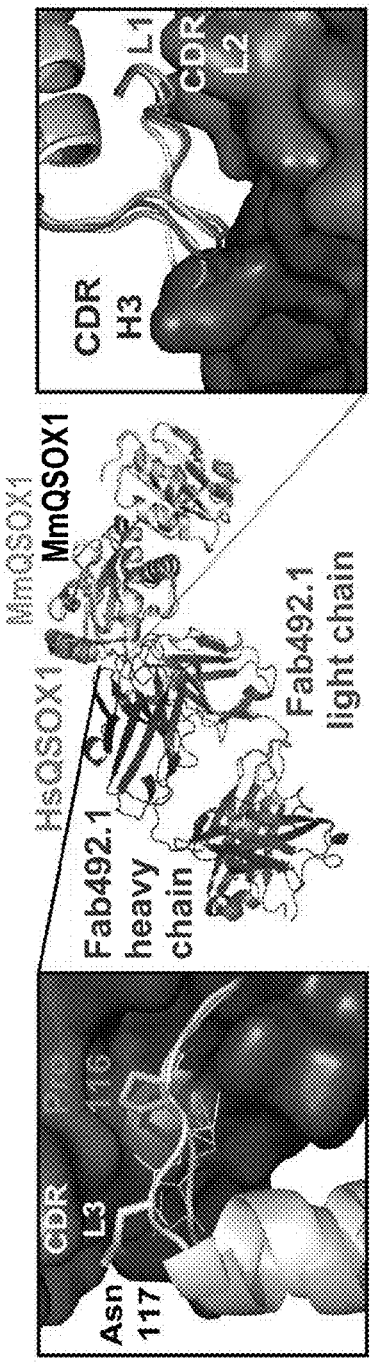
FIG. 2C

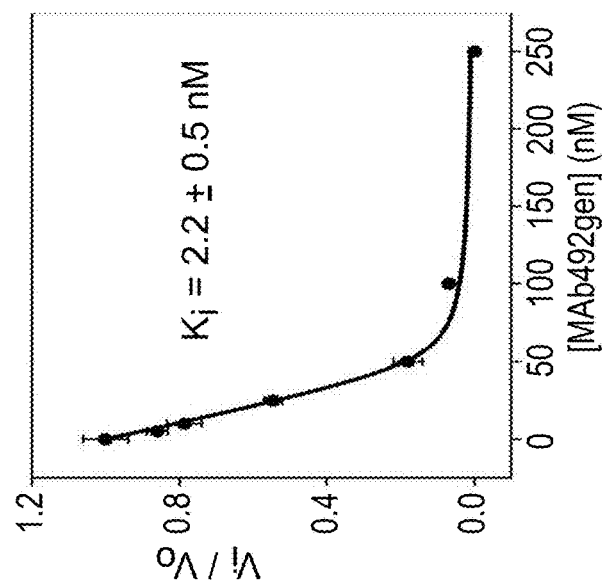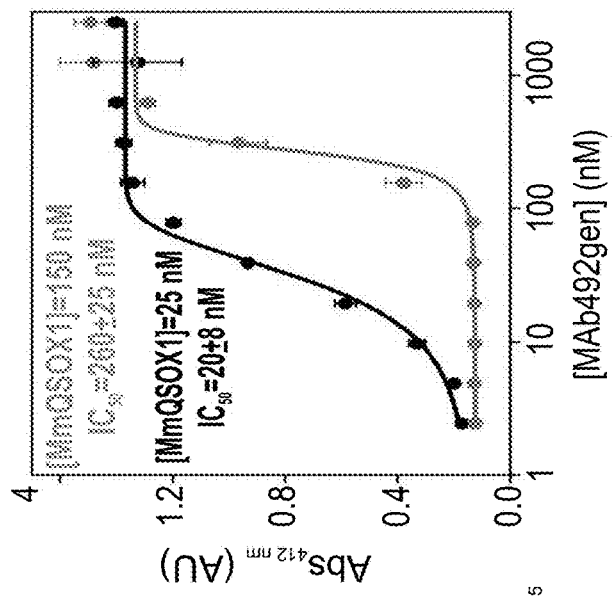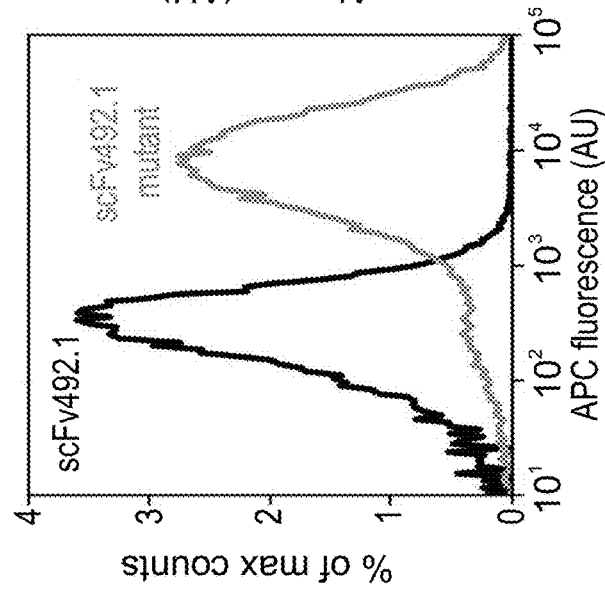

250 nM MAb492.1

No treatment 250 nM MAb316.1

250 nM MAb492gen $K_i = 16 \pm 2$ nM

FIG. 3J

Heavy chain variable region 492.1 Heavy chain SEQ ID NO: 37
492gen Heavy chain SEQ ID NO: 45

```
492gen    1  QVQLKQSGPGLVAPSQSLSITCTVSGFSLTGYGVIWWRQSPGKGLEWLGMIWGDGRTEY   59
492.1     1  QVQLKQSGPGLVAPSQSLSITCTVSGFSLTGYGVNWWRQSPGKGLEWLGMIWGDGRTDY   59

492gen   60  KSALKSRLSITKDNSKSQVFLKMNSLQTDDTARYFCASDWDFGSFAYWGQGTLVTVSA  118
492.1    60  KSALKSRLSITKDNSKSQVFLKMNSLQTDDTARYFCASDYYGSSFAYWGQGTLVTVSA  118
```

Light chain variable region 492.1 Light chain SEQ ID NO: 36
492gen Light chain SEQ ID NO: 44

```
492gen    1  DVVMTQTHKFMSTSVGDRVSITCKASQDVSGAVAWYQQKSGQSPKLLISWASQRYTGVP   59
492.1     1  DVVMTQTHKFMSTSVGDRVSITCKASQDVSTAVAWYQQKSGQSPKLLIHSASYRYTGVP   59

492gen   60  DRFTGSGSGTDFTFTISSVQAEDLAVYYCQQHYAIPLTFGAGTKLELK  107
492.1    60  DRFTGSGSGTDFTFTISSVQAEDLAVYYCQQHYSIPLTFGAGTKLELK  107
```

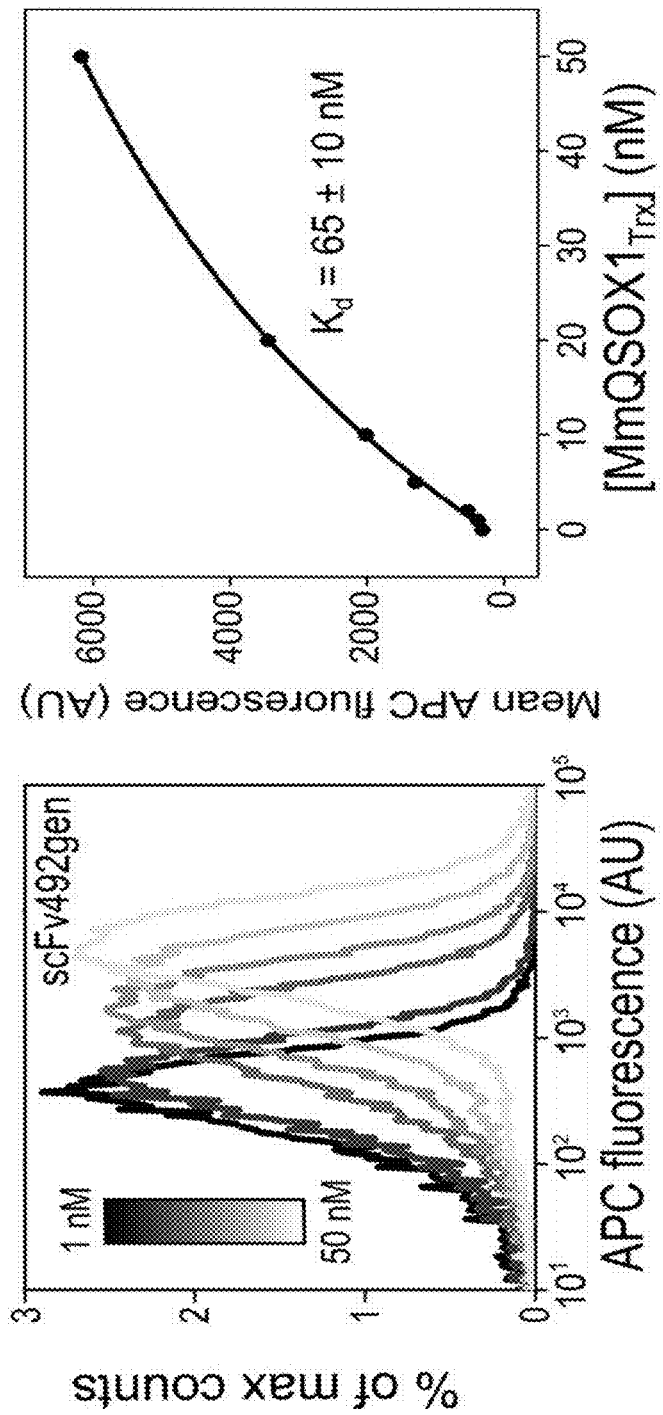

FIG. 4H MAb492.1

FIG. 4F MAb316.1

FIG. 4D MAb492gen

FIG. 4B no treatment

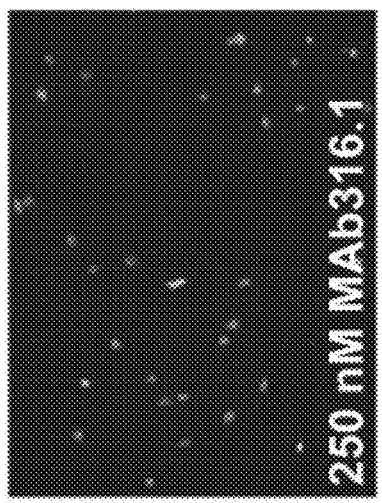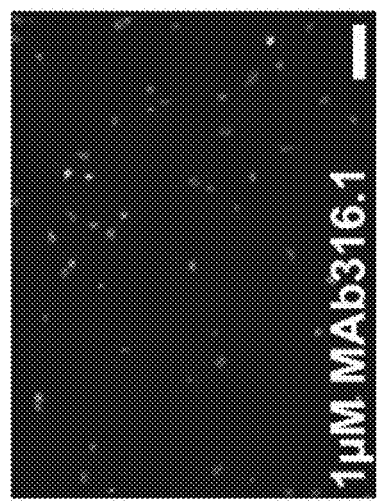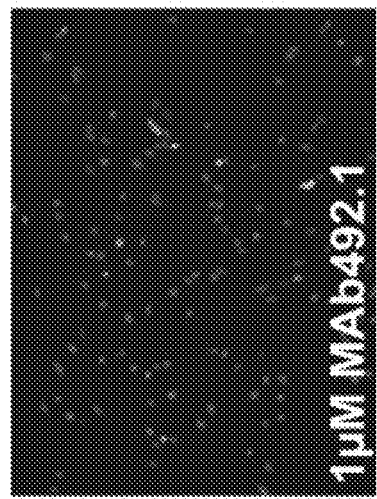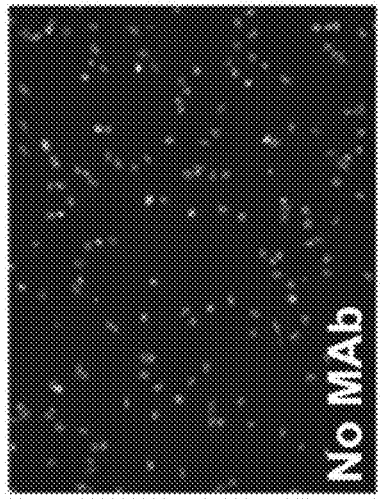

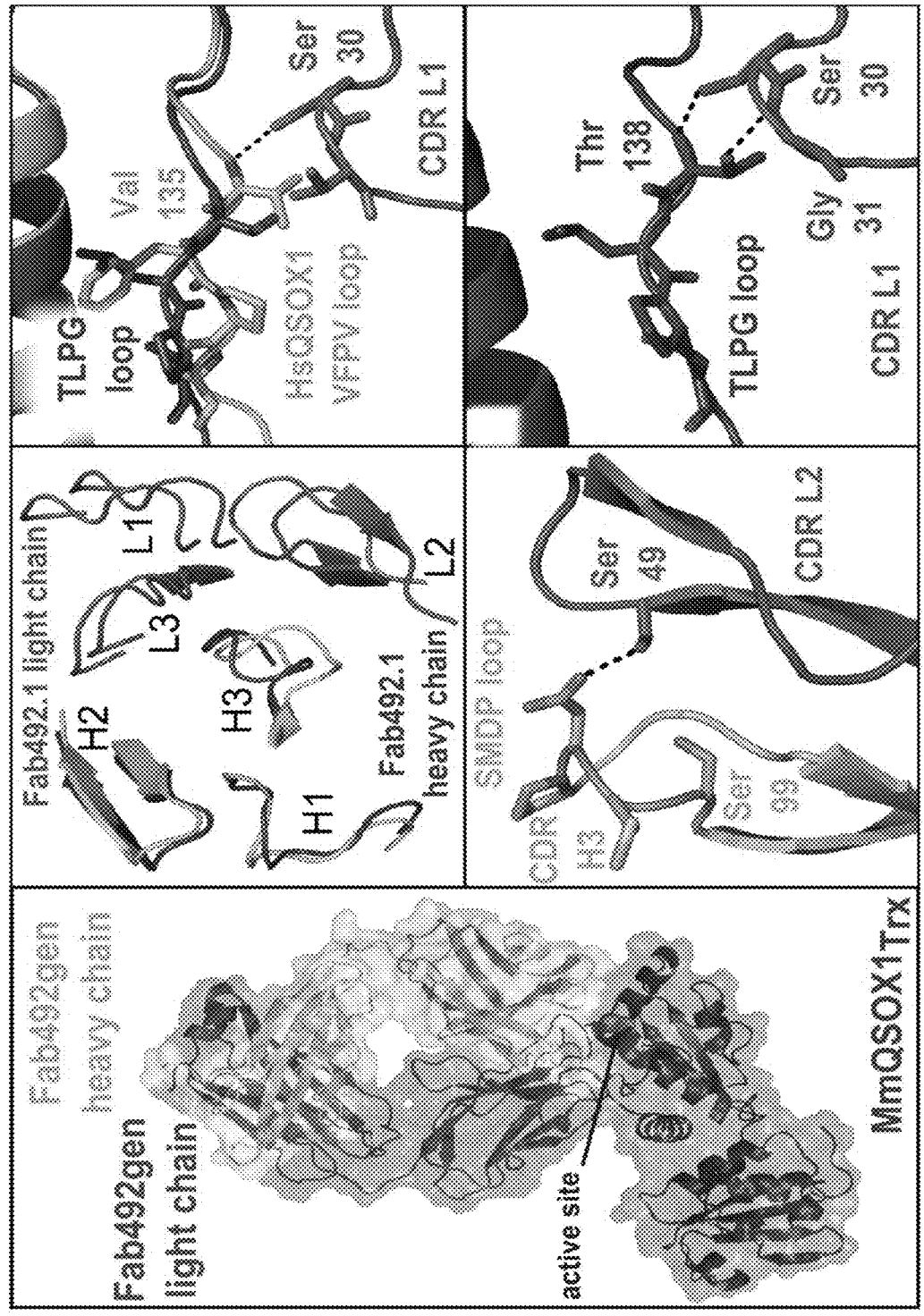

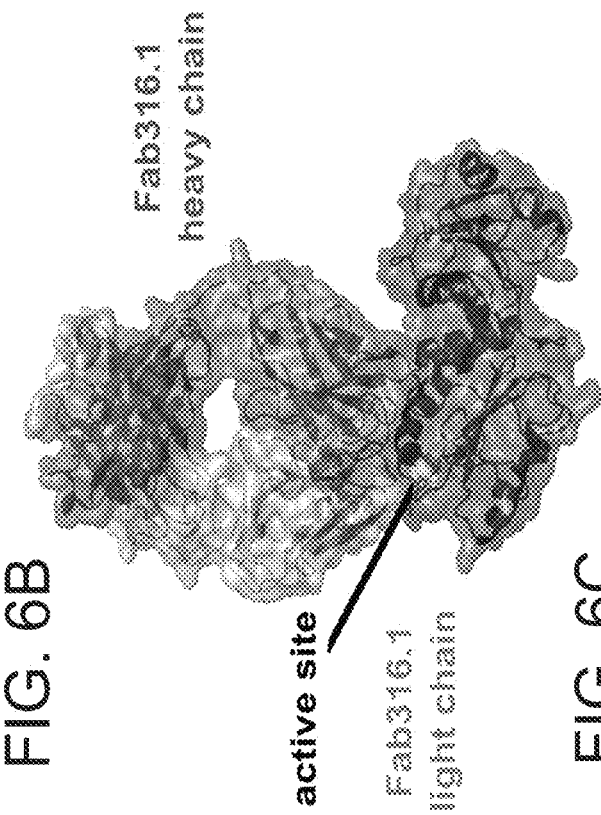
FIG. 6A
FIG. 6B
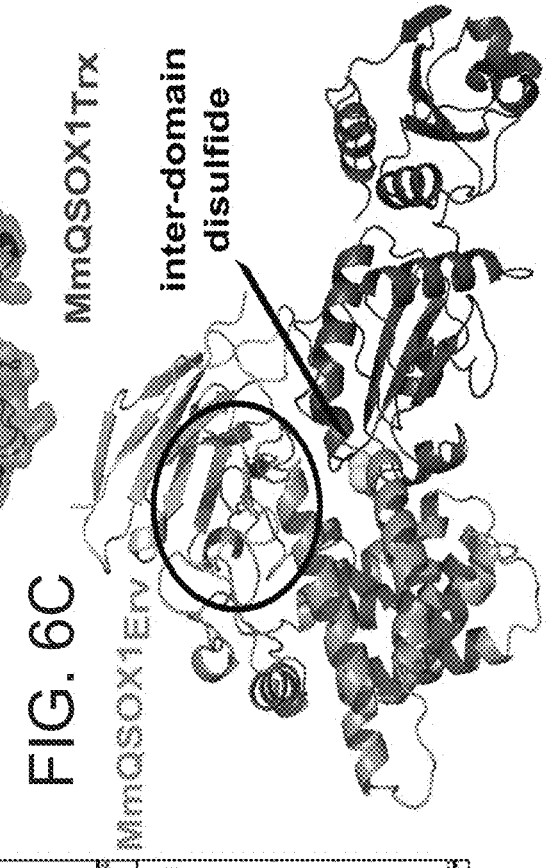
FIG. 6C

SEQUENCE LISTING

```
<160> NUMBER OF SEQ ID NOS: 51

<210> SEQ ID NO 1
<211> LENGTH: 3316
<212> TYPE: DNA
<213> ORGANISM: Homo sapiens

<400> SEQUENCE: 1
ggaggcaggc ggtgccgcgg cgccgggacc cgactcatcc ggtgcttgcg tgtggtggtg      60
agcgcagcgc cgaggatgag gaggtgcaac agcggctccg ggccgccgcc gtcgctgctg     120
ctgctgctgc tgtggctgct cgcggttccc ggcgctaacg cggccccgcg gtcggcgctc     180
tattcgcctt ccgacccgct gacgctgctg caggcggaca cggtgcgcgg cgcggtgctg     240
ggctcccgca gcgcctgggc cgtggagttc ttcgcctcct ggtgcggcca ctgcatcgcc     300
ttcgccccga cgtggaaggc gctggccgaa gacgtcaaag cctggaggcc ggccctgtat     360
ctcgccgccc tggactgtgc tgaggagacc aacagtgcag tctgcagaga cttcaacatc     420
cctggcttcc cgactgtgag gttcttcaag gcctttacca agaacggctc gggagcagta     480
tttccagtgg ctggtgctga cgtgcagaca ctgcgggaga ggctcattga cgccctggag     540
```

```
tcccatcatg acacgtggcc cccagcctgt cccccactgg agcctgccaa gctggaggag    600
attgatggat tctttgcgag aaataacgaa gagtacctgg ctctgatctt tgaaaaggga    660
ggctcctacc tgggtagaga ggtggctctg acctgtccc agcacaaagg cgtggcggtg    720
cgcagggtgc tgaacacaga ggccaatgtg gtgagaaagt tggtgtcac cgacttcccc    780 tcttgctacc tgctgttccg gaatggctct gtctcccgag tccccgtgct catggaatcc    840
aggtccttct ataccgctta cctgcagaga ctctctgggc tcaccaggga ggctgcccag    900
accacagttg caccaaccac tgctaacaag atagctccca ctgtttggaa attggcagat    960
cgctccaaga tctacatggc tgacctggaa tctgcactgc actacatcct gcggatagaa   1020
gtgggcaggt tcccggtcct ggaagggcag cgcctggtgg ccctgaaaaa gtttgtggca   1080
gtgctggcca agtatttccc tggccggccc ttagtccaga acttcctgca ctccgtgaat   1140
gaatggctca agaggcagaa gagaaataaa attccctaca gtttctttaa aactgccctg   1200
gacgacagga agagggtgc cgttcttgcc aagaaggtga actggattgg ctgccagggg   1260
agtgagccgc atttccgggg cttccctgc tccctgtggg tcctcttcca cttcttgact   1320
gtgcaggcag ctcggcaaaa tgtagaccac tcacaggaag cagccaaggc caaggaggtc   1380
ctcccagcca tccgaggcta cgtgcactac ttcttcggct gccagactg cgctagccac   1440 ttcgagcaga tggctgctgc ctccatgcac cgggtgggga gtcccaacgc cgctgtcctc   1500
tggctctggt ctagccacaa cagggtcaat gctcgccttg caggtgcccc cagcgaggac   1560
ccccagttcc ccaaggtgca gtggccaccc cgtgaacttt gttctgcctg ccacaatgaa   1620
cgcctggatg tgcccgtgtg ggacgtggaa gccaccctca acttcctcaa ggcccacttc   1680
tccccaagca acatcatcct ggacttccct gcagctgggt cagctgcccg gagggatgtg   1740
cagaatgtgg cagccgcccc agagctggcg atgggagccc tggagctgga aagccggaat   1800
tcaactctgg accctgggaa gcctgagatg atgaagtccc ccacaaacac caccccacat   1860
gtgccggctg agggacctga ggcaagtcga ccccgaagc tgcaccctgg cctcagagct   1920
gcaccaggcc aggagcctcc tgagcacatg gcagagcttc agaggaatga gcaggagcag   1980
ccgcttgggc agtggcactt gagcaagcga gacacagggg ctgcattgct ggctgagtcc   2040
agggctgaga agaaccgcct ctggggccct ttggaggtca ggcgcgtggg ccgcagctcc   2100
aagcagctgg tcgacatccc tgagggccag ctggaggccc gagctggacg gggccgaggc   2160
cagtggctgc aggtgctggg aggggcttc tcttacctgg acatcagcct ctgtgtgggg   2220
ctctattccc tgtccttcat gggctgctg gccatgtaca cctacttcca ggccaagata   2280
agggccctga agggccatgc tggccaccct gcagcctgaa ccacctgggg aggaggcggg   2340
agagggagct gccatctcta ggcacctcaa gccccctgac cccattccct ccctccccac   2400
cccttgctcc ttgtctggcc tagaagtgtg ggaaattcag gaaaacgagt tgctccagtg   2460
aagcttcttg gggttgctag gacagagagc tcctttgaca caaaagacag gagcagggtc   2520
caggttcccc tgctgtgcag ggagggcagc cccgggcagt gggcataggg cagctcagtc   2580
cctggcctct tagcaccaca ttcctgtttt tcagcttatt tgaagtcctg cctcattctc   2640 actgagcct cagtctctcc tgcttggtct tggccctcaa ctggggcaag tgaagccaga   2700
ggagggtccc ccagctgggt gggctggaat ggaactcctc actagctgct ggggctccgc   2760
ccaccctgct cccttccgga caatgaagaa gcctttgcac cctgggagga aggaccaccc   2820
cgggccctct atgcctggcc agcctccagc tcctcagacc tcctgggtgg ggtttggctt   2880
cagggtgggg tttggaagct tctggaagtc gtgctggtct cccaggtgag gcaagccatg   2940
```

```
gttgctgggc tgtagggtga gtggcttgct tggtgggacc tgacgagttg gtggcatggg    3000
aaggatgtgg gtctctagtg ccttgccctg gcttagctgc aggagaagat ggctgctttc    3060
acttcccccc attgagctct gctccctctg agcctggtct tttgtccttt tttatttttgg   3120 tctccaagat gaatgctcat cttttggaggg tgccaggtag aagctaggga ggggagtgtc   3180
ttctctctcc aggtttcacc ttccagtgtg cagaagttag aagggtctgg cgggggcagt   3240
gccttacaca tgcttgattc ccacgctacc ccctgccttg ggaggtgtgt ggaataaatt   3300
atttttgtta aggcaa                                                  3316

<210> SEQ ID NO 2
<211> LENGTH: 2583
<212> TYPE: DNA
<213> ORGANISM: Homo sapiens

<400> SEQUENCE: 2
ggaggcaggc ggtgccgcgg cgccgggacc cgactcatcc ggtgcttgcg tgtggtggtg      60
agcgcagcgc cgaggatgag gaggtgcaac agcggctccg ggccgccgcc gtcgctgctg     120
ctgctgctgc tgtggctgct cgcggttccc ggcgctaacg cggccccgcg gtcggcgctc     180
tattcgcctt ccgacccgct gacgctgctg caggcggaca cggtgcgcgg cgcggtgctg     240
ggctcccgca gcgcctgggc cgtggagttc ttcgcctcct ggtgcggcca ctgcatcgcc     300
ttcgccccga cgtggaaggc gctggccgaa gacgtcaaag cctggaggcc ggccctgtat     360
ctcgccgccc tggactgtgc tgaggagacc aacagtgcag tctgcagaga cttcaacatc     420
cctggcttcc cgactgtgag gttcttcaag gcctttacca agaacggctc gggagcagta     480
tttccagtgg ctggtgctga cgtgcagaca ctgcgggaga ggctcattga cgccctggag     540
tcccatcatg acacgtggcc ccagcctgt cccccactgg agcctgccaa gctggaggag      600
attgatggat tctttgcgag aaataacgaa gagtacctgg ctctgatctt tgaaaaggga     660
ggctcctacc tgggtagaga ggtggctctg gacctgtccc agcacaaagg cgtggcggtg     720
cgcagggtgc tgaacacaga ggccaatgtg gtgagaaagt ttggtgtcac cgacttcccc     780
tcttgctacc tgctgttccg gaatggctct gtctcccgag tccccgtgct catggaatcc     840
aggtccttct ataccgctta cctgcagaga ctctctgggc tcaccaggga ggctgcccag     900
accacagttg caccaaccac tgctaacaag atagctccca ctgtttggaa attggcagat     960
cgctccaaga tctacatggc tgacctggaa tctgcactgc actacatcct gcggatagaa    1020
gtgggcaggt tccggtcct ggaagggcag cgcctggtgg ccctgaaaaa gtttgtggca    1080
gtgctggcca agtatttccc tggccggccc ttagtccaga acttcctgca ctccgtgaat    1140
gaatggctca gaggcagaa gagaaataaa attccctaca gtttctttaa aactgccctg    1200
gacgacagga agagggtgc cgttcttgcc aagaaggtga actggattgg ctgccaggg     1260 agtgagccgc atttccgggg cttctccctgc ccctgtggg tcctcttcca cttcttgact    1320
gtgcaggcag ctcggcaaaa tgtagaccac tcacaggaag cagccaaggc caaggaggtc    1380
ctcccagcca tccgaggcta cgtgcactac ttcttcggct gccgagactg cgctagccac    1440
ttcgagcaga tggctgctgc ctccatgcac cgggtgggga gtcccaacgc cgctgtcctc    1500
tggctctggt ctagccacaa cagggtcaat gctcgccttg caggtgcccc cagcgaggac    1560
ccccagttcc ccaaggtgca gtggccaccc cgtgaacttt gttctgcctg ccacaatgaa    1620
cgcctggatg tgcccgtgtg ggacgtggaa gccacccctca acttcctcaa ggcccacttc    1680
tccccaagca acatcatcct ggacttccct gcagctgggt cagctgcccg gagggatgtg    1740
```

```
cagaatgtgg cagccgcccc agagctggcg atgggagccc tggagctgga aagccggaat    1800
tcaactctgg accctgggaa gcctgagatg atgaagtccc ccacaaacac caccccacat    1860
gtgccggctg agggacctga gcttatttga agtcctgcct cattctcact ggagcctcag    1920
tctctcctgc ttggtcttgg ccctcaactg gggcaagtga agccagagga gggtccccca    1980
gctgggtggg ctggaatgga actcctcact agctgctggg gctccgccca ccctgctccc    2040
ttccggacaa tgaagaagcc tttgcaccct gggaggaagg accacccggg ccctctatg    2100 cctggccagc ctccagctcc tcagacctcc tgggtggggt ttggcttcag ggtggggttt    2160
ggaagcttct ggaagtcgtg ctggtctccc aggtgaggca agccatggtt gctgggctgt    2220
agggtgagtg gcttgcttgg tgggacctga cgagttggtg gcatgggaag gatgtgggtc    2280
tctagtgcct tgccctggct tagctgcagg agaagatggc tgctttcact tcccccatt     2340 gagctctgct ccctctgagc ctggtctttt gtccttttt attttggtct ccaagatgaa     2400
tgctcatctt tggagggtgc caggtagaag ctagggaggg gagtgtcttc tctctccagg    2460
tttcaccttc cagtgtgcag aagttagaag ggtctggcgg gggcagtgcc ttacacatgc    2520
ttgattccca cgctaccccc tgccttggga ggtgtgtgga ataaattatt tttgttaagg    2580
caa                                                                  2583

<210> SEQ ID NO 3
<211> LENGTH: 747
<212> TYPE: PRT
<213> ORGANISM: Homo sapiens

<400> SEQUENCE: 3

Met Arg Arg Cys Asn Ser Gly Ser Gly Pro Pro Ser Leu Leu Leu
1               5                   10                  15

Leu Leu Leu Trp Leu Leu Ala Val Pro Gly Ala Asn Ala Ala Pro Arg
                20                  25                  30

Ser Ala Leu Tyr Ser Pro Ser Asp Pro Leu Thr Leu Leu Gln Ala Asp
            35                  40                  45

Thr Val Arg Gly Ala Val Leu Gly Ser Arg Ser Ala Trp Ala Val Glu
        50                  55                  60

Phe Phe Ala Ser Trp Cys Gly His Cys Ile Ala Phe Ala Pro Thr Trp
65                  70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
            100                 105                 110

Phe Asn Ile Pro Gly Phe Pro Thr Val Arg Phe Phe Lys Ala Phe Thr
        115                 120                 125

Lys Asn Gly Ser Gly Ala Val Phe Pro Val Ala Gly Ala Asp Val Gln
    130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
        195                 200                 205

Gln His Lys Gly Val Ala Val Arg Arg Val Leu Asn Thr Glu Ala Asn
    210                 215                 220
```

-continued

```
Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
            245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
            290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
            325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
            355                 360                 365

Ser Phe Phe Lys Thr Ala Leu Asp Asp Arg Lys Glu Gly Ala Val Leu
            370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
            405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
            435                 440                 445

Cys Arg Asp Cys Ala Ser His Phe Glu Gln Met Ala Ala Ala Ser Met
450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
            485                 490                 495

Gln Phe Pro Lys Val Gln Trp Pro Arg Glu Leu Cys Ser Ala Cys
            500                 505                 510

His Asn Glu Arg Leu Asp Val Pro Val Trp Asp Val Glu Ala Thr Leu
            515                 520                 525

Asn Phe Leu Lys Ala His Phe Ser Pro Ser Asn Ile Ile Leu Asp Phe
            530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
            565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Ala Ser Arg Pro Pro Lys
            595                 600                 605

Leu His Pro Gly Leu Arg Ala Ala Pro Gly Gln Glu Pro Pro Glu His
            610                 615                 620

Met Ala Glu Leu Gln Arg Asn Glu Gln Glu Gln Pro Leu Gly Gln Trp
625                 630                 635                 640
```

```
His Leu Ser Lys Arg Asp Thr Gly Ala Ala Leu Leu Ala Glu Ser Arg
                645                 650                 655
Ala Glu Lys Asn Arg Leu Trp Gly Pro Leu Glu Val Arg Arg Val Gly
            660                 665                 670
Arg Ser Ser Lys Gln Leu Val Asp Ile Pro Glu Gly Gln Leu Glu Ala
        675                 680                 685
Arg Ala Gly Arg Gly Arg Gly Gln Trp Leu Gln Val Leu Gly Gly Gly
    690                 695                 700
Phe Ser Tyr Leu Asp Ile Ser Leu Cys Val Gly Leu Tyr Ser Leu Ser
705                 710                 715                 720
Phe Met Gly Leu Leu Ala Met Tyr Thr Tyr Phe Gln Ala Lys Ile Arg
                725                 730                 735
Ala Leu Lys Gly His Ala Gly His Pro Ala Ala
            740                 745

<210> SEQ ID NO 4
<211> LENGTH: 604
<212> TYPE: PRT
<213> ORGANISM: Homo sapiens

<400> SEQUENCE: 4

Met Arg Arg Cys Asn Ser Gly Ser Gly Pro Pro Ser Leu Leu Leu
1               5                   10                  15
Leu Leu Leu Trp Leu Leu Ala Val Pro Gly Ala Asn Ala Ala Pro Arg
                20                  25                  30
Ser Ala Leu Tyr Ser Pro Ser Asp Pro Leu Thr Leu Leu Gln Ala Asp
            35                  40                  45
Thr Val Arg Gly Ala Val Leu Gly Ser Arg Ser Ala Trp Ala Val Glu
    50                  55                  60
Phe Phe Ala Ser Trp Cys Gly His Cys Ile Ala Phe Ala Pro Thr Trp
65                  70                  75                  80
Lys Ala Leu Ala Glu Asp Val Lys Ala Trp Arg Pro Ala Leu Tyr Leu
                85                  90                  95
Ala Ala Leu Asp Cys Ala Glu Glu Thr Asn Ser Ala Val Cys Arg Asp
            100                 105                 110
Phe Asn Ile Pro Gly Phe Pro Thr Val Arg Phe Phe Lys Ala Phe Thr
        115                 120                 125
Lys Asn Gly Ser Gly Ala Val Phe Pro Val Ala Gly Ala Asp Val Gln
    130                 135                 140
Thr Leu Arg Glu Arg Leu Ile Asp Ala Leu Glu Ser His His Asp Thr
145                 150                 155                 160
Trp Pro Pro Ala Cys Pro Pro Leu Glu Pro Ala Lys Leu Glu Glu Ile
                165                 170                 175
Asp Gly Phe Phe Ala Arg Asn Asn Glu Glu Tyr Leu Ala Leu Ile Phe
            180                 185                 190
Glu Lys Gly Gly Ser Tyr Leu Gly Arg Glu Val Ala Leu Asp Leu Ser
        195                 200                 205
Gln His Lys Gly Val Ala Val Arg Arg Val Leu Asn Thr Glu Ala Asn
    210                 215                 220
Val Val Arg Lys Phe Gly Val Thr Asp Phe Pro Ser Cys Tyr Leu Leu
225                 230                 235                 240
Phe Arg Asn Gly Ser Val Ser Arg Val Pro Val Leu Met Glu Ser Arg
                245                 250                 255
Ser Phe Tyr Thr Ala Tyr Leu Gln Arg Leu Ser Gly Leu Thr Arg Glu
                260                 265                 270
```

-continued

```
Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
            325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
            355                 360                 365

Ser Phe Phe Lys Thr Ala Leu Asp Asp Arg Lys Glu Gly Ala Val Leu
            370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                    405                 410                 415

Gln Ala Ala Arg Gln Asn Val Asp His Ser Gln Glu Ala Ala Lys Ala
                    420                 425                 430

Lys Glu Val Leu Pro Ala Ile Arg Gly Tyr Val His Tyr Phe Phe Gly
            435                 440                 445

Cys Arg Asp Cys Ala Ser His Phe Glu Gln Met Ala Ala Ala Ser Met
            450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                    485                 490                 495

Gln Phe Pro Lys Val Gln Trp Pro Pro Arg Glu Leu Cys Ser Ala Cys
                    500                 505                 510

His Asn Glu Arg Leu Asp Val Pro Val Trp Asp Val Glu Ala Thr Leu
            515                 520                 525

Asn Phe Leu Lys Ala His Phe Ser Pro Ser Asn Ile Ile Leu Asp Phe
530                 535                 540

Pro Ala Gly Ser Ala Ala Arg Arg Asp Val Gln Asn Val Ala Ala
545                 550                 555                 560

Ala Pro Glu Leu Ala Met Gly Ala Leu Glu Leu Ser Arg Asn Ser
                    565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Leu Ile
            595                 600
```

<210> SEQ ID NO 5
<211> LENGTH: 604
<212> TYPE: PRT
<213> ORGANISM: Homo sapiens

<400> SEQUENCE: 5

```
Met Arg Arg Cys Asn Ser Gly Ser Gly Pro Pro Pro Ser Leu Leu Leu
1               5                   10                  15

Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Leu Gln Ala Asp
        35                  40                  45
```

-continued

Thr Val Arg Gly Ala Val Leu Gly Ser Arg Ser Ala Trp Ala Val Glu
 50              55                  60

Phe Phe Ala Ser Trp Cys Gly His Cys Ile Ala Phe Ala Pro Thr Trp
 65              70                  75                  80

Lys Ala Leu Ala Glu Asp Val Lys Ala Trp Arg Pro Ala Leu Tyr Leu
                 85                  90                  95

Ala Ala Leu Asp Cys Ala Glu Glu Thr Asn Ser Ala Val Cys Arg Asp
                100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
            130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
                180                 185                 190

Glu Lys Gly Gly Ser Tyr Leu Gly Arg Glu Val Ala Leu Asp Leu Ser
            195                 200                 205

Gln His Lys Gly Val Ala Val Arg Arg Val Leu Asn Thr Glu Ala Asn
            210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
                260                 265                 270

Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
            355                 360                 365

Ser Phe Phe Lys Thr Ala Leu Asp Asp Arg Lys Glu Gly Ala Val Leu
            370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
            435                 440                 445

Cys Arg Asp Cys Ala Ser His Phe Glu Gln Met Ala Ala Ala Ser Met
450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
            485                 490                 495

Gln Phe Pro Lys Val Gln Trp Pro Pro Arg Glu Leu Cys Ser Ala Cys
            500                 505                 510

His Asn Glu Arg Leu Asp Val Pro Val Trp Asp Val Glu Ala Thr Leu
            515                 520                 525

Asn Phe Leu Lys Ala His Phe Ser Pro Ser Asn Ile Ile Leu Asp Phe
            530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
            565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Leu Ile
            595                 600

<210> SEQ ID NO 6
<211> LENGTH: 748
<212> TYPE: PRT
<213> ORGANISM: Mus musculus

<400> SEQUENCE: 6

Met Arg Arg Cys Gly Arg Leu Ser Gly Pro Ser Leu Leu Leu Leu Leu
1               5                   10                  15

Leu Leu Leu Leu Ser Pro Leu Leu Phe Ser Gly Pro Gly Ala Tyr Ala
            20                  25                  30

Ala Arg Leu Ser Val Leu Tyr Ser Ser Asp Pro Leu Thr Leu Leu
            35                  40                  45

Asp Ala Asp Ser Val Arg Pro Thr Val Leu Gly Ser Ser Ser Ala Trp
50                  55                  60

Ala Val Glu Phe Phe Ala Ser Trp Cys Gly His Cys Ile Ala Phe Ala
65                  70                  75                  80

Pro Thr Trp Lys Glu Leu Ala Asn Asp Val Lys Asp Trp Arg Pro Ala
            85                  90                  95

Leu Asn Leu Ala Val Leu Asp Cys Ala Glu Glu Thr Asn Ser Ala Val
            100                 105                 110

Cys Arg Glu Phe Asn Ile Ala Gly Phe Pro Thr Val Arg Phe Phe Gln
            115                 120                 125

Ala Phe Thr Lys Asn Gly Ser Gly Ala Thr Leu Pro Gly Ala Gly Ala
            130                 135                 140

Asn Val Gln Thr Leu Arg Met Arg Leu Ile Asp Ala Leu Glu Ser His
145                 150                 155                 160

Arg Asp Thr Trp Pro Ala Cys Pro Pro Leu Glu Pro Ala Lys Leu
            165                 170                 175

Asn Asp Ile Asp Gly Phe Phe Thr Arg Asn Lys Ala Asp Tyr Leu Ala
            180                 185                 190

Leu Val Phe Glu Arg Glu Asp Ser Tyr Leu Gly Arg Glu Val Thr Leu
            195                 200                 205

Asp Leu Ser Gln Tyr His Ala Val Ala Val Arg Arg Val Leu Asn Thr
            210                 215                 220

Glu Ser Asp Leu Val Asn Lys Phe Gly Val Thr Asp Phe Pro Ser Cys
225                 230                 235                 240

```
Tyr Leu Leu Leu Arg Asn Gly Ser Val Ser Arg Val Pro Val Leu Val
            245                 250                 255

Glu Ser Arg Ser Phe Tyr Thr Ser Tyr Leu Arg Gly Leu Pro Gly Leu
        260                 265                 270

Thr Arg Asp Ala Pro Pro Thr Thr Ala Thr Pro Val Thr Ala Asp Lys
    275                 280                 285

Ile Ala Pro Thr Val Trp Lys Phe Ala Asp Arg Ser Lys Ile Tyr Met
290                 295                 300

Ala Asp Leu Glu Ser Ala Leu His Tyr Ile Leu Arg Val Glu Val Gly
305                 310                 315                 320

Lys Phe Ser Val Leu Glu Gly Gln Arg Leu Val Ala Leu Lys Lys Phe
                325                 330                 335

Val Ala Val Leu Ala Lys Tyr Phe Pro Gly Gln Pro Leu Val Gln Asn
            340                 345                 350

Phe Leu His Ser Ile Asn Asp Trp Leu Gln Lys Gln Gln Lys Lys Arg
        355                 360                 365

Ile Pro Tyr Ser Phe Phe Lys Ala Ala Leu Asp Ser Arg Lys Glu Asp
    370                 375                 380

Ala Val Leu Thr Glu Lys Val Asn Trp Val Gly Cys Gln Gly Ser Glu
385                 390                 395                 400

Pro His Phe Arg Gly Phe Pro Cys Ser Leu Trp Val Leu Phe His Phe
                405                 410                 415

Leu Thr Val Gln Ala Asn Arg Tyr Ser Glu Ala His Pro Gln Glu Pro
            420                 425                 430

Ala Asp Gly Gln Glu Val Leu Gln Ala Met Arg Ser Tyr Val Gln Phe
        435                 440                 445

Phe Phe Gly Cys Arg Asp Cys Ala Asp His Phe Glu Gln Met Ala Ala
    450                 455                 460

Ala Ser Met His Gln Val Arg Ser Pro Ser Asn Ala Ile Leu Trp Leu
465                 470                 475                 480

Trp Thr Ser His Asn Arg Val Asn Ala Arg Leu Ser Gly Ala Leu Ser
                485                 490                 495

Glu Asp Pro His Phe Pro Lys Val Gln Trp Pro Pro Arg Glu Leu Cys
            500                 505                 510

Ser Ala Cys His Asn Glu Leu Asn Gly Gln Val Pro Leu Trp Asp Leu
        515                 520                 525

Gly Ala Thr Leu Asn Phe Leu Lys Ala His Phe Ser Pro Ala Asn Ile
    530                 535                 540

Val Ile Asp Ser Ser Ala Ser Arg His Thr Gly Arg Arg Gly Ser Pro
545                 550                 555                 560

Glu Ala Thr Pro Glu Leu Val Met Asp Thr Leu Lys Leu Glu Ser Arg
                565                 570                 575

Asn Ser Val Leu Gly His Glu Gln Ala Ala Ser Ala Glu Ser Pro Gly
            580                 585                 590

Ala Thr Ala Leu Asp Val Pro Ala Glu Lys Pro Glu Ala Ser Gly Pro
        595                 600                 605

Gln Glu Leu Tyr Thr Gly Leu Arg Met Gly Ala Ser Pro Gly Gln
    610                 615                 620

Gly Pro Pro Glu Arg Met Glu Asp His Gln Arg Asp Met Gln Glu Asn
625                 630                 635                 640

Ala Pro Gly Gln Gln His Leu Ser Lys Arg Asp Thr Glu Ala Leu Phe
                645                 650                 655
```

-continued

```
Leu Pro Glu Val Asn His Leu Gln Gly Pro Leu Glu Leu Arg Arg Gly
                660                 665                 670

Gly Arg Ser Pro Lys Gln Leu Ala Pro Ile Leu Glu Glu Pro Glu
        675                 680                 685

Ala Leu Ala Ile Gln Gly Gln Gly Gln Trp Leu Gln Val Leu Gly Gly
690                 695                 700

Gly Ile Ser His Leu Asp Ile Ser Leu Cys Val Gly Leu Tyr Ser Val
705                 710                 715                 720

Ser Phe Met Gly Leu Ala Met Tyr Thr Tyr Phe Arg Ala Arg Leu
                725                 730                 735

Arg Thr Pro Lys Gly His Ala Ser Tyr Pro Thr Ala
                740                 745
```

<210> SEQ ID NO 7
<211> LENGTH: 750
<212> TYPE: PRT
<213> ORGANISM: Rattus norvegicus

<400> SEQUENCE: 7

```
Met Arg Arg Cys Gly Arg His Ser Gly Pro Pro Ser Leu Leu Leu Leu
1               5                   10                  15

Leu Leu Leu Leu Pro Pro Leu Leu Leu Ser Val Pro Gly Ala Tyr Ala
                20                  25                  30

Ala Arg Leu Ser Val Leu Tyr Ser Ser Asp Pro Leu Thr Leu Leu
            35                  40                  45

Asp Ala Asp Thr Val Arg Pro Ala Val Leu Gly Ser Ser Ser Ala Trp
    50                  55                  60

Ala Val Glu Phe Phe Ala Ser Trp Cys Gly His Cys Ile Ala Phe Ala
65                  70                  75                  80

Pro Thr Trp Lys Glu Leu Ala Asn Asp Val Lys Asp Trp Arg Pro Ala
                85                  90                  95

Leu Asn Leu Ala Val Leu Asp Cys Ala Asp Glu Thr Asn Ser Ala Val
            100                 105                 110

Cys Arg Glu Phe Asn Ile Ala Gly Phe Pro Thr Val Arg Phe Phe Lys
    115                 120                 125

Ala Phe Ser Lys Asn Gly Thr Gly Thr Ala Leu Pro Ala Ala Gly Ala
130                 135                 140

Asn Val Gln Thr Leu Arg Met Arg Leu Ile Asp Ala Leu Glu Ser His
145                 150                 155                 160

Arg Asp Thr Trp Pro Pro Ala Cys Pro Pro Leu Glu Pro Ala Lys Leu
                165                 170                 175

Lys Asp Ile Asn Glu Phe Phe Thr Arg Ser Lys Ala Glu Tyr Leu Ala
            180                 185                 190

Leu Ile Phe Glu Arg Glu Asp Ser Tyr Leu Gly Arg Glu Val Thr Leu
    195                 200                 205

Asp Leu Ser Gln Phe His Ala Val Ala Val Arg Arg Val Leu Asn Ser
210                 215                 220

Glu Ser Asp Val Val Ser Lys Phe Ala Val Thr Asp Phe Pro Ser Cys
225                 230                 235                 240

Tyr Leu Leu Leu Arg Asn Gly Ser Val Ser Arg Val Pro Val Leu Val
                245                 250                 255

Glu Ser Arg Pro Phe Tyr Thr Ser Tyr Leu Arg Gly Leu Pro Gly Leu
            260                 265                 270

Thr Arg Glu Ala Pro Pro Thr Thr Ala Ala Pro Val Thr Pro Asp Lys
    275                 280                 285
```

```
Ile Ala Pro Thr Val Trp Lys Phe Ala Asp Arg Ser Lys Ile Tyr Met
290                 295                 300
Ala Asp Leu Glu Ser Ala Leu His Tyr Ile Leu Arg Val Glu Val Gly
305                 310                 315                 320
Lys Phe Ser Val Leu Glu Gly Gln Arg Leu Val Ala Leu Lys Lys Phe
                325                 330                 335
Val Ala Val Leu Ala Lys Tyr Phe Pro Gly Gln Pro Leu Val Gln Asn
                340                 345                 350
Phe Leu His Ser Ile Asn Asp Trp Leu Gln Lys Gln Lys Lys Lys
                355                 360                 365
Ile Pro Tyr Ser Tyr Phe Lys Ala Ala Leu Asp Ser Arg Lys Glu Asn
370                 375                 380
Ala Val Leu Ala Glu Lys Val Asn Trp Ile Gly Cys Gln Gly Ser Glu
385                 390                 395                 400
Pro His Phe Arg Gly Phe Pro Cys Ser Leu Trp Val Leu Phe His Phe
                405                 410                 415
Leu Thr Val Gln Ala His Arg Tyr Ser Glu Ala His Pro Gln Glu Pro
                420                 425                 430
Ala Asp Gly Gln Glu Val Leu Gln Ala Met Arg Ser Tyr Val Gln Ser
                435                 440                 445
Phe Phe Gly Cys Arg Asp Cys Ala Asn His Phe Glu Gln Met Ala Ala
                450                 455                 460
Ala Ser Met His Gln Val Lys Ser Pro Ser Asn Ala Val Leu Trp Leu
465                 470                 475                 480
Trp Thr Ser His Asn Arg Val Asn Ala Arg Leu Ser Gly Ala Leu Ser
                485                 490                 495
Glu Asp Pro Gln Phe Pro Lys Val Gln Trp Pro Pro Arg Glu Leu Cys
                500                 505                 510
Ser Ala Cys His Asn Glu Val Asn Gly Gln Val Pro Leu Trp Asp Leu
                515                 520                 525
Gly Ala Thr Leu Asn Phe Leu Lys Ala His Phe Ser Pro Ala Asn Ile
                530                 535                 540
Val Arg Asp Pro Pro Ala Pro Gly Pro Ala Ser Arg Arg Gly Thr Gln
545                 550                 555                 560
Asp Pro Glu Ala Ser Pro Asn Leu Val Met Asp Thr Leu Lys Leu Glu
                565                 570                 575
Thr Gly Asn Ser Val Leu Gly His Glu Gln Ala Ala Ser Ala Ala Ser
                580                 585                 590
Pro Gly Ala Thr Ala Leu Asp Val Pro Ala Gly Lys Pro Glu Ala Ser
                595                 600                 605
Gly Pro Gln Glu Leu Asn Ala Gly Leu Ser Met Gly Gly Ala Ser Pro
                610                 615                 620
Gly Gln Gly Pro Pro Glu His Thr Glu Glu Leu Leu Arg Asp Val Gln
625                 630                 635                 640
Glu Asn Ala Gln Gly Gln His Leu Ser Lys Arg Asp Thr Glu Ala
                645                 650                 655
Leu Leu Leu Pro Glu Val Asn His Leu Gln Gly Pro Leu Ala Pro Arg
                660                 665                 670
Arg Gly Gly His Ser Pro Lys Gln Leu Ala Ser Ile Leu Glu Gly Glu
                675                 680                 685
```

```
Pro Glu Ala Leu Ala Ile Gln Gly Arg Arg Gln Trp Leu Gln Val Leu
    690             695                 700

Gly Gly Gly Val Ser Phe Leu Asp Ile Ser Leu Cys Val Gly Leu Tyr
705             710                 715                 720

Ser Val Ser Phe Met Gly Leu Leu Ala Met Tyr Thr Tyr Phe Arg Ala
                725             730                 735

Arg Met Arg Thr Pro Lys Gly His Val Ser Tyr Pro Thr Ala
            740             745                 750

<210> SEQ ID NO 8
<211> LENGTH: 613
<212> TYPE: PRT
<213> ORGANISM: Cavia porcellus

<400> SEQUENCE: 8

Met Thr Gly Cys Gly Arg Arg Ser Gly Trp Leu Pro Pro Leu Arg Leu
1               5                   10                  15

Leu Leu Pro Leu Leu Leu Gly Gly Pro Gly Val Gly Ala Ala Gln
            20                  25                  30

Leu Ala Ala Leu Tyr Ser Ala Ser Asp Pro Leu Thr Leu Leu Gln Ala
                35                  40                  45

Asp Thr Val Arg Ser Thr Val Leu Asn Ser Pro Ser Ala Trp Ala Val
    50                  55                  60

Glu Phe Phe Ala Ser Trp Cys Gly His Cys Ile Ala Phe Ala Pro Thr
65              70                  75                  80

Trp Lys Ala Leu Ala Lys Asp Ile Lys Asp Trp Arg Pro Ala Leu Asn
                85                  90                  95

Leu Ala Ala Leu Asn Cys Ala Asp Glu Thr Asn Asn Ala Val Cys Arg
            100                 105                 110

Asp Phe Asn Ile Ala Gly Phe Pro Ser Val Arg Phe Phe Lys Ala Phe
                115                 120                 125

Ser Lys Asn Ser Thr Gly Thr Thr Leu Pro Val Ala Gly Ala Asn Val
    130                 135                 140

Gln Met Leu Arg Glu Arg Leu Ile Asp Ala Leu Glu Ser His His Asp
145                 150                 155                 160

Thr Trp Pro Ser Ala Cys Pro Pro Leu Glu Pro Val Lys Pro Lys Glu
                165                 170                 175

Ile Asp Thr Phe Phe Ala Arg Asn Asn Gln Glu Tyr Leu Val Leu Ile
                180                 185                 190

Phe Glu Gln Glu Asn Ser Tyr Leu Gly Arg Glu Val Thr Leu Asp Leu
            195                 200                 205

Ser Gln His His Asp Leu Val Val Arg Arg Val Leu Ser Thr Glu Ala
    210                 215                 220

Asn Val Val Arg Lys Phe Gly Val Ala Asp Phe Pro Ser Cys Tyr Leu
225                 230                 235                 240

Leu Phe Arg Asn Gly Ser Val Ser Arg Val Pro Val Leu Val Glu Ser
                245                 250                 255

Arg Arg Phe Tyr Thr Ala Tyr Leu Gln Arg Leu Ser Glu Val Thr Arg
                260                 265                 270

Glu Gly Thr Pro Thr Pro Ala Val Pro Thr Ile Ser Asp Gln Ile Ala
            275                 280                 285

Pro Thr Val Trp Lys Phe Ala Asp Arg Ser Lys Ile Tyr Met Ala Asp
    290                 295                 300

Leu Glu Ser Ala Leu His Tyr Ile Leu Arg Val Glu Val Gly Arg Phe
305                 310                 315                 320
```

```
Ser Val Leu Glu Gly Gln Arg Leu Met Ala Leu Lys Lys Phe Val Thr
            325                 330                 335

Val Leu Thr Lys Tyr Phe Pro Gly Gln Pro Leu Val Arg Asn Phe Leu
        340                 345                 350

Gln Ser Thr Asn Glu Trp Leu Lys Arg Gln His Lys Lys Lys Met Pro
            355                 360                 365

Tyr Ser Phe Lys Thr Ala Met Asp Ser Arg Asn Glu Glu Ala Val
370                 375                 380

Ile Thr Lys Glu Val Asn Trp Val Gly Cys Gln Gly Ser Glu Ser His
385                 390                 395                 400

Phe Arg Gly Phe Pro Cys Ser Leu Trp Ile Leu Phe His Phe Leu Thr
            405                 410                 415

Val Gln Ala Ser Gln Lys Asn Ala Glu Ser Ser Gln Lys Pro Ala Asn
        420                 425                 430

Gly Gln Glu Val Leu Gln Ala Ile Arg Asn Tyr Val Arg Phe Phe Phe
            435                 440                 445

Gly Cys Arg Asp Cys Ala Asn His Phe Glu Gln Met Ala Ala Gly Ser
450                 455                 460

Met His Arg Val Lys Ser Pro Asn Asp Ala Val Leu Trp Leu Trp Thr
465                 470                 475                 480

Ser His Asn Arg Val Asn Ala Arg Leu Ala Gly Ala Pro Ser Glu Asp
            485                 490                 495

Pro Gln Phe Pro Lys Val Gln Trp Pro Pro Glu Leu Cys Ser Ala
        500                 505                 510

Cys His Asn Glu Leu Ser Gly Glu Pro Val Trp Asp Val Asp Ala Thr
            515                 520                 525

Leu Arg Phe Leu Lys Thr His Phe Ser Pro Ser Asn Ile Val Leu Asn
530                 535                 540

Phe Pro Pro Ala Glu Pro Ala Ser Arg Ser Ser Val His Ser Trp Gly
545                 550                 555                 560

Ala Thr Pro His Leu Glu Leu Asp Ala Leu Gly Leu Val Thr Arg Asn
            565                 570                 575

Ser Ala Leu Ala Leu Glu Arg Ala Glu Ile Ser Glu Ser Pro Gly Ser
        580                 585                 590

Asn Ala Met Pro Asn Ile Pro Ala Glu Arg Pro Glu Leu Phe Glu Ala
            595                 600                 605

Leu Ser His Ser Arg
    610

<210> SEQ ID NO 9
<211> LENGTH: 106
<212> TYPE: PRT
<213> ORGANISM: Artificial Sequence
<220> FEATURE:
<223> OTHER INFORMATION: MAb316.1 variable region - light chain

<400> SEQUENCE: 9

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Tyr Trp Tyr His Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
50                  55                  60
```

```
Gly Ser Gly Thr Ser Tyr Ser Leu Thr Ile Ser Met Glu Ala Glu
 65                  70                  75                  80

Asp Ala Ala Thr Tyr Tyr Cys Gln Gln Tyr His Ser Tyr Pro Leu Thr
                 85                  90                  95

Phe Gly Ala Gly Thr Lys Leu Glu Leu Lys
                100                 105

<210> SEQ ID NO 10
<211> LENGTH: 115
<212> TYPE: PRT
<213> ORGANISM: Artificial Sequence
<220> FEATURE:
<223> OTHER INFORMATION: MAb316.1 variable region - heavy chain

<400> SEQUENCE: 10

Gln Val Gln Leu Gln Gln Ser Gly Pro Glu Leu Val Lys Pro Gly Ala
  1               5                  10                  15

Ser Val Lys Ile Ser Cys Lys Ala Ser Gly Tyr Ser Phe Thr Ser Tyr
                 20                  25                  30

Tyr Ile His Trp Val Lys Gln Arg Pro Gly Gln Gly Leu Glu Trp Ile
             35                  40                  45

Gly Trp Ile Tyr Pro Gly Ser Tyr Asn Thr Glu Tyr Ser Glu Lys Phe
 50                  55                  60

Lys Gly Lys Ala Thr Leu Thr Ala Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Glu Asp Trp Phe Ala Tyr Trp Gly Gln Gly Thr Leu Val
                100                 105                 110

Thr Val Ser
        115

<210> SEQ ID NO 11
<211> LENGTH: 18
<212> TYPE: PRT
<213> ORGANISM: Artificial Sequence
<220> FEATURE:
<223> OTHER INFORMATION: MAb316.1 variable region partial sequences
      (light chain)

<400> SEQUENCE: 11

Gln Ile Val Leu Thr Gln Ser Pro Ala Ile Met Ser Ala Ser Pro Gly
  1               5                  10                  15

Glu Lys

<210> SEQ ID NO 12
<211> LENGTH: 26
<212> TYPE: PRT
<213> ORGANISM: Artificial Sequence
<220> FEATURE:
<223> OTHER INFORMATION: MAb316.1 variable region partial sequences
      (light chain)

<400> SEQUENCE: 12

Val Thr Ile Ser Cys Ser Ala Ser Ser Val Ser Tyr Met Tyr Trp
  1               5                  10                  15

Tyr His Gln Lys Pro Gly Ser Ser Pro Lys
             20                  25
```

```
<210> SEQ ID NO 13
<211> LENGTH: 11
<212> TYPE: PRT
<213> ORGANISM: Artificial Sequence
<220> FEATURE:
<223> OTHER INFORMATION: MAb316.1 variable  region partial sequences
      (light chain)

<400> SEQUENCE: 13

Thr Ser Asn Leu Ala Ser Gly Val Pro Ala Arg
1               5                   10

<210> SEQ ID NO 14
<211> LENGTH: 30
<212> TYPE: PRT
<213> ORGANISM: Artificial Sequence
<220> FEATURE:
<223> OTHER INFORMATION: MAb316.1 variable  region partial sequences
      (light chain)

<400> SEQUENCE: 14

Thr Ile Ser Ser Met Glu Ala Glu Asp Ala Ala Thr Tyr Tyr Cys Gln
1               5                   10                  15

Gln Tyr His Ser Tyr Pro Leu Thr Phe Gly Ala Gly Thr Lys
            20                  25                  30

<210> SEQ ID NO 15
<211> LENGTH: 15
<212> TYPE: PRT
<213> ORGANISM: Artificial Sequence
<220> FEATURE:
<223> OTHER INFORMATION: MAb316.1 variable  region partial sequences
      (light chain)

<400> SEQUENCE: 15

Ile Tyr Arg Thr Ser Asn Leu Ala Ser Gly Val Pro Ala Arg Phe
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: MAb316.1 variable  region partial sequences
      (light chain)

<400> SEQUENCE: 16

Arg Thr Ser Asn Leu Ala Ser Gly Val Pro Ala Arg Phe
1               5                   10

<210> SEQ ID NO 17
<211> LENGTH: 17
<212> TYPE: PRT
<213> ORGANISM: Artificial Sequence
<220> FEATURE:
<223> OTHER INFORMATION: MAb316.1 variable  region partial sequences
      (light chain)

<400> SEQUENCE: 17

Ala Ser Gly Val Pro Ala Arg Phe Ser Gly Ser Gly Ser Gly Thr Ser
1               5                   10                  15

Tyr

<210> SEQ ID NO 18
<211> LENGTH: 10
<212> TYPE: PRT
<213> ORGANISM: Artificial Sequence
```

```
<220> FEATURE:
<223> OTHER INFORMATION: MAb316.1 variable region partial sequences
      (light chain)

<400> SEQUENCE: 18

Thr Phe Gly Ala Gly Thr Lys Leu Glu Leu
1               5                   10

<210> SEQ ID NO 19
<211> LENGTH: 19
<212> TYPE: PRT
<213> ORGANISM: Artificial Sequence
<220> FEATURE:
<223> OTHER INFORMATION: MAb316.1 variable region partial sequences
      (heavy chain)

<400> SEQUENCE: 19

Gln Val Gln Leu Gln Gln Ser Gly Pro Glu Leu Val Lys Pro Gly Ala
1               5                   10                  15

Ser Val Lys

<210> SEQ ID NO 20
<211> LENGTH: 15
<212> TYPE: PRT
<213> ORGANISM: Artificial Sequence
<220> FEATURE:
<223> OTHER INFORMATION: MAb316.1 variable region partial sequences
      (heavy chain)

<400> SEQUENCE: 20

Ala Ser Gly Tyr Ser Phe Thr Ser Tyr Tyr Ile His Trp Val Lys
1               5                   10                  15

<210> SEQ ID NO 21
<211> LENGTH: 25
<212> TYPE: PRT
<213> ORGANISM: Artificial Sequence
<220> FEATURE:
<223> OTHER INFORMATION: MAb316.1 variable region partial sequences
      (heavy chain)

<400> SEQUENCE: 21

Gln Arg Pro Gly Gln Gly Leu Glu Trp Ile Gly Trp Ile Tyr Pro Gly
1               5                   10                  15

Ser Tyr Asn Thr Glu Tyr Ser Glu Lys
            20                  25

<210> SEQ ID NO 22
<211> LENGTH: 18
<212> TYPE: PRT
<213> ORGANISM: Artificial Sequence
<220> FEATURE:
<223> OTHER INFORMATION: MAb316.1 variable region partial sequences
      (heavy chain)

<400> SEQUENCE: 22

Met Gln Leu Ser Ser Leu Thr Ser Glu Asp Ser Ala Val Tyr Tyr Cys
1               5                   10                  15

Ala Arg

<210> SEQ ID NO 23
<211> LENGTH: 23
<212> TYPE: PRT
<213> ORGANISM: Artificial Sequence
```

```
<220> FEATURE:
<223> OTHER INFORMATION: MAb316.1 variable region partial sequences
      (heavy chain)

<400> SEQUENCE: 23

Gln Gln Ser Gly Pro Glu Leu Val Lys Pro Gly Ala Ser Val Lys Ile
1               5                   10                  15

Ser Cys Lys Ala Ser Gly Tyr
            20

<210> SEQ ID NO 24
<211> LENGTH: 14
<212> TYPE: PRT
<213> ORGANISM: Artificial Sequence
<220> FEATURE:
<223> OTHER INFORMATION: MAb316.1 variable region partial sequences
      (heavy chain)

<400> SEQUENCE: 24

Val Lys Gln Arg Pro Gly Gln Gly Leu Glu Trp Ile Gly Trp
1               5                   10

<210> SEQ ID NO 25
<211> LENGTH: 12
<212> TYPE: PRT
<213> ORGANISM: Artificial Sequence
<220> FEATURE:
<223> OTHER INFORMATION: MAb316.1 variable region partial sequences
      (heavy chain)

<400> SEQUENCE: 25

Pro Gly Ser Tyr Asn Thr Glu Tyr Ser Glu Lys Phe
1               5                   10

<210> SEQ ID NO 26
<211> LENGTH: 5
<212> TYPE: PRT
<213> ORGANISM: Artificial Sequence
<220> FEATURE:
<223> OTHER INFORMATION: MAb316.1 light chain CDR1 amino acid sequence

<400> SEQUENCE: 26

Ser Ser Val Ser Tyr
1               5

<210> SEQ ID NO 27
<211> LENGTH: 3
<212> TYPE: PRT
<213> ORGANISM: Artificial Sequence
<220> FEATURE:
<223> OTHER INFORMATION: MAb316.1 light chain CDR2 amino acid sequence

<400> SEQUENCE: 27

Arg Thr Ser
1

<210> SEQ ID NO 28
<211> LENGTH: 9
<212> TYPE: PRT
<213> ORGANISM: Artificial Sequence
<220> FEATURE:
<223> OTHER INFORMATION: MAb316.1 light chain CDR3 amino acid sequence

<400> SEQUENCE: 28

Gln Gln Tyr His Ser Tyr Pro Leu Thr
1               5
```

```
<210> SEQ ID NO 29
<211> LENGTH: 8
<212> TYPE: PRT
<213> ORGANISM: Artificial Sequence
<220> FEATURE:
<223> OTHER INFORMATION: MAb316.1 heavy chain CDR1 amino acid sequence

<400> SEQUENCE: 29

Gly Tyr Ser Phe Thr Ser Tyr Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: MAb316.1 heavy chain CDR2 amino acid sequence

<400> SEQUENCE: 30

Ile Tyr Pro Gly Ser Tyr Asn Thr
1               5

<210> SEQ ID NO 31
<211> LENGTH: 9
<212> TYPE: PRT
<213> ORGANISM: Artificial Sequence
<220> FEATURE:
<223> OTHER INFORMATION: MAb316.1 heavy chain CDR3 amino acid sequence

<400> SEQUENCE: 31

Ala Arg Ser Glu Asp Trp Phe Ala Tyr
1               5

<210> SEQ ID NO 32
<211> LENGTH: 748
<212> TYPE: PRT
<213> ORGANISM: Homo sapiens

<400> SEQUENCE: 32

Met Arg Arg Cys Gly Arg Leu Ser Gly Pro Ser Leu Leu Leu Leu
1               5                   10                  15

Leu Leu Leu Leu Ser Pro Leu Leu Phe Ser Gly Pro Gly Ala Tyr Ala
                20                  25                  30

Ala Arg Leu Ser Val Leu Tyr Ser Ser Ser Asp Pro Leu Thr Leu Leu
            35                  40                  45

Asp Ala Asp Ser Val Arg Pro Thr Val Leu Gly Ser Ser Ser Ala Trp
        50                  55                  60

Ala Val Glu Phe Phe Ala Ser Trp Cys Gly His Cys Ile Ala Phe Ala
65                  70                  75                  80

Pro Thr Trp Lys Glu Leu Ala Asn Asp Val Lys Asp Trp Arg Pro Ala
                85                  90                  95

Leu Asn Leu Ala Val Leu Asp Cys Ala Glu Glu Thr Asn Ser Ala Val
            100                 105                 110

Cys Arg Glu Phe Asn Ile Ala Gly Phe Pro Thr Val Arg Phe Phe Gln
        115                 120                 125

Ala Phe Thr Lys Asn Gly Ser Gly Ala Thr Leu Pro Gly Ala Gly Ala
    130                 135                 140

Asn Val Gln Thr Leu Arg Met Arg Leu Ile Asp Ala Leu Glu Ser His
145                 150                 155                 160

Arg Asp Thr Trp Pro Pro Ala Cys Pro Pro Leu Glu Pro Ala Lys Leu
                165                 170                 175
```

```
Asn Asp Ile Asp Gly Phe Phe Thr Arg Asn Lys Ala Asp Tyr Leu Ala
            180                 185                 190
Leu Val Phe Glu Arg Glu Asp Ser Tyr Leu Gly Arg Glu Val Thr Leu
        195                 200                 205
Asp Leu Ser Gln Tyr His Ala Val Ala Val Arg Arg Val Leu Asn Thr
    210                 215                 220
Glu Ser Asp Leu Val Asn Lys Phe Gly Val Thr Asp Phe Pro Ser Cys
225                 230                 235                 240
Tyr Leu Leu Leu Arg Asn Gly Ser Val Ser Arg Val Pro Val Leu Val
                245                 250                 255
Glu Ser Arg Ser Phe Tyr Thr Ser Tyr Leu Arg Gly Leu Pro Gly Leu
            260                 265                 270
Thr Arg Asp Ala Pro Pro Thr Thr Ala Thr Pro Val Thr Ala Asp Lys
        275                 280                 285
Ile Ala Pro Thr Val Trp Lys Phe Ala Asp Arg Ser Lys Ile Tyr Met
    290                 295                 300
Ala Asp Leu Glu Ser Ala Leu His Tyr Ile Leu Arg Val Glu Val Gly
305                 310                 315                 320
Lys Phe Ser Val Leu Glu Gly Gln Arg Leu Val Ala Leu Lys Lys Phe
                325                 330                 335
Val Ala Val Leu Ala Lys Tyr Phe Pro Gly Gln Pro Leu Val Gln Asn
            340                 345                 350
Phe Leu His Ser Ile Asn Asp Trp Leu Gln Lys Gln Lys Lys Arg
        355                 360                 365
Ile Pro Tyr Ser Phe Phe Lys Ala Ala Leu Asp Ser Arg Lys Glu Asp
    370                 375                 380
Ala Val Leu Thr Glu Lys Val Asn Trp Val Gly Cys Gln Gly Ser Glu
385                 390                 395                 400
Pro His Phe Arg Gly Phe Pro Cys Ser Leu Trp Val Leu Phe His Phe
                405                 410                 415
Leu Thr Val Gln Ala Asn Arg Tyr Ser Glu Ala His Pro Gln Glu Pro
            420                 425                 430
Ala Asp Gly Gln Glu Val Leu Gln Ala Met Arg Ser Tyr Val Gln Phe
        435                 440                 445
Phe Phe Gly Cys Arg Asp Cys Ala Asp His Phe Glu Gln Met Ala Ala
    450                 455                 460
Ala Ser Met His Gln Val Arg Ser Pro Ser Asn Ala Ile Leu Trp Leu
465                 470                 475                 480
Trp Thr Ser His Asn Arg Val Asn Ala Arg Leu Ser Gly Ala Leu Ser
                485                 490                 495
Glu Asp Pro His Phe Pro Lys Val Gln Trp Pro Arg Glu Leu Cys
            500                 505                 510
Ser Ala Cys His Asn Glu Leu Asn Gly Gln Val Pro Leu Trp Asp Leu
        515                 520                 525
Gly Ala Thr Leu Asn Phe Leu Lys Ala His Phe Ser Pro Ala Asn Ile
    530                 535                 540
Val Ile Asp Ser Ser Ala Ser Arg His Thr Gly Arg Arg Gly Ser Pro
545                 550                 555                 560
Glu Ala Thr Pro Glu Leu Val Met Asp Thr Leu Lys Leu Glu Ser Arg
                565                 570                 575
Asn Ser Val Leu Gly His Glu Gln Ala Ala Ser Ala Glu Ser Pro Gly
            580                 585                 590
```

-continued

```
Ala Thr Ala Leu Asp Val Pro Ala Glu Lys Pro Glu Ala Ser Gly Pro
            595                 600                 605

Gln Glu Leu Tyr Thr Gly Leu Arg Met Gly Gly Ala Ser Pro Gly Gln
        610                 615                 620

Gly Pro Pro Glu Arg Met Glu Asp His Gln Arg Asp Met Gln Glu Asn
625                 630                 635                 640

Ala Pro Gly Gln Gln His Leu Ser Lys Arg Asp Thr Glu Ala Leu Phe
                645                 650                 655

Leu Pro Glu Val Asn His Leu Gln Gly Pro Leu Glu Leu Arg Arg Gly
            660                 665                 670

Gly Arg Ser Pro Lys Gln Leu Ala Pro Ile Leu Glu Glu Pro Glu
        675                 680                 685

Ala Leu Ala Ile Gln Gly Gln Gly Gln Trp Leu Gln Val Leu Gly Gly
        690                 695                 700

Gly Ile Ser His Leu Asp Ile Ser Leu Cys Val Gly Leu Tyr Ser Val
705                 710                 715                 720

Ser Phe Met Gly Leu Leu Ala Met Tyr Thr Tyr Phe Arg Ala Arg Leu
                725                 730                 735

Arg Thr Pro Lys Gly His Ala Ser Tyr Pro Thr Ala
            740                 745

<210> SEQ ID NO 33
<211> LENGTH: 568
<212> TYPE: PRT
<213> ORGANISM: Homo sapiens

<400> SEQUENCE: 33

Met Arg Arg Cys Gly Arg Leu Ser Gly Pro Pro Ser Leu Leu Leu Leu
1               5                   10                  15

Leu Leu Leu Leu Ser Pro Leu Leu Phe Ser Gly Pro Gly Ala Tyr Ala
            20                  25                  30

Ala Arg Leu Ser Val Leu Tyr Ser Ser Ser Asp Pro Leu Thr Leu Leu
        35                  40                  45

Asp Ala Asp Ser Val Arg Pro Thr Val Leu Gly Ser Ser Ser Ala Trp
    50                  55                  60

Ala Val Glu Phe Phe Ala Ser Trp Cys Gly His Cys Ile Ala Phe Ala
65              70                  75                  80

Pro Thr Trp Lys Glu Leu Ala Asn Asp Val Lys Asp Trp Arg Pro Ala
                85                  90                  95

Leu Asn Leu Ala Val Leu Asp Cys Ala Glu Glu Thr Asn Ser Ala Val
            100                 105                 110

Cys Arg Glu Phe Asn Ile Ala Gly Phe Pro Thr Val Arg Phe Phe Gln
        115                 120                 125

Ala Phe Thr Lys Asn Gly Ser Gly Ala Thr Leu Pro Gly Ala Gly Ala
    130                 135                 140

Asn Val Gln Thr Leu Arg Met Arg Leu Ile Asp Ala Leu Glu Ser His
145                 150                 155                 160

Arg Asp Thr Trp Pro Pro Ala Cys Pro Pro Leu Glu Pro Ala Lys Leu
                165                 170                 175

Asn Asp Ile Asp Gly Phe Phe Thr Arg Asn Lys Ala Asp Tyr Leu Ala
            180                 185                 190

Leu Val Phe Glu Arg Glu Asp Ser Tyr Leu Gly Arg Glu Val Thr Leu
        195                 200                 205

Asp Leu Ser Gln Tyr His Ala Val Ala Val Arg Arg Val Leu Asn Thr
    210                 215                 220
```

```
Glu Ser Asp Leu Val Asn Lys Phe Gly Val Thr Asp Phe Pro Ser Cys
225                 230                 235                 240
Tyr Leu Leu Leu Arg Asn Gly Ser Val Ser Arg Val Pro Val Leu Val
            245                 250                 255
Glu Ser Arg Ser Phe Tyr Thr Ser Tyr Leu Arg Gly Leu Pro Gly Leu
        260                 265                 270
Thr Arg Asp Ala Pro Pro Thr Thr Ala Thr Pro Val Thr Ala Asp Lys
    275                 280                 285
Ile Ala Pro Thr Val Trp Lys Phe Ala Asp Arg Ser Lys Ile Tyr Met
290                 295                 300
Ala Asp Leu Glu Ser Ala Leu His Tyr Ile Leu Arg Val Glu Val Gly
305                 310                 315                 320
Lys Phe Ser Val Leu Glu Gly Gln Arg Leu Val Ala Leu Lys Lys Phe
            325                 330                 335
Val Ala Val Leu Ala Lys Tyr Phe Pro Gly Gln Pro Leu Val Gln Asn
        340                 345                 350
Phe Leu His Ser Ile Asn Asp Trp Leu Gln Lys Gln Lys Lys Arg
    355                 360                 365
Ile Pro Tyr Ser Phe Phe Lys Ala Ala Leu Asp Ser Arg Lys Glu Asp
370                 375                 380
Ala Val Leu Thr Glu Lys Val Asn Trp Val Gly Cys Gln Gly Ser Glu
385                 390                 395                 400
Pro His Phe Arg Gly Phe Pro Cys Ser Leu Trp Val Leu Phe His Phe
            405                 410                 415
Leu Thr Val Gln Ala Asn Arg Tyr Ser Glu Ala His Pro Gln Glu Pro
        420                 425                 430
Ala Asp Gly Gln Glu Val Leu Gln Ala Met Arg Ser Tyr Val Gln Phe
    435                 440                 445
Phe Phe Gly Cys Arg Asp Cys Ala Asp His Phe Glu Gln Met Ala Ala
450                 455                 460
Ala Ser Met His Gln Val Arg Ser Pro Ser Asn Ala Ile Leu Trp Leu
465                 470                 475                 480
Trp Thr Ser His Asn Arg Val Asn Ala Arg Leu Ser Gly Ala Leu Ser
            485                 490                 495
Glu Asp Pro His Phe Pro Lys Val Gln Trp Pro Pro Arg Glu Leu Cys
        500                 505                 510
Ser Ala Cys His Asn Glu Leu Asn Gly Gln Val Pro Leu Trp Asp Leu
    515                 520                 525
Gly Ala Thr Leu Asn Phe Leu Lys Ala His Phe Ser Pro Ala Asn Ile
530                 535                 540
Val Ile Asp Ser Ser Ala Ser Arg His Thr Gly Arg Arg Gly Ser Pro
545                 550                 555                 560
Glu Ala Thr Pro Glu Leu Leu Leu
            565

<210> SEQ ID NO 34
<211> LENGTH: 3399
<212> TYPE: DNA
<213> ORGANISM: Homo sapiens

<400> SEQUENCE: 34
ctcctcctcc tcctccgggg cggaggctgt tggtgcgcgg caggctccgg atactgacta      60
gtcacaaact tgaaggaggt ggacattcaa gccgcctagg atgaggaggt gcggccgcct     120
ctcggggccg ccatcgctgc tgctactact gctgctgctc tcgcctctgc tcttctcggg     180
```

-continued

```
gcccggcgct tacgcggccc ggctctcagt gctctactcg tcctctgacc cgctgacgct    240
gctggatgct gattcggtgc gtcccactgt gctcggctcc agcagcgcct gggcggtgga    300
gttcttcgcc tcctggtgtg gccactgcat cgccttcgcc ccgacgtgga aggagcttgc    360
taacgacgtg aaagactgga ggccagcact caatcttgct gtcctggact gtgctgagga    420
gaccaacagt gctgtctgca gagagttcaa catcgctggc ttcccgactg tgaggttttt    480
tcaggccttt accaagaacg gttctggagc gacactgcca ggtgctggcg ctaatgtgca    540
gactctgcgt atgaggctca tcgatgctct ggagtcccac cgtgacacat ggccccagc    600 ctgtccacct ctggaacctg ccaagctgaa tgatatcgac ggattctttta caagaaataa    660 agcagattac ctggccctgg tctttgaaag ggaagactcc tacctgggta gagaggtaac    720
tctggacctg tcccagtacc atgctgtggc agtgcgcagg gtcttgaata cagagagtga    780
cctggtgaac aagtttggcg tcactgactt cccatcttgt tacctgctgc ttcggaatgg    840
ctctgtctcc cgagtgcctg tgctggtgga gtccaggtct ttctatacat cctatcttcg    900
ggggctacct ggactgacca gggatgctcc cccaaccaca gccaccccag tcactgctga    960
taagatagca cccacagtgt ggaagtttgc agaccgctcc aagatctaca tggccgacct   1020
ggagtccgca ctccactaca tcttgcgtgt agaagtgggg aagttctcag tgctggaggg   1080
acagcgcctg gtggccctga aaagtttgt ggcagtattg ccaagtact ccctgggca    1140 gcctttggtc cagaacttct tgcattccat aaacgactgg cttcagaagc agcagaagaa   1200
gaggatcccc tacagtttct tcaaagctgc tctggacagc aggaaggagg atgctgtcct   1260
tactgagaag gtgaactggg tcggctgcca gggcagtgag ccacacttcc ggggg tttcc   1320 ctgctcactg tgggtcctct tccacttcct gacggtgcag gcaaaccgat atagtgaggc   1380
ccacccacag gaaccagctg atggccagga ggtcctccaa gccatgagga gctatgttca   1440
gttcttcttt ggctgtcgtg actgtgcgga ccattttgag cagatggctg cagcgtccat   1500
gcaccaagtg agaagtccca gtaatgcgat tctttggctc tggactagcc acaacagggt   1560
taacgctcgc ctctcaggtg ctctgagtga ggaccccac ttccccaagg tgcagtggcc   1620
tccccgtgag ctgtgttctg cctgccataa tgaactcaac ggacaggtgc ctttgtggga   1680
ccttggtgcc acccctcaact ttctcaaggc tcacttctcc ccagcaaaca tcgtcataga   1740
ctcttctgca tctagacaca caggccggag agggagtcca aagctaccc ccgagctggt   1800 aatggataca ttaaaactgg agagcagaaa ttcagtgttg ggccatgagc aggctgcttc   1860
tgcagagtcc cctggagcca ctgccctaga tgtaccagct gagaagcctg aagcaagtgg   1920 ccccaagaa ctatacacag gcctcagaat gggtggagct tcaccagggc agggccctcc   1980
tgagcgcatg gaagaccacc agagggatat gcaggagaat gccccgggc agcaacactt   2040 gagcaagaga gacactgaag ccttatttct gcctgaggtg aaccacctcc aaggccctt    2100 agagctcagg cgagggggcc gcagcccaa gcaactagcc cccatacttg aagaggaacc   2160
agaggcccta gctatacagg gccaaggcca gtggctgcag gttctaggag ggggcatttc   2220
ccacctggac attagcctct gtgtggggct ctactccgtg tccttcatgg cttactggc    2280 catgtacacc tactttcggg ccaggctgag aaccccaaag gccatgcta gttaccccac    2340 agcctgaact gcctcggcag aggacagaca aggagctgct gatgtctggg ctttgggtt    2400 ttttttttt ttttttggcc cactggcccc cttgcttcct ttctacccct tgttctgttg    2460
tctagcttag gagagtggca agtccaagaa agtgagttgt ttcagtgaac cctggagtct   2520
actgtgagag gattccctag acaaaacaga atcagggtgc cagtctcgcc tgaccagcat   2580
```

```
ggggtaggag cagcctgacg caggggctca ggaggcttct ggaggctca ggccctggct    2640
tcagcaccaa attctgtttt tcagctcttg tgaagtcctg ccccattcct gctgaagtct    2700
caatgtgtcc tgcttggtct tggccttaga ttgaggcaga caagtccaga gtttccaagg    2760
tttctcatcc agaggagtgt atgtgggccg ggtgggctgg agtggacctc ctcactgcat    2820
tctgagactg tctactcccc tccctcacga catgaagaaa aagcatccct ccggccttct    2880
ctggcctggc cagcttcagc acctcaggag tgggtggggc ttagcttcaa gaatgggtct    2940
gggagcctca gaaatgatt ctggtcaccc aggttcaaac tggggtttct gctgcaagag    3000
tgtggtttgg caggctggga gggtgacagt tgctgcactg tagggtgtag tgcttgcttg    3060
gtggtagggg caaggggggtg ggtgatgctg gggtctgtag tgccttagtc ctgggctagc    3120
tgggagaggg cagactcctc tctgagcggg ggtgcttgtc tcttactttg gtctctaaaa    3180
tcaatgctaa ctttggggtg tggaaggtgc tgggtttagg gcagtgggca gagccctctc    3240
tctcccgctt gggtccactg tgggcaggag gggtggaga gaccagccca catttccttc     3300
ccctgctcct gtggcttggg agggatgtgg aataaaatta tttttgttaa gtcacgcaga    3360
aaaaaaaaaa aaaaaaaaaa aaaaaaaaaa aaaaaaaa                             3399

<210> SEQ ID NO 35
<211> LENGTH: 2533
<212> TYPE: DNA
<213> ORGANISM: Homo sapiens

<400> SEQUENCE: 35
ctcctcctcc tcctccgggg cggaggctgt tggtgcgcgg caggctccgg atactgacta      60
gtcacaaact tgaaggaggt ggacattcaa gccgcctagg atgaggaggt gcggccgcct     120
ctcggggccg ccatcgctgc tgctactact gctgctgctc tcgcctctgc tcttctcggg    180
gcccggcgct tacgcggccc ggctctcagt gctctactcg tcctctgacc cgctgacgct    240
gctggatgct gattcggtgc gtcccactgt gctcggctcc agcagcgcct gggcggtgga    300
gttcttcgcc tcctggtgtg gccactgcat cgccttcgcc ccgacgtgga aggagcttgc    360
taacgacgtg aaagactgga ggccagcact caatcttgct gtcctggact gtgctgagga    420
gaccaacagt gctgtctgca gagagttcaa catcgctggc ttcccgactg tgaggttttt    480
tcaggccttt accaagaacg gttctggagc gacactgcca ggtgctggcg ctaatgtgca    540
gactctgcgt atgaggctca tcgatgctct ggagtcccac cgtgacacat ggccccagc     600
ctgtccacct ctggaacctg ccaagctgaa tgatatcgac ggattcttta caagaaataa    660
agcagattac ctggccctgg tctttgaaag ggaagactcc tacctgggta gagaggtaac    720
tctggacctg tccagtacc atgctgtggc agtgcgcagg gtcttgaata cagagagtga    780
cctggtgaac aagtttggcg tcactgactt cccatcttgt tacctgctgc ttcggaatgg    840
ctctgtctcc cgagtgcctg tgctggtgga gtccaggtct ttctatacat cctatcttcg    900
ggggctacct ggactgacca gggatgctcc cccaaccaca gccaccccag tcactgctga    960
taagatagca cccacagtgt ggaagtttgc agaccgctcc aagatctaca tggccgacct    1020
ggagtccgca ctccactaca tcttgcgtgt agaagtgggg aagttctcag tgctggaggg    1080
acagcgcctg gtggccctga aaagtttgt ggcagtattg gccaagtact ccctgggca     1140
gcctttggtc cagaacttct tgcattccat aaacgactgg cttcagaagc agcagaagaa    1200
gaggatcccc tacagtttct tcaaagctgc tctggacagc aggaaggagg atgctgtcct    1260
tactgagaag gtgaactggg tcggctgcca gggcagtgag ccacacttcc ggggtttcc     1320
```

```
ctgctcactg tgggtcctct tccacttcct gacggtgcag gcaaaccgat atagtgaggc    1380
ccacccacag gaaccagctg atggccagga ggtcctccaa gccatgagga gctatgttca    1440
gttcttcttt ggctgtcgtg actgtgcgga ccattttgag cagatggctg cagcgtccat    1500
gcaccaagtg agaagtccca gtaatgcgat tctttggctc tggactagcc acaacagggt    1560
taacgctcgc ctctcaggtg ctctgagtga ggaccccac  ttccccaagg tgcagtggcc    1620
tccccgtgag ctgtgttctg cctgccataa tgaactcaac ggacaggtgc ctttgtggga    1680
ccttggtgcc accctcaact ttctcaaggc tcacttctcc ccagcaaaca tcgtcataga    1740
ctcttctgca tctagacaca caggccgag  agggagtcca gaagctaccc ccgagctgct    1800
cttgtgaagt cctgccccat tcctgctgaa gtctcaatgt gtcctgcttg gtcttggcct    1860
tagattgagg cagacaagtc cagagtttcc aaggtttctc atccagagga gtgtatgtgg    1920
gccgggtggg ctggagtgga cctcctcact gcattctgag actgtctact cccctccctc    1980
acgacatgaa gaaaaagcat ccctccggcc ttctctggcc tggccagctt cagcacctca    2040
ggagtgggtg gggcttagct tcaagaatgg gtctgggagc tcagaaaat  gattctggtc    2100
acccaggttc aaactggggt ttctgctgca agagtgtggt ttggcaggct gggagggtga    2160
cagttgctgc actgtagggt gtagtgcttg cttggtggta ggggcaaggg ggtgggtgat    2220
gctggggtct gtagtgcctt agtcctgggc tagctgggag agggcagact cctctctgag    2280
cggggggtgct tgtctcttac tttggtctct aaaatcaatg ctaactttgg ggtgtggaag    2340
gtgctgggtt tagggcagtg ggcagagccc tctctctccc gcttgggtcc actgtgggca    2400
ggaggggtg  gagagaccag cccacatttc cttcccctgc tcctgtggct tgggagggat    2460
gtggaataaa attattttg  ttaagtcacg cagaaaaaaa aaaaaaaaa  aaaaaaaaa     2520
aaaaaaaaaa aaa                                                      2533
```

<210> SEQ ID NO 36
<211> LENGTH: 107
<212> TYPE: PRT
<213> ORGANISM: Artificial Sequence
<220> FEATURE:
<223> OTHER INFORMATION: MAb492.1 variable light amino acid sequence

<400> SEQUENCE: 36

```
Asp Val Val Met Thr Gln Thr His Lys Phe Met Ser Thr Ser Val Gly
1               5                   10                  15
Asp Arg Val Ser Ile Thr Cys Lys Ala Ser Gln Asp Val Ser Thr Ala
            20                  25                  30
Val Ala Trp Tyr Gln Gln Lys Ser Gly Gln Ser Pro Lys Leu Leu Ile
        35                  40                  45
His Ser Ala Ser Tyr Arg Tyr Thr Gly Val Pro Asp Arg Phe Thr Gly
    50                  55                  60
Ser Gly Ser Gly Thr Asp Phe Thr Phe Thr Ile Ser Ser Val Gln Ala
65                  70                  75                  80
Glu Asp Leu Ala Val Tyr Tyr Cys Gln Gln His Tyr Ser Ile Pro Leu
                85                  90                  95
Thr Phe Gly Ala Gly Thr Lys Leu Glu Leu Lys
            100                 105
```

<210> SEQ ID NO 37
<211> LENGTH: 118
<212> TYPE: PRT
<213> ORGANISM: Artificial Sequence

```
<220> FEATURE:
<223> OTHER INFORMATION: MAb492.1 variable heavy amino acid sequence

<400> SEQUENCE: 37

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Ser Pro Gly Lys Gly Leu Glu Trp Leu
        35                  40                  45

Gly Met Ile Trp Gly Asp Gly Arg Thr Asp Tyr Lys Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Arg Tyr Phe Cys Ala
                85                  90                  95

Ser Asp Tyr Tyr Gly Ser Gly Ser Phe Ala Tyr Trp Gly Gln Gly Thr
            100                 105                 110

Leu Val Thr Val Ser Ala
        115

<210> SEQ ID NO 38
<211> LENGTH: 6
<212> TYPE: PRT
<213> ORGANISM: Artificial Sequence
<220> FEATURE:
<223> OTHER INFORMATION: MAb492.1 light chain CDR1 amino acid sequence

<400> SEQUENCE: 38

Gln Asp Val Ser Thr Ala
1               5

<210> SEQ ID NO 39
<211> LENGTH: 3
<212> TYPE: PRT
<213> ORGANISM: Artificial Sequence
<220> FEATURE:
<223> OTHER INFORMATION: MAb492.1 light chain CDR2 amino acid sequence

<400> SEQUENCE: 39

Ser Ala Ser
1

<210> SEQ ID NO 40
<211> LENGTH: 9
<212> TYPE: PRT
<213> ORGANISM: Artificial Sequence
<220> FEATURE:
<223> OTHER INFORMATION: MAb492.1 light chain CDR3 amino acid sequence

<400> SEQUENCE: 40

Gln Gln His Tyr Ser Ile Pro Leu Thr
1               5

<210> SEQ ID NO 41
<211> LENGTH: 8
<212> TYPE: PRT
<213> ORGANISM: Artificial Sequence
<220> FEATURE:
<223> OTHER INFORMATION: MAb492.1 heavy chain CDR1 amino acid sequence
```

```
<400> SEQUENCE: 41

Gly Phe Ser Leu Thr Gly Tyr Gly
1               5

<210> SEQ ID NO 42
<211> LENGTH: 7
<212> TYPE: PRT
<213> ORGANISM: Artificial Sequence
<220> FEATURE:
<223> OTHER INFORMATION: MAb492.1 heavy chain CDR2 amino acid sequence

<400> SEQUENCE: 42

Ile Trp Gly Asp Gly Arg Thr
1               5

<210> SEQ ID NO 43
<211> LENGTH: 12
<212> TYPE: PRT
<213> ORGANISM: Artificial Sequence
<220> FEATURE:
<223> OTHER INFORMATION: MAb492.1 heavy chain CDR3 amino acid sequence

<400> SEQUENCE: 43

Ala Ser Asp Tyr Tyr Gly Ser Gly Ser Phe Ala Tyr
1               5                   10

<210> SEQ ID NO 44
<211> LENGTH: 107
<212> TYPE: PRT
<213> ORGANISM: Artificial Sequence
<220> FEATURE:
<223> OTHER INFORMATION: MAb492.1gen variable light AA sequence

<400> SEQUENCE: 44

Asp Val Val Met Thr Gln Thr His Lys Phe Met Ser Thr Ser Val Gly
1               5                   10                  15

Asp Arg Val Ser Ile Thr Cys Lys Ala Ser Gln Asp Val Ser Gly Ala
            20                  25                  30

Val Ala Trp Tyr Gln Gln Lys Ser Gly Gln Ser Pro Lys Leu Leu Ile
        35                  40                  45

Ser Met Ala Ser Gln Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ala Ile Pro Leu
                85                  90                  95

Thr Phe Gly Ala Gly Thr Lys Leu Glu Leu Lys
            100                 105

<210> SEQ ID NO 45
<211> LENGTH: 118
<212> TYPE: PRT
<213> ORGANISM: Artificial Sequence
<220> FEATURE:
<223> OTHER INFORMATION: MAb492.1gen variable heavy AA sequence

<400> SEQUENCE: 45

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30
```

```
Ser Val Ile Trp Val Arg Gln Ser Pro Gly Lys Gly Leu Glu Trp Leu
            35                  40                  45

Gly Met Ile Trp Gly Asp Gly Arg Thr Glu Tyr Lys Ser Ala Leu Lys
 50                  55                  60

Ser Arg Leu Ser Ile Thr Lys Asp Asn Ser Lys Ser Gln Val Phe Leu
 65                  70                  75                  80

Lys Met Asn Ser Leu Gln Thr Asp Asp Thr Ala Arg Tyr Phe Cys Ala
                 85                  90                  95

Ser Asp Ser Met Asp Pro Gly Ser Phe Ala Tyr Trp Gly Gln Gly Thr
            100                 105                 110

Leu Val Thr Val Ser Ala
        115

<210> SEQ ID NO 46
<211> LENGTH: 6
<212> TYPE: PRT
<213> ORGANISM: Artificial Sequence
<220> FEATURE:
<223> OTHER INFORMATION: MAb492.1gen light chain CDR1 AA sequence

<400> SEQUENCE: 46

Gln Asp Val Ser Gly Ala
 1               5

<210> SEQ ID NO 47
<211> LENGTH: 3
<212> TYPE: PRT
<213> ORGANISM: Artificial Sequence
<220> FEATURE:
<223> OTHER INFORMATION: MAb492.1gen light chain CDR2 AA sequence

<400> SEQUENCE: 47

Met Ala Ser
 1

<210> SEQ ID NO 48
<211> LENGTH: 9
<212> TYPE: PRT
<213> ORGANISM: Artificial Sequence
<220> FEATURE:
<223> OTHER INFORMATION: MAb492.1gen light chain CDR3 AA sequence

<400> SEQUENCE: 48

Gln Gln His Tyr Ala Ile Pro Leu Thr
 1               5

<210> SEQ ID NO 49
<211> LENGTH: 8
<212> TYPE: PRT
<213> ORGANISM: Artificial Sequence
<220> FEATURE:
<223> OTHER INFORMATION: MAb492.1gen heavy chain CDR1 AA sequence

<400> SEQUENCE: 49

Gly Phe Ser Leu Thr Gly Tyr Ser
 1               5

<210> SEQ ID NO 50
<211> LENGTH: 7
<212> TYPE: PRT
<213> ORGANISM: Artificial Sequence
<220> FEATURE:
<223> OTHER INFORMATION: MAb492.1gen heavy chain CDR2 AA sequence
```

```
<400> SEQUENCE: 50

Ile Trp Gly Asp Gly Arg Thr
1               5

<210> SEQ ID NO 51
<211> LENGTH: 12
<212> TYPE: PRT
<213> ORGANISM: Artificial Sequence
<220> FEATURE:
<223> OTHER INFORMATION: MAb492.1gen heavy chain CDR3 AA sequence

<400> SEQUENCE: 51

Ala Ser Asp Ser Met Asp Pro Gly Ser Phe Ala Tyr
1               5                   10
```

ANTIBODIES TARGETING QUIESCIN SULFHYDRYL OXIDASE (QSOX1) AND USES OF SAME

RELATED APPLICATIONS

This application is a Continuation of PCT Patent Application No. PCT/IL2016/051147 having International filing date of Oct. 25, 2016, which claims the benefit of priority under 35 USC § 119(e) of U.S. Provisional Patent Application No. 62/246,076 filed on Oct. 25, 2015. The contents of the above applications are all incorporated by reference as if fully set forth herein in their entirety.

SEQUENCE LISTING STATEMENT

The ASCII file, entitled 73147SequenceListing.txt, created on Apr. 25, 2018, comprising 77,398 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to antibodies targeting QSOX1 including cross-species-specific antibodies, and, more particularly, but not exclusively, to the generation and use of same.

Monoclonal antibody therapy has become an integral part of cancer diagnostics and treatment. The success of antibody-based therapy stems from the high specificity and affinity that antibodies offer compared to other anti-tumor agents. In addition, tumors express on their cell-surfaces many potential targets for antibody therapeutics. Antibodies supplied extracellularly can both neutralize the function of their cell-surface antigen and recruit the immune system for a more extensive anti-tumor response. Recently, the realization that tumor stroma has a major role in supporting tumor development and metastasis inspired antibody-based cancer therapies targeting extracellular matrix (ECM) components in addition to targeting tumor cells directly. Examples for such agents are antibodies that affect the extracellular glycoprotein tenascin or fibroblast activation protein, found in stromal fibroblasts of most human carcinomas.

ECM proteins are good candidates for antibody therapy because they are both accessible and abundant in most tissues, making the same ECM components a target in various cancers. A major component of the ECM that is over-expressed, reorganized, and cross-linked in tumorigenesis is collagen. Collagen cross-linking by the enzyme lysyl oxidase (LOX) is increased in several cancers and contributes to matrix stiffening, thereby promoting cell adhesion and migration. Inhibitors of LOX activity, including monoclonal antibodies, significantly inhibited tumor growth and metastasis in gastric carcinoma. Laminin is another abundant scaffolding ECM protein that interacts with integrins to mediate cell adhesion and migration, a requirement for metastasis. Indeed, laminin is over-expressed in various cancers, and its chain isotypes serve as tumor biomarkers. Like collagen cross-linking and integrin blocking, laminin incorporation into the matrix may serve as a complementary target for antibody-based cancer therapeutics.

Fass D. and co-workers have recently shown that laminin incorporation into the ECM is affected by the disulfide catalyst Quiescin sulfhydryl oxidase 1 (QSOX1) [Ilani, T. et al. (2013) *Science* 341: 74-76]. The enzyme QSOX1 is a fusion of two thioredoxin (Trx) domains and an Erv-fold sulfhydryl oxidase module (FIG. 1A). QSOX1 contains two CXXC motifs as redox-active sites that cooperate to relay electrons from reduced thiols of substrate proteins to molecular oxygen. Mechanistically, after oxidizing the substrate, the Trx active site transfers two electrons to the Erv CXXC motif through an inter-domain disulfide intermediate (FIG. 1C). The electrons proceed to the adjacent flavin adenine dinucleotide cofactor, which in turn reduces oxygen to hydrogen peroxide, leaving QSOX1 oxidized and ready for another catalytic cycle. Unlike other disulfide catalysts, QSOX1 is localized downstream of the endoplasmic reticulum (ER). It is found in the Golgi apparatus and secreted from quiescent fibroblasts into the ECM, where it affects ECM composition and especially laminin incorporation [Ilani T. et al. (2013), supra]. Specifically, QSOX1 affects the incorporation of laminin isoforms that contain an α4 chain [Ilani T. et al. (2013), supra], a known marker for tumor progression. Together with the over-production of QSOX1 in various adenocarcinomas and associated stroma, these findings point to a possible role of QSOX1 in stimulating tumor cell migration via laminin incorporation.

The multi-step catalytic cycle of QSOX1 implies that obscuring any one of several sites on the protein by interaction with antibody may accomplish inhibition. Fass D. and co-workers have developed an inhibitory monoclonal antibody, MAb492.1, which blocks substrate access to the Trx CXXC redox-active site of human QSOX1 (HsQSOX1) (FIG. 1B) [Grossman I. et al. (2013) *J. Mol. Biol.* 425: 4366-4378]. MAb492.1 efficiently inhibited HsQSOX1 activity, and consequently inhibited adhesion and migration of cancer cells to and through fibroblasts from corresponding tissues [Ilani T. et al. (2013), supra]. Accordingly, MAb492.1 may serve as an anti-metastatic drug in antibody-based cancer therapy.

In certain cases an antibody targeting a human protein is sufficient for pre-clinical trials in animal models due to the availability of xenograft and tumor graft models. However, a major disadvantage of these models is the artificial interaction of the tumor with surrounding tissues. Moreover, eventual recruitment of mouse fibroblasts will create an inhomogeneous tumor microenvironment composed of both mouse and human constituents. Hence, when targeting a secreted protein such as QSOX1, mouse models with a natural organization of murine cancer cells and stroma, such as genetically modified mice that develop spontaneous tumors, may be preferable for studying metastasis development. In such configurations, when targeting an endogenous animal protein, the lead compound e.g., antibody which recognizes the human protein, is often irrelevant.

U.S. Patent Application no. 20140141015 (to Lake and Katchman) discloses tumor treatment by administering an inhibitor of QSOX1, e.g., an antibody. Specifically, U.S. 20140141015 discloses the use of QSOX1 inhibitors for the treatment of tumors that over-express QSOX1, e.g., pancreatic ductal adenocarcinoma (PDA) and breast adenocarcinoma.

Additional background art includes PCT publication nos. WO 2013/132495 (to Fass et al.), WO 2010/077921 (to Lake et al.) and WO 2010/071787 (to Lake et al.).

SUMMARY OF THE INVENTION

According to an aspect of some embodiments of the present invention there is provided an antibody comprising an antigen recognition domain exhibiting species cross reactivity to human QSOX1 and murine QSOX1.

According to an aspect of some embodiments of the present invention there is provided an antibody comprising an antigen recognition domain exhibiting species cross reactivity to human QSOX1 and murine QSOX1, the antigen recognition domain comprising complementarity determining regions (CDRs) as set forth in SEQ ID NOs: 46-51.

According to an aspect of some embodiments of the present invention there is provided a pharmaceutical composition comprising as an active ingredient the antibody of some embodiments of the invention and a pharmaceutically acceptable carrier.

According to an aspect of some embodiments of the present invention there is provided a method for preventing or treating a laminin-associated disease or condition in a subject in need thereof, the method comprising administering to the subject a therapeutically effective amount of the pharmaceutical composition of some embodiments of the invention.

According to an aspect of some embodiments of the present invention there is provided a use of the antibody of some embodiments of the invention for the manufacture of a medicament identified for preventing or treating a laminin-associated disease or condition in a subject in need thereof.

According to an aspect of some embodiments of the present invention there is provided an article of manufacture comprising the antibody of some embodiments of the invention being packaged in a packaging material and identified in print, in or on the packaging material for use in the treatment of a laminin-associated disease or condition.

According to an aspect of some embodiments of the present invention there is provided an antibody comprising an antigen recognition domain comprising CDRs as set forth in SEQ ID NOs: 26-31, wherein the antibody specifically binds murine QSOX1.

According to an aspect of some embodiments of the present invention there is provided a method for in vivo determining the efficiency of an antibody in reducing a laminin-associated disease or condition in a murine animal, the method comprising administering to the murine animal the antibody of some embodiments of the invention and monitoring progression of a laminin-associated disease or condition in the murine animal, thereby determining the efficiency of the antibody.

According to an aspect of some embodiments of the present invention there is provided an isolated polynucleotide comprising a nucleic acid sequence encoding the antibody of some embodiments of the invention.

According to an aspect of some embodiments of the present invention there is provided an isolated polynucleotide comprising a nucleic acid sequence encoding an antibody comprising the CDRs set forth in SEQ ID NOs: 46-51.

According to an aspect of some embodiments of the present invention there is provided an isolated polynucleotide comprising a nucleic acid sequence encoding an antibody comprising the CDRs set forth in SEQ ID NOs: 26-31.

According to an aspect of some embodiments of the present invention there is provided a method of producing an antibody which comprises an antigen recognition domain exhibiting species cross reactivity to QSOX1, the method comprising: (a) introducing at least one point mutation in the antigen binding domain of an antibody which binds QSOX1 of a first species, which the at least one point mutation increases the water-mediated hydrogen bonding in the interaction interface between the antigen binding domain of the antibody and the QSOX1 of the first species, and alternatively or additionally the at least one point mutation reduces aromatic interactions between the antigen binding domain of the antibody and the QSOX1 of the first species, wherein the at least one point mutation does not substantially affect affinity of the antibody to the QSOX1 of the first species; and (b) testing binding of the antibody having the at least one point mutation to QSOX1 of a second species, wherein when the antibody having the at least one point mutation binds the QSOX1 of the first species and the second species with substantially the same affinity the antibody is considered having cross reactivity to QSOX1.

According to some embodiments of the invention, the antibody comprises a lower content of aromatic amino acids in CDRs of the antigen recognition domain as compared to that of a species-specific antibody to the human QSOX1.

According to some embodiments of the invention, the aromatic amino acids comprise tyrosine.

According to some embodiments of the invention, the antibody comprises at least one charged amino acid in CDR3 of a variable heavy chain of the antibody.

According to some embodiments of the invention, the charged amino acid comprises aspartic acid.

According to some embodiments of the invention, the antibody inhibits QSOX1 activity in mediating laminin incorporation in the basement membrane.

According to some embodiments of the invention, the activity is assayed by at least one of an immunofluorescence (IF) staining assay of the extracellular matrix or western blot assay detecting for soluble laminin.

According to some embodiments of the invention, the antibody is an antibody fragment.

According to some embodiments of the invention, the antibody is selected from the group consisting of a Fab fragment, an Fv fragment, a single chain antibody and a single domain antibody.

According to some embodiments of the invention, the antibody is a monoclonal antibody.

According to some embodiments of the invention, the monoclonal antibody is MAb492gen and comprises CDRs SEQ ID NOs: 46-51.

According to some embodiments of the invention, the antibody is a single chain antibody.

According to some embodiments of the invention, the single chain antibody is scFV492gen and comprises CDRs SEQ ID NOs: 46-51.

According to some embodiments of the invention, the antibody is humanized.

According to some embodiments of the invention, the antibody is a chimeric antibody.

According to some embodiments of the invention, the antibody is immobilized to a solid support.

According to some embodiments of the invention, the antibody is attached to a detectable moiety.

According to some embodiments of the invention, the antibody comprises an amino acid sequence as set forth in SEQ ID NOs: 44 and 45.

According to some embodiments of the invention, the method further comprises administering to the subject a chemotherapeutic agent.

According to some embodiments of the invention, the use further comprises the use of a chemotherapeutic agent.

According to some embodiments of the invention, the article of manufacture further comprises a chemotherapeutic agent.

According to some embodiments of the invention, the laminin-associated disease or condition is a tumor.

According to some embodiments of the invention, the tumor is a metastasizing solid tumor.

According to some embodiments of the invention, the tumor is an adenocarcinoma.

According to some embodiments of the invention, the tumor is a cancer selected from the group consisting of a prostate cancer, a lung cancer, a breast cancer, a cervical cancer, an urachus cancer, a vaginal cancer, a colon cancer, an esophagus cancer, a pancreatic cancer, a throat cancer, a stomach cancer and a myeloid leukemia.

According to some embodiments of the invention, the laminin-associated disease or condition is associated with fibrosis.

According to some embodiments of the invention, the amino acid sequence is as set forth in SEQ ID NOs: 9 and 10.

According to some embodiments of the invention, the antibody is a monoclonal antibody.

According to some embodiments of the invention, the at least one point mutation is in a CDR sequence of the antibody.

According to some embodiments of the invention, the at least one point mutation which reduces aromatic interactions is in a tyrosine.

According to some embodiments of the invention, the at least one point mutation which reduces aromatic interactions comprises an amino acid comprising a flexible side chain.

According to some embodiments of the invention, the at least one point mutation which increases the water-mediated hydrogen bonding comprises at least one charged amino acid.

According to some embodiments of the invention, the at least one point mutation which increases the water-mediated hydrogen bonding is an aspartic acid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B are schematic illustrations of QSOX1 domain organization and inhibition by MAb492.1. FIG. 1A shows that the two modules of mammalian QSOX1 enzymes are linked by a flexible linker (black). The amino-terminal module, $QSOX1_{Trx}$ is composed of two Trx-fold domains, the first of which has a redox-active CXXC motif (yellow balls). A second redox-active CXXC motif is located in the carboxy-terminal Erv domain. This domain binds an FAD cofactor (fused hexagons). The domain labeled ψErv is a degenerate Erv domain lacking active-site cysteines and a FAD cofactor; and FIG. 1B shows the surface presentation of a complex of a Fab fragment of Mab492.1 (Fab492.1) and $HsQSOX1_{Trx}$ (PDB code: 4IJ3) showing that Fab492.1 inhibits HsQSOX1 by burying the Trx CXXC active site (yellow spheres).

Figure 1C:
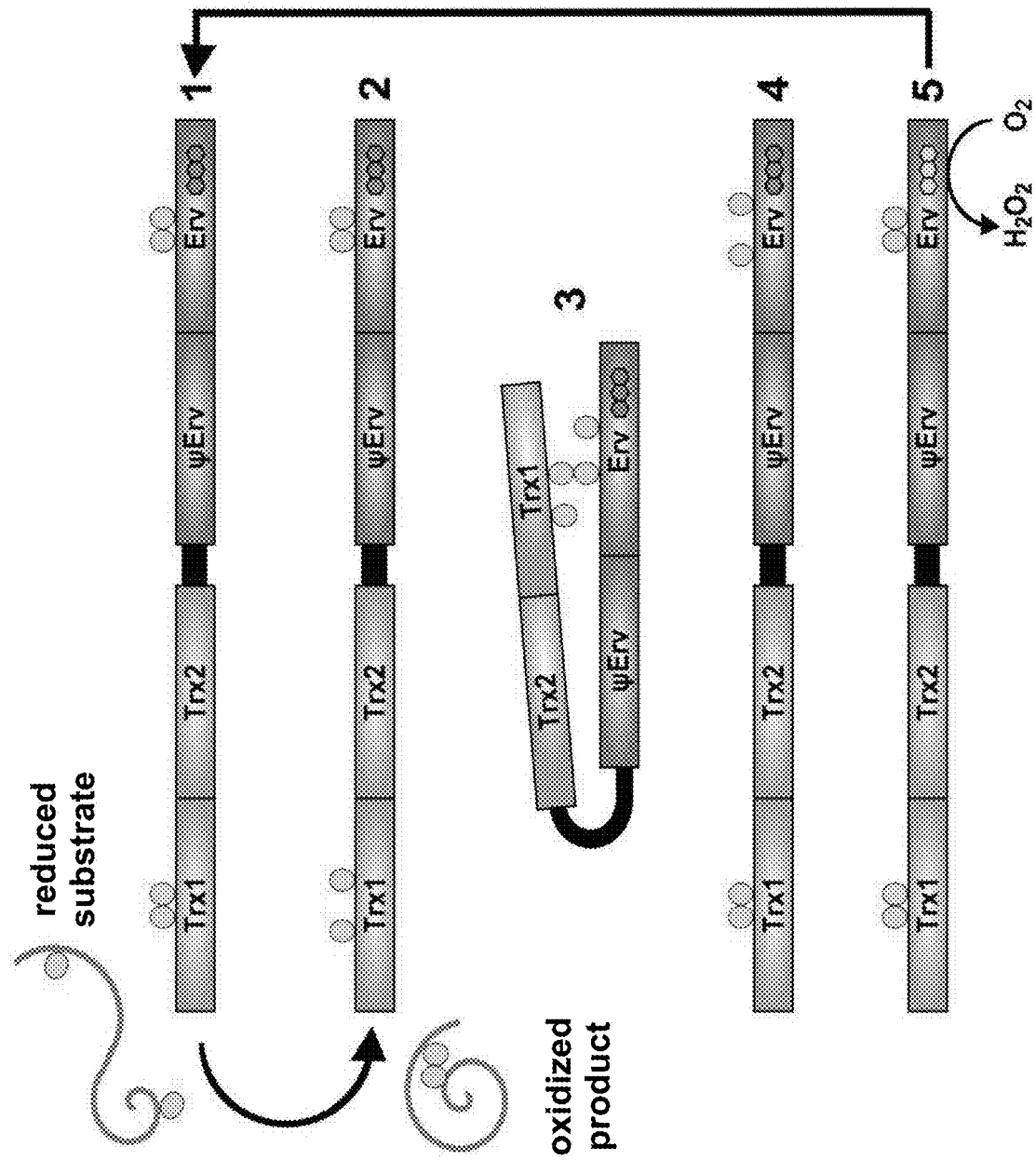

FIG. 1C is a schematic illustration of the catalytic cycle of QSOX1 oxidizing two free thiols in a substrate molecule to a disulfide bond, and reducing oxygen to hydrogen peroxide. Different chemical enzyme states in the cycle are designated with numbers 1-5. In state 3, an inter-domain disulfide requires a conformational change that leads to physical proximity of the two CXXC motifs. Fused yellow balls represent disulfide bonds. Separated yellow balls indicate reduced cysteines. Orange FAD hexagons represent oxidized FAD, whereas yellow hexagons indicate reduced FAD.

FIGS. 2A-D illustrate that MAb492.1 is species specific. FIG. 2A shows the turnover numbers of various mammalian QSOX1 enzymes in the absence and presence of 250 nM or 1 μM MAb492.1. Activity was evaluated using an oxygen consumption assay; FIG. 2B shows the sequence alignment of HsQSOX1 and other mammalian QSOX1 orthologs in the region bound by MAb492.1. Residues involved in interactions with MAb492.1 are indicated in bold. Residues from MmQSOX1, RnQSOX1, and CpQSOX1 that differ from the corresponding HsQSOX1 residues are colored red; FIG. 2C shows superposition of the Fab492.1-$HsQSOX1_{Trx}$ complex structure (PDB code: 4IJ3) and the structure of $MmQSOX1_{Trx}$ (PDB code: 5D8I). The two chains of $MmQSOX1_{Trx}$ from the crystal asymmetric unit are light (chain B) and dark (chain A) gray, and $HsQSOX1_{Trx}$ is pink. Right, close-up of the expected clash between CDR H3 and residues TLPG(138-141) from MmQSOX1. Left, close-up of the expected clash between CDR L3 and Asn117 from MmQSOX1. Only chain B of $MmQSOX1_{Trx}$ is shown for simplicity; and FIG. 2D shows the percent activity for different MmQSOX1 mutants in the presence of MAb492.1. Oxygen consumption measurements were conducted with 100 nM enzyme, 250 nM MAb492.1, and 200 μM DTT. Percent activity was calculated according to the results of the same measurements in the absence of antibody. Error bars represent standard deviations from an average of three measurements.

Figure 3F:
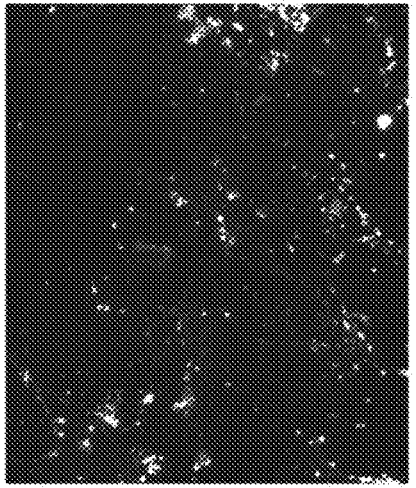
Figure 3E:
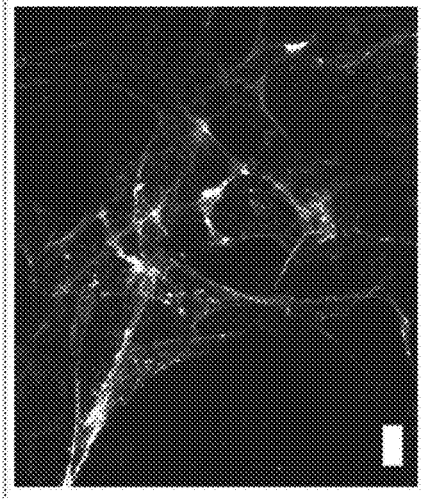
Figure 3H:
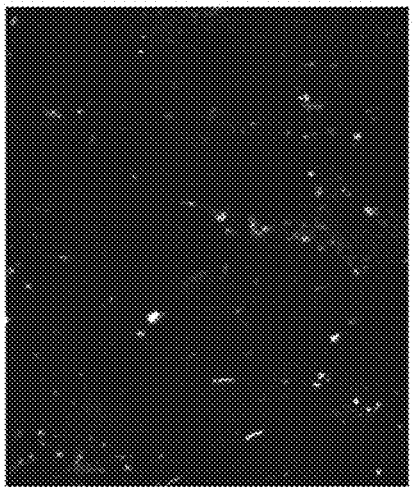
Figure 3G:
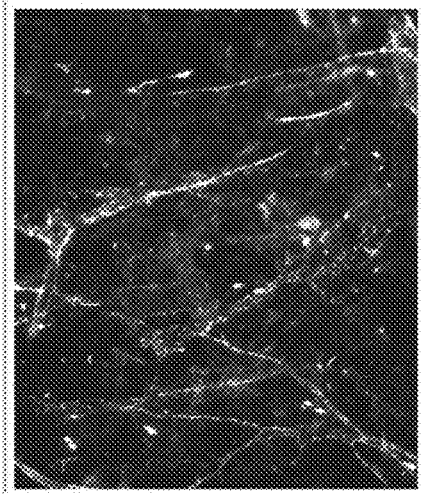
Figure 3D:
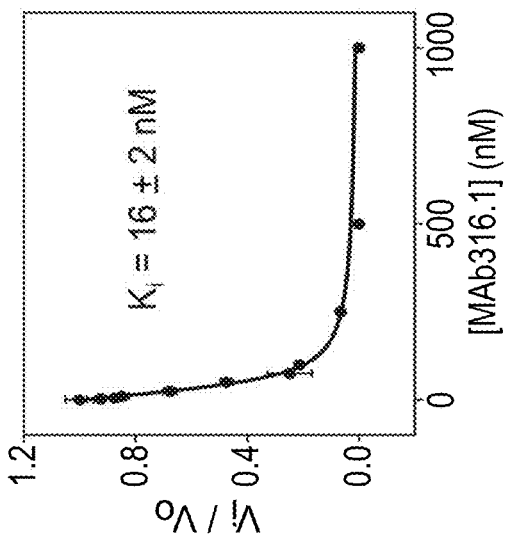
Figure 3I:
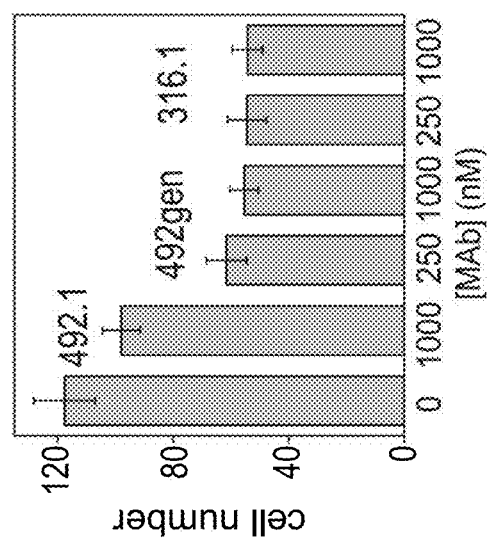

FIGS. 3A-I illustrate the evaluation of binding and inhibition constants of antibodies targeting MmQSOX1. FIG. 3A shows histograms of fluorescence (APC-conjugated streptavidin) reporting $MmQSOX1_{Trx}$ binding to the surface of yeast displaying scFv492.1 or a scFv492.1 mutant (mutant d, Table 3). Each histogram represents 50,000 yeast cells. The scFv492.1 mutant shows an increase in APC fluorescence compared to wild-type scFv492.1; FIG. 3B shows a dose-response curve of MAb492gen to 150 or 25 nM MmQSOX1, based on results from a colorimetric assay quantifying RNase A oxidation. The inhibitory activity is expressed as absorbance at 412 nm, representing free thiols that reacted with 5,5'-dithiobis-(2-nitrobenzoic acid). Error bars represent standard deviations from an average of three measurements. The $IC_{50}$ values were determined by nonlinear regression analysis and yielded values close to the MmQSOX1 concentration; FIG. 3C shows the inhibition curve of MAb492gen to 50 nM MmQSOX1, based on results from oxygen electrode assays at a range of MAb492gen concentrations. Inhibitory activity is expressed as the ratio of the inhibited rate to the uninhibited rate ($v_i/v_0$). Error bars represent standard deviations from an average of three measurements. The $K_i$ value was determined by nonlinear regression analysis; FIG. 3D shows the same as FIG. 3C only for MAb316.1; FIGS. 3E-H show representative images of laminin immunostaining in cultures treated with no antibody (FIG. 3E), MAb492.1 (FIG. 3F), MAb316.1 (FIG. 3H), or MAb492gen (FIG. 3G). Scale bar is 20 µm. Additional images are presented in FIGS. 4B-I; and FIG. 3I shows quantification of adhesion of fluorescently labeled epithelial cells to a mouse fibroblast monolayer grown in the absence or presence of MAb492.1, MAb316.1, or MAb492gen. Error bars are standard error of the mean. Sample images are shown in FIGS. 4J-O.

FIG. 3J illustrates a sequence alignment of MAb492gen and MAb492.1 variable regions. Mutated residues are colored red.

FIGS. 3K-L illustrate histograms of red fluorescence (APC bound to streptavidin) representing MmQSOX1$_{Trx}$ binding at various concentrations to the surface of yeast displaying scFv492gen (FIG. 3K). Each histogram represents 50,000 yeast cells; and FIG. 3L shows a quantification of FIG. 3K. For each histogram in FIG. 3K, the mean APC fluorescence was measured and plotted as function of MmQSOX1$_{Trx}$ concentration. Data were fit to a binding isotherm, yielding an apparent $K_d$ of 65±10 nM for MmQSOX1$_{Trx}$ binding on the surface of yeast.

Figure 4C:
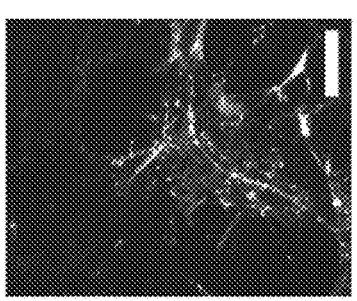
Figure 4I:
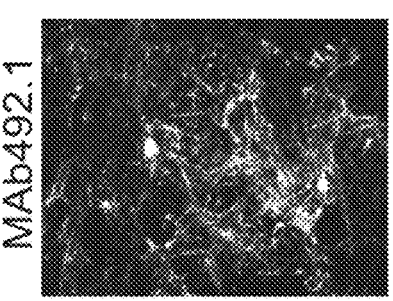
Figure 4C:
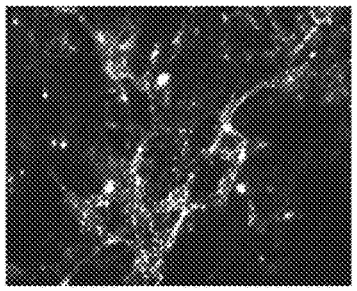
Figure 4G:
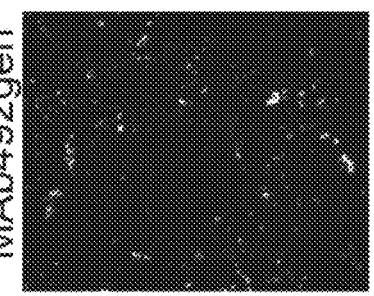
Figure 4C:
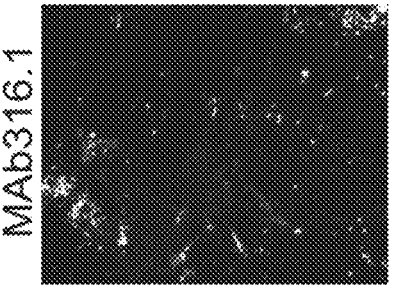
Figure 4E:
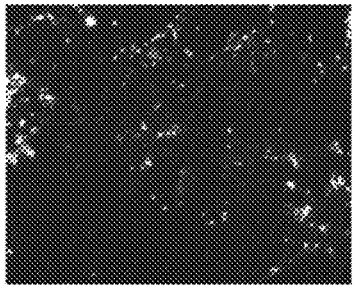
Figure 4C:
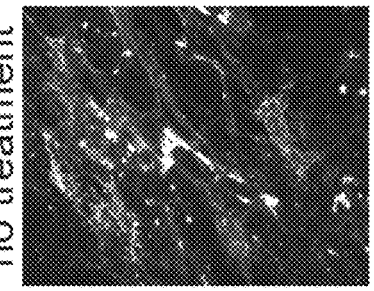
Figure 4A:
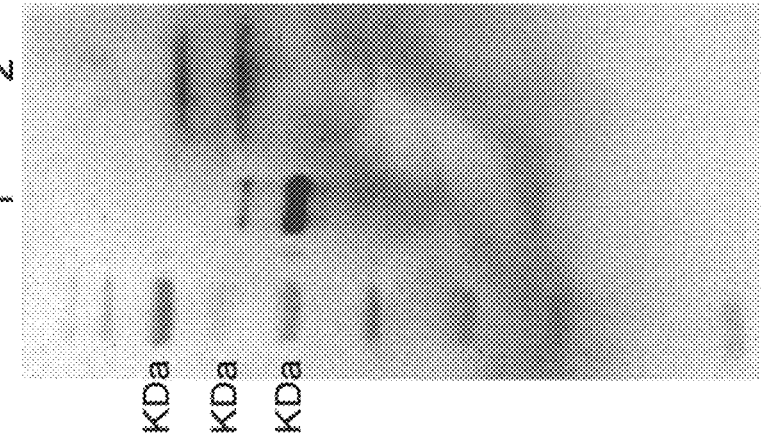

FIG. 4A illustrates a MmQSOX1 immunoblot with a rabbit polyclonal antibody (dilution 1:1000). Lane 1, recombinant MmQSOX1. Lane 2, the supernatant of confluent mouse fibroblasts, showing that MmQSOX1 is secreted. Recombinant MmQSOX1 is truncated at the carboxy-terminus and so migrates faster than endogenous secreted MmQSOX1. Endogenous MmQSOX1 appears as two bands due to its two splice variants.

FIGS. 4B-1 illustrate additional representative images of laminin immunostaining, as shown in FIGS. 3E-I. Scale bar is 40 µm.

FIGS. 4J-O illustrate representative images of adherent epithelial cells to a MEF monolayer. Fifteen such fields were quantified in each treatment (FIG. 3I). Scale bar is 100 µm.

FIGS. 5A-E are schematic illustrations of the structure of the Fab492gen-MmQSOX1Trx complex. FIG. 5A shows a surface presentation of the Fab492gen-MmQSOX1Trx complex (PDB code: 5D96) showing that Fab492gen binds MmQSOX1 in the same mode as Fab492.1 with respect to HsQSOX1Trx, by burying the Trx CXXC active site (yellow spheres); FIG. 5B shows the top view of MAb492.1 and MAb492gen CDRs. Coloring of Fab492gen chains is as in FIG. 5A. The Fab492gen-MmQSOX1Trx complex was overlaid on the Fab492.1-HsQSOX1Trx complex by aligning MmQSOX1Trx and HsQSOX1Trx; FIG. 5C shows a cartoon presentation of CDRs L2 and H3 in Fab492gen, showing their close interaction. Residues in stick presentation were mutated in the development of Fab492gen from Fab492.1. The dashed black line represents a hydrogen bond. FIGS. 5D-E show a comparison of the CDR L1-QSOX1Trx interaction in Fab492gen-MmQSOX1Trx and Fab492.1-HsQSOX1Trx complexes. Coloring is as in FIG. 5A and FIG. 5B. One hydrogen bond is possible between Fab492.1 and HsQSOX1Trx, and none between Fab492.1 and MmQSOX1Trx (FIG. 5D). Two hydrogen bonds provide interactions in the Fab492gen-MmQSOX1Trx complex (FIG. 5E).

Figure 5F:
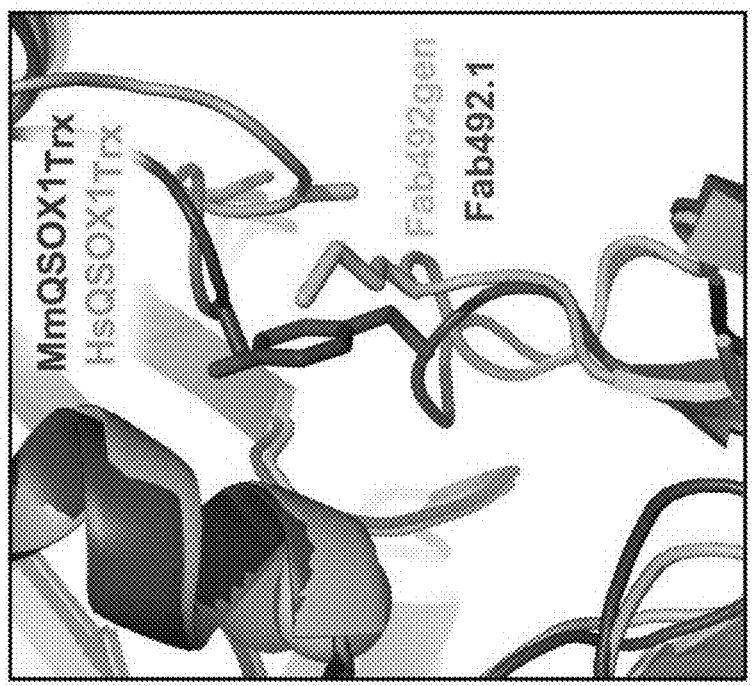

FIG. 5F is a schematic illustration showing a comparison of CDR H3 between Fab492.1 and Fab492gen. In addition to the shift in backbone, mutation of Tyr to Met prevents a clash between CDR H3 and MmQSOX1Trx. The position of CDR H3 in Fab492gen enables binding of both MmQSOX1 and HsQSOX1.

FIGS. 6A-C illustrate that MAb316.1 binds the Trx domain of MmQSOX1. FIG. 6A shows elution profiles of MAb316.1 and MmQSOX1 or its fragments from analytical size-exclusion chromatography. MAb316.1 binds the Trx module; FIG. 6B shows the surface presentation of the Fab316.1-HsQSOX1$_{Trx}$ complex (PDB code: 5D93) showing that Fab316.1 does not bury the CXXC motif, accessible at the complex surface (yellow); and FIG. 6C shows superposition of the Fab316.1-HsQSOX1$_{Trx}$ complex (PDB code: 5D93) and MmQSOX1 C76A/C455S (PDB code: 3T58). Only the variable region of the light chain is shown (gray) from Fab316.1. Yellow spheres represent the interdomain disulfide between the Trx and Erv active-site cysteines. MmQSOX1$_{Erv}$ clashes with the Fab316.1 light chain (black circle), suggesting that Fab316.1 inhibits MmQSOX1 by interfering with formation of the inter-domain electron-transfer intermediate.

Figure 7B:
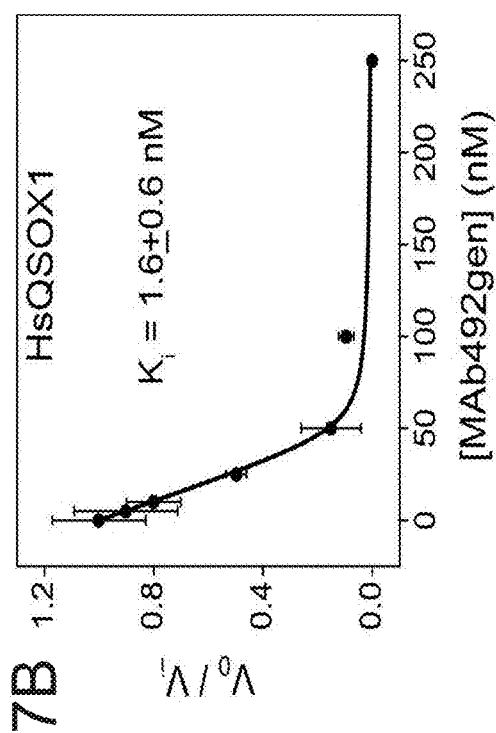
Figure 7A:
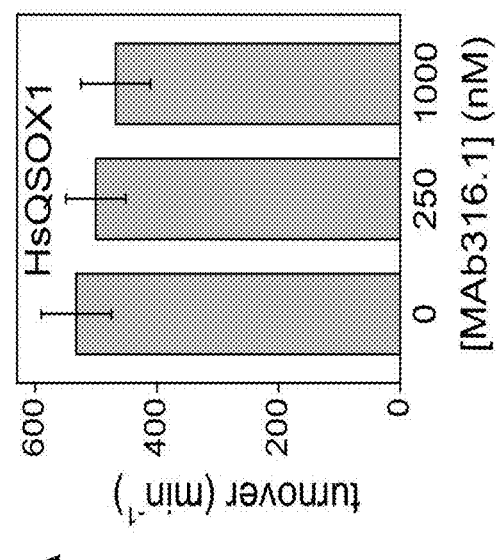
Figure 7D:
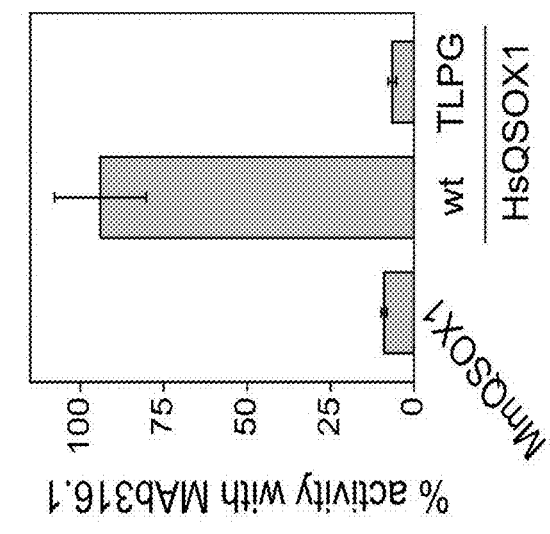
Figure 7C:
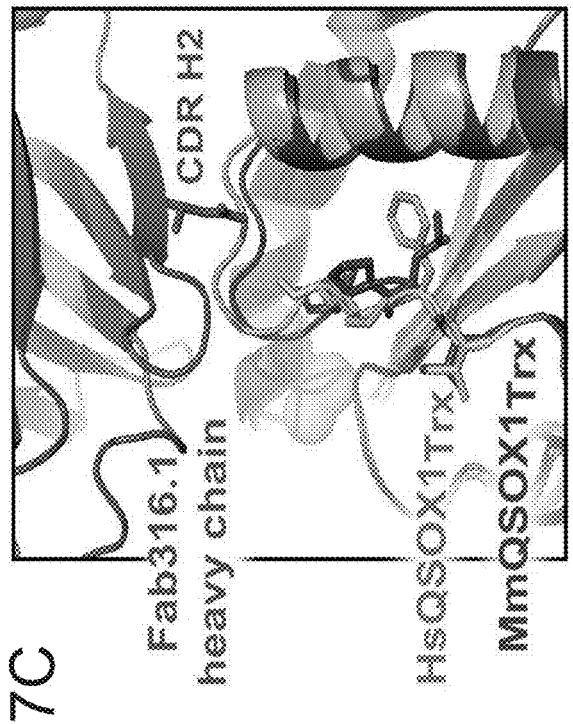

FIGS. 7A-D illustrate HsQSOX1 inhibition by MAb316.1 and MAb492gen. FIG. 7A shows turnover numbers of HsQSOX1 in the absence and presence of 250 nM or 1 µM MAb316.1. Activity was evaluated using an oxygen consumption assay. Error bars represent standard deviations from an average of three measurements; FIG. 7B shows the inhibition curve of MAb492gen calculated from oxygen electrode assays of 50 nM HsQSOX1 in the presence of various MAb492gen concentrations. Inhibitory activity is expressed as the ratio of the inhibited rate to the uninhibited rate ($v_i/v_0$). Error bars represent standard deviations from an average of three measurements. The $K_i$ value was determined by nonlinear regression analysis; FIG. 7C shows the superposition of HsQSOX1$_{Trx}$ (PDB code: 4IJ3, chain a) and Fab316.1-MmQSOX1$_{Trx}$ complex (PDB code: 5D93). Residues that differ in sequence between the two QSOX1$_{Trx}$ orthologs, namely the VFPV(135-138) loop from HsQSOX1 and the corresponding TLPG(138-141) loop from MmQSOX1, are in stick presentation. FIG. 7D shows the percent activity of MmQSOX1, HsQSOX1, and its mutant VFPV (135-138)TLPG, designated TLPG, in the presence of MAb316.1. Measurements were conducted in an oxygen consumption assay with 100 nM enzyme, 250 nM MAb492.1, and 200 µM DTT. Percent activity was calculated according to the results of the same measurements in the absence of antibody. Error bars represent standard deviations from an average of three measurements.

Figure 8:
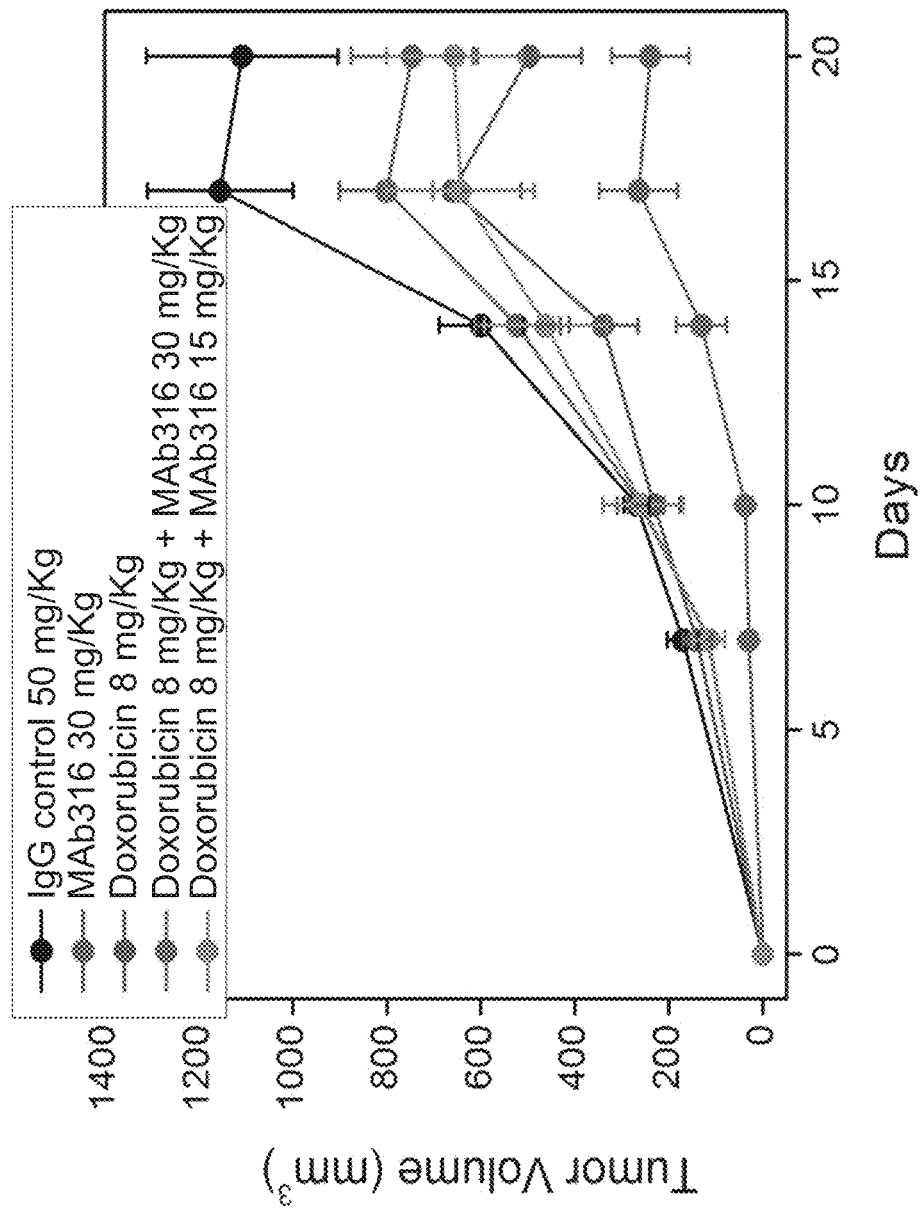

FIG. 8 illustrates in vivo that treatment with MAb316.1 slows the progression of an aggressive breast cancer in mice. Mice were treated with 15 mg/kg or 30 mg/kg of MAb316.1 and/or with doxorubicin (as described in Table 1B, hereinbelow). Average tumor volumes of the five groups of mice injected with 4T1 cells was monitored. Tumor dimensions were measured twice a week with a caliper. Tumor volume was calculated as: $x*y*z*6/\pi$. Error bars represent SEM.

DESCRIPTION OF SPECIFIC EMBODIMENTS OF THE INVENTION

The present invention, in some embodiments thereof, relates to antibodies targeting QSOX1 including cross-species-specific antibodies, and, more particularly, but not exclusively, to the generation and use of same.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The secreted disulfide catalyst Quiescin sulfhydryl oxidase 1 (QSOX1) affects extracellular matrix (ECM) composition and is over-expressed in various adenocarcinomas and associated stroma. Specifically, QSOX1 is found in the Golgi apparatus and is secreted from quiescent fibroblasts into the ECM, where it affects ECM composition and especially laminin incorporation into the basement membrane (BM), a layer of the ECM at the interface between body cavities or blood vessels and underlying stromal fibroblasts.

Inhibition of extracellular human QSOX1 by a monoclonal antibody has been previously suggested to decrease tumor cell migration. However, the species-specificity of the QSOX1 monoclonal antibody has been a setback in assessing its utility as an anti-metastatic agent in vivo, a common problem in the antibody-therapy industry.

The introduction of desired properties into monoclonal antibodies is often challenging as such properties may be accomplished on the expense of other properties. The present inventors demonstrated herein the importance of using complex structural information for identifying the specificity determinants in broadening of the antibody specificity. Thus, although human and mouse QSOX1 have a high sequence identity (79%), structural differences are noted between HsQSOX1 and MmQSOX1 which affect species specificity of the antibody. In order to broaden antibody species specificity, the present inventors found that relieving steric clashes between the anti-QSOX1 antibody and its target is necessary but not sufficient to extend binding to a distinct ortholog of the target human QSOX1 and that additional favorable interactions have to be introduced. These interactions are accomplished by altering the association between the heavy and light antibody chains, which recruits CDRs L1 and L2 into the antibody-MmQSOX1 interface. Moreover, dual specificity is enabled by substituting the constrained rings of aromatic residues with more flexible side chains, including those that can participate in water-bridged polar interactions. CDRs that recognize structurally conserved elements are left in their natural state, preserving specificity to QSOX1 antigens.

Thus, while reducing the present invention to practice, the present inventors have performed a structure-guided modification of the MAb492.1 antibody (which binds human QSOX1) to introduce point mutations rendering the antibody (termed MAb492gen) capable of binding the mouse QSOX1 ortholog. The present inventors have also generated a new anti-QSOX1 inhibitory monoclonal antibody targeting murine QSOX1. These antibodies can be used in in vivo pre-clinical trials overcoming the barriers of species cross-reactivity as well as for various biotechnological applications.

As is shown herein below and in the Examples section which follows, the present inventors have used structure-guided engineering to expand the antibody species specificity, improving its affinity towards mouse QSOX1 by at least four orders of magnitude (Tables 3 and 4, FIGS. 3A-L). A crystal structure of the re-engineered variant, complexed with its mouse antigen, revealed that the antibody accomplishes dual-species targeting through altered contacts between its heavy and light chains, plus replacement of bulky aromatics by flexible side chains and versatile water-bridged polar interactions (FIGS. 5A-F). The present inventors have also produced an antibody targeting mouse QSOX1, termed MAb316.1, which exhibits a new QSOX1 inhibition mode (Table 2, FIGS. 6A-C). Thus, while MAb492.1 and MAb492gen inhibit QSOX1 by blocking substrate access to the Trx CXXC redox-active site (FIG. 1B), Fab316.1 envelopes the helix containing the Trx redox-active site at its amino terminus but does not block access to the CXXC motif itself (FIG. 6B). Accordingly, MAb316.1 inhibits QSOX1 by physically preventing formation of the inter-domain electron-transfer intermediate of MmQSOX1 (FIG. 6C), thus interrupting a different step in the catalytic cycle than MAb492.1 and MAb492gen (transition from state 2 to 3, rather than 1 to 2 in FIG. 1C).

These discoveries provide the framework for generating cross-species-specific antibodies capable of binding and inhibiting mouse and human QSOX1 for pre-clinical trials for better qualifying antibodies for future therapeutic applications.

Thus, according to one aspect of the present invention there is provided an antibody comprising an antigen recognition domain exhibiting species cross reactivity to human QSOX1 and murine QSOX1.

As used herein, the term "QSOX1" relates to the Quiescin Sulfhydryl Oxidase 1. The protein accession number for the long variant of human QSOX1 on the NCBI database is NP_002817 (SEQ ID NO: 3), and the accession number for the short form of human QSOX1 is NP_001004128 (SEQ ID NO: 4). The protein accession number for the long variant of mouse QSOX1 on the NCBI database is NM_001024945.1 (SEQ ID NO: 34), and the accession number for the short form of mouse QSOX1 is NM_023268.2 (SEQ ID NO: 35).

The antibody of the present invention exhibits species cross reactivity to human QSOX1 and murine QSOX1 (e.g., mouse QSOX1).

The term "species cross reactivity" as used herein refers to binding of the antigen recognition domain described herein to the same target molecule in humans and mice (i.e. QSOX1) with substantially the same affinity (as determined by a specific affinity assay e.g., BiaCore, ELISA). According to one embodiment, the binding of the antigen recognition domain described herein to the same target molecule in humans and mice (i.e. QSOX1) results in the same activity (e.g., inhibition of QSOX1 activity).

As used herein "substantially the same affinity" refers to a binding affinity which is the same or within one order of magnitude difference, as determined in the same binding assay.

According to one embodiment, the affinity of the antibody to human QSOX1 is characterized by a $K_D$ of 0.1-100 nM, $K_D$ of 0.1-50 nM, $K_D$ of 0.1-10 nM, $K_D$ of 1-10 nM, $K_D$ of 0.1-5 nM, $K_D$ of 1-5 nM, $K_D$ of 1-3 nM, $K_D$ of 1.5-2 nM, or $K_D$ of 1.6 nM.

According to one embodiment, the affinity of the antibody to mouse QSOX1 is characterized by a $K_D$ of 0.1-100 nM, $K_D$ of 0.1-50 nM, $K_D$ of 0.1-10 nM, $K_D$ of 1-10 nM, $K_D$ of 0.1-5 nM, $K_D$ of 1-5 nM, $K_D$ of 2-3 nM, $K_D$ of 2-2.5 nM, or $K_D$ of 2.2 nM.

Thus, "species cross reactivity" is to be understood as an interspecies reactivity to the same molecule (i.e. QSOX1) of different species, but not to a molecule other than QSOX1.

Species cross reactivity of an antibody recognizing human QSOX1 and mouse QSOX1 can be determined, for example, by FACS analysis. The FACS analysis is carried out in a way that the respective antibody is tested for binding to the human and mouse QSOX1 proteins. For example, a yeast-surface display may be used for expression of single-chain variable fragments (scFv) of the antibody tested. Binding of scFv displayed on cells to soluble QSOX1 (e.g., human or mouse) can be monitored using FACS analysis, e.g., utilizing streptavidin-APC fluorescence. Alternatively, species cross reactivity may be determined by any other method known in the art, e.g., by ELISA.

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen.

The term "isolated" refers to at least partially separated from the natural environment e.g., from a hybridoma cell.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule;

(iii) disulfide-stabilized Fv ("dsFv"), a genetically engineered antibody including the variable region of the light chain and the variable region of the heavy chain, linked by a genetically engineered disulfide bond;

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g., Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [*Biochem. J.* 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [*Proc. Nat'l Acad. Sci. USA* 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, *Methods* 2: 97-105 (1991); Bird et al., *Science* 242:423-426 (1988); Pack et al., *Bio/Technology* 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [*Methods,* 2: 106-10 (1991)].

Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature,* 321:522-525 (1986); Riechmann et al., *Nature* 332:323-327 (1988); Verhoeyen et al., *Science,* 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies [Cole et al., *Monoclonal Antibodies and Cancer Therapy,* Alan R. Liss, p. 77 (1985) and Boerner et al., *J. Immunol.,* 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368 812-13 (1994); Fishwild et al., *Nature Biotechnology* 14, 845-51 (1996); Neuberger, *Nature Biotechnology* 14: 826 (1996); and Lonberg and Huszar, *Intern. Rev. Immunol.* 13, 65-93 (1995).

According to one embodiment, there is provided a method of producing an antibody which comprises an antigen recognition domain exhibiting species cross reactivity to QSOX1, the method comprising: (a) introducing at least one point mutation in the antigen binding domain of an antibody which binds QSOX1 of a first species, which at least one point mutation increases the water-mediated hydrogen bonding in the interaction interface between the antigen binding domain of the antibody and QSOX1 of the first species, and alternatively or additionally the at least one point mutation reduces aromatic interactions between the antigen binding domain of the antibody and QSOX1 of the first species, wherein the at least one point mutation does not substantially affect affinity of the antibody to QSOX1 of the first species; and (b) testing binding of the antibody having the at least one point mutation to QSOX1 of a second species, wherein when the antibody having the at least one point mutation binds QSOX1 of the first species and the second species with substantially the same affinity the antibody is considered having cross reactivity to QSOX1.

Accordingly, any antibody which binds a first species (e.g., human) QSOX1 may be used. Such antibodies may be obtained commercially (e.g., from Merck Millipore, Atlas Antibodies, MBL International or Thermo Scientific Pierce Antibodies), or may be produced by any method known in the art, e.g., as described below, provided that their coding sequence can be elucidated.

According to one embodiment, anti-QSOX1 monoclonal antibodies may be produced e.g., in murine animals, such as in mice, by first immunizing with an emulsion of recombinant human QSOX1 and Complete Freund's adjuvant (e.g., obtained from DifcoLboratories). For instance, mice may be immunized three, four, or five times at intervals of two or three weeks. QSOX1 peptides used for immunization may comprise between 50-100 amino acids, between 50-150 amino acids, between 50-200 amino acids, between 50-232 amino acids, between 100-200 amino acids or between 150-232 amino acids.

According to one embodiment, immunization can be done using a fragment spanning 33 to 546 of *Homo sapiens* QSOX1, which comprises all the functional domains of the enzyme.

According to one embodiment, immunization can be done using a fragment spanning residues 33 to 272 of *Homo sapiens* QSOX1.

According to one embodiment, immunization can be done using the Trx module of QSOX1 (e.g., two Trx domains) or using the Erv module of QSOX1 (e.g., two Erv domains).

According to one embodiment, immunization can be done using the full-length QSOX1.

Next, spleen cells from selected mice are fused with myeloma cells (e.g., NSO myeloma cells) using polyethylene glycol. Hybridoma cells are then selected by a selection medium (e.g., HAT medium) and supernatants of the cells (i.e. comprising the antibodies) are screened for specific binding to human QSOX1 and/or inhibition thereof.

In order to generate antibodies with species cross reactivity (e.g., to human and mouse QSOX1), at least one amino acid sequence of the antibody is modified (e.g., by point mutations, deletions and/or insertions), wherein the modification enables functional flexibility, i.e., flexibility in the interaction interface of the antibody with an antigen, enabling interaction with more than one antigen (e.g., QSOX1 of different species).

As detailed in the Examples section which follows, the amino acid sequence of the antibody may be modified to comprise a lower content of aromatic amino acids (e.g., tyrosines) as compared to that of a species-specific antibody to the human QSOX1. The aromatic amino acids may be replaced by more flexible amino acids (i.e. amino acids comprising flexible side chains). Furthermore, the amino acid of the antibody may be modified to include at least one charged amino acid (i.e., amino acid which comprises a charged residue). It will be appreciated that charged amino acids comprise energetically favorable contact with water and accordingly can participate in water-bridged polar interactions between the antibody and QSOX1.

Thus, according to one embodiment, in order to generate antibodies with species cross reactivity an antibody recognizing human QSOX1 is modified in at least one amino acid residue.

According to one embodiment, 1, 2, 3, 4, 5, 6, 7, 8, 9, 10, 11, 12 or more point mutations are generated in the amino acid sequence of the antibody.

According to one embodiment, the point mutation is generated in the heavy chain of the antibody.

According to one embodiment, the point mutation is generated in the light chain of the antibody.

According to an embodiment, the point mutation may be a plurality of point mutations in the heavy chain and in the light chain of the antibody.

According to one embodiment, the at least one point mutation is at the antigen binding domain of the antibody.

According to one embodiment, the at least one point mutation is in a CDR sequence of the antibody.

According to one embodiment, 1, 2, 3, 4, 5, 6, 7, 8, 9, 10, 11, 12 or more point mutations are generated in CDR sequences of the antibody.

According to a specific embodiment, a point mutation is generated in the heavy chain variable region of the antibody, e.g., in CDR1, CDR2 and/or CDR3.

According to specific embodiment, a point mutation is generated in the light chain variable region of the antibody, e.g., in CDR1, CDR2 and/or CDR3.

According to one embodiment, the at least one point mutation which reduces aromatic interactions is in an aromatic amino acid (e.g. tyrosine). Accordingly, aromatic amino acids within the amino acid sequence of the antibody may be replaced by more flexible amino acids (as discussed in detail below).

According to one embodiment, the at least one point mutation which reduces aromatic interactions comprises an amino acid comprising a flexible side chain.

According to one embodiment, the amino acid sequence of the antibody comprises a lower content of aromatic amino acids (e.g., tyrosines) as compared to that of a species-specific antibody to the human QSOX1.

According to one embodiment, the amino acid sequence of the antibody comprises a lower content of aromatic amino acids (e.g., tyrosines) in CDRs of the antigen recognition domain as compared to that of a species-specific antibody to the human QSOX1.

A lower content of aromatic amino acids may include 1, 2, 3, 4, or 5 fewer aromatic amino acids (e.g., tyrosines) in the amino acid sequence of the antibody as compared to that of a species-specific antibody to the human QSOX1 (e.g., mAb492.1).

Aromatic amino acids include, for example, tyrosine, phenylalanine, histidine and tryptophan.

According to a specific embodiment, the amino acid sequence of the antibody comprises a lower content of tyrosines as compared to that of a species-specific antibody to the human QSOX1.

According to a specific embodiment, the amino acid sequence of the antibody comprises a lower content of tyrosines in CDRs of the antigen recognition domain as compared to that of a species-specific antibody to the human QSOX1.

A lower content of tyrosines may include 1, 2, 3, 4, or 5 fewer tyrosines in the amino acid sequence of the antibody as compared to that of a species-specific antibody to the human QSOX1 (e.g., mAb492.1).

According to another specific embodiment, the amino acid sequence of the antibody comprises a lower content of aromatic amino acids (e.g., tyrosine) in CDR3 of the variable heavy chain of the antibody (as compared to that of a species-specific antibody to the human QSOX1). Additionally or alternatively, the amino acid sequence of the antibody comprises a lower content of aromatic amino acids (e.g., tyrosine) in CDR2 of the variable light chain of the antibody (as compared to that of a species-specific antibody to the human QSOX1).

According to another specific embodiment, tyrosine at position 99 of the variable heavy chain of the antibody as set forth in SEQ ID NO: 37 is replaced by a point mutation. Additionally or alternatively, tyrosine at position 100 of the variable heavy chain of the antibody as set forth in SEQ ID NO: 37 is replaced by a point mutation. Additionally or alternatively, tyrosine at position 53 of the variable light chain of the antibody as set forth in SEQ ID NO: 36 is replaced by a point mutation.

According to another specific embodiment, aromatic amino acids (e.g., tyrosine) are replaced by more flexible amino acids (i.e. amino acids comprising flexible side chains), including, but not limited to glutamine, methionine, arginine, lysine, aspartate, glutamate, and serine.

According to another specific embodiment, tyrosine at position 99 of the variable heavy chain of the antibody as set forth in SEQ ID NO: 37 is replaced by a serine. Additionally or alternatively, tyrosine at position 100 of the variable heavy chain of the antibody as set forth in SEQ ID NO: 37 is replaced by a methionine. Additionally or alternatively, tyrosine at position 53 of the variable light chain of the antibody as set forth in SEQ ID NO: 36 is replaced by a glutamine.

As discussed above, in order to improve antibody binding to murine QSOX1, the antibody of the invention may alternatively or additionally be modified to include at least one charged amino acid residue.

According to one embodiment, the at least one point mutation which increases the water-mediated hydrogen bonding comprises at least one charged or polar (e.g. non-charged polar) amino acid.

According to one embodiment, the amino acid sequence of the antibody comprises at least 1, 2, 3 or more charged or polar amino acids in the amino acid sequence of the antibody as compared to that of a species-specific antibody to human QSOX1 (e.g., mAb492.1).

According to one embodiment, the amino acid sequence of the antibody comprises at least one charged or polar amino acid in a CDR of the antigen recognition domain of the antibody.

According to one embodiment, the amino acid sequence of the antibody comprises at least one charged or polar amino acid in CDR3 of a variable heavy chain of the antibody.

Charged amino acids (i.e. amino acids which comprise a charged residue) include, but are not limited to, lysine, arginine, aspartic acid, histidine and glutamic acid.

Polar amino acids include, but are not limited to, serine, threonine, asparagine, glutamine, histidine and tyrosine.

According to one embodiment, the at least one point mutation which increases the water-mediated hydrogen bonding is an aspartic acid.

According to a specific embodiment, the amino acid sequence of the antibody comprises aspartic acid in CDR3 of a variable heavy chain of the antibody (e.g., at position 101 of a variable heavy chain amino acid sequence of the antibody as set forth in SEQ ID NO: 45).

According to one embodiment, the amino acid sequence of the antibody comprises a serine, methionine, aspartic acid, proline (i.e. SMDP) sequence in CDR3 of the variable heavy chain of the antibody (e.g., at positions 99-102 of a variable heavy chain amino acid sequence of the antibody as set forth in SEQ ID NO: 45).

The modification to the antibody's amino acid sequence is typically carried out using the minimal number of amino acid alteration in order to increase binding affinity to and optimally inhibit mouse QSOX1 without substantially losing binding affinity to human QSOX1 (i.e. binding affinity which is the same or within one order of magnitude difference, as determined in the same binding assay).

In order to select an antibody with species cross reactivity, the antibody generated according to the teachings of some embodiments of the invention is tested for binding of the antibody having the at least one point mutation to QSOX1 of a second species, wherein when the antibody having the at least one point mutation binds QSOX1 of the first species and the second species with substantially the same affinity the antibody is considered having cross reactivity to QSOX1.

Selecting antibodies which bind to a first species (e.g., human) QSOX1 and a second species (e.g., mouse) QSOX1 (i.e. species cross reactivity) can be carried out using any method known in the art (e.g., by a specific affinity assay using, for example, BiaCore, ELISA or FACS analyses as described in detail hereinabove) as long as the same assay and conditions are used for both species (e.g., human and murine) QSOX1.

Large scale antibodies may then be produced using, for example, a miniPERM bioreactor (Sarstedt) in serum-free medium (DCCM).

Thus, the teachings of the present invention provide for an antibody comprising an antigen recognition domain which binds to human QSOX1 and murine QSOX1.

According to one aspect of the invention, there is provided an antibody comprising an antigen recognition domain exhibiting species cross reactivity to human QSOX1 and murine QSOX1, the antigen recognition domain comprising complementarity determining regions (CDRs) as set forth in SEQ ID NOs: 46-51.

According to a specific embodiment, the antibody of the present invention is a monoclonal antibody (MAb).

According to a specific embodiment, CDRs 1-3 (SEQ ID NOs: 46-48, respectively) are located on the light chain of the MAb antibody.

According to another specific embodiment, CDRs 1-3 (SEQ ID NOs: 49-51, respectively) are located on the heavy chain of the MAb antibody.

According to a specific embodiment the MAb antibody is MAb492gen.

According to another embodiment, the antibody of the present invention is a single chain antibody.

According to another specific embodiment, CDRs 1-3 (SEQ ID NOs: 46-48, respectively) are located on the light chain of the single chain antibody.

According to another specific embodiment, CDRs 1-3 (SEQ ID NOs: 49-51, respectively) are located on the heavy chain of the single chain antibody.

An exemplary single chain antibody which may be used in accordance with the present teachings is scFv492gen.

According to another embodiment scFv492gen comprises CDRs set forth in SEQ ID NOs: 46-51.

According to another embodiment, the antibody of the present invention is a fragment antigen-binding (Fab) antibody.

According to another specific embodiment, CDRs 1-3 (SEQ ID NOs: 46-48, respectively) are located on the light chain of the Fab antibody.

According to another specific embodiment, CDRs 1-3 (SEQ ID NOs: 49-51, respectively) are located on the heavy chain of the Fab antibody.

An exemplary Fab antibody which may be used in accordance with the present teachings is Fab492gen.

According to another embodiment Fab492gen comprises CDRs set forth in SEQ ID NOs: 46-51.

According to another embodiment, an isolated antibody of the present invention comprises the amino acid sequence as set forth in SEQ ID NOs: 44 and 45.

According to some embodiments of the invention, the amino acid sequence comprises an amino acid sequence having at least 80%, at least 81%, 82%, 83%, 84%, 85%, 86%, 87%, 88%, 89%, 90%, 91%, 92%, 93%, 94%, 95%, 96%, 97%, 98%, 99%, or 100% sequence homology or identity to the peptide set forth in SEQ ID NOs: 44 and 45, wherein the antibody is capable of binding human QSOX1 and mouse QSOX1 according to the cross reactivity definition.

Homology (e.g., percent homology, identity+similarity) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

For example, default parameters for tBLASTX include: Max target sequences: 100; Expected threshold: 10; Word size: 3; Max matches in a query range: 0; Scoring parameters: Matrix—BLOSUM62; filters and masking: Filter—low complexity regions.

The teachings of the present invention also provide for an antibody capable of binding mouse QSOX1.

According to one aspect of the invention, there is provided an antibody comprising an antigen recognition domain comprising CDRs as set forth in SEQ ID NOs: 26-31, wherein the antibody specifically binds murine QSOX1.

According to a specific embodiment, the antibody capable of binding murine QSOX1 of the present invention is a monoclonal antibody (MAb).

According to a specific embodiment, CDRs 1-3 (SEQ ID NOs: 26-28, respectively) are located on the light chain of the MAb antibody.

According to a specific embodiment CDRs 1-3 (SEQ ID NOs: 29-31, respectively) are located on the heavy chain of the MAb antibody.

An exemplary monoclonal antibody which may be used in accordance with the present teachings is MAb316.1.

According to a specific embodiment, MAb316.1 comprises CDRs set forth in SEQ ID NOs: 26-31.

According to another embodiment, an isolated antibody of the present invention comprises the amino acid sequence as set forth in SEQ ID NOs: 9 and 10.

According to some embodiments of the invention, the amino acid sequence comprises an amino acid sequence having at least 80%, at least 81%, 82%, 83%, 84%, 85%, 86%, 87%, 88%, 89%, 90%, 91%, 92%, 93%, 94%, 95%, 96%, 97%, 98%, 99%, or 100% sequence homology or identity to the peptide set forth in SEQ ID NOs: 9 and 10, wherein the antibody is capable of binding mouse QSOX1.

The antibodies and antibody fragments generated according to the teachings of the present invention serve as inhibitors of QSOX1.

According to one embodiment of the invention, the antibodies or antibody fragments inhibit QSOX1 activity in mediating laminin incorporation in the basement membrane, e.g., laminin assembly that supports cell migration.

As used herein, the term "laminin" refers to a human laminin protein. Typically laminins are trimeric proteins that contain an α-chain, a β-chain, and a γ-chain (found in five, four, and three genetic variants, respectively). Thus, the term laminin as used herein encompasses any type of human laminin, including any of the different chain combinations or any individual subunits of laminin. The different chains and trimer molecules differ with respect to their tissue distribution apparently reflecting diverse functions in vivo. Exemplary laminin subunits of the present invention include, but are not limited to, LAMA1, LAMA2, LAMA3, LAMA4, LAMA5, LAMB1, LAMB2, LAMB3, LAMB4, LAMC1, LAMC2 and LAMC3.

According to an embodiment of the present invention, the laminin comprises an alpha 4 chain.

According to a specific embodiment, the laminin is laminin-411 or laminin-421.

The term "laminin assembly" refers to the incorporation of laminin proteins into the basal lamina (i.e. one of the layers of the basement membrane). Typically, laminin is secreted from cells (e.g., fibroblasts, epithelial cells, tumor cells) and is incorporated into cell-associated extracellular matrices where they form independent networks and are associated with type IV collagen networks via entactin, fibronectin and perlecan.

The term "basement membrane" or "laminin-comprising basement membrane" refers to the thin layer of fibers which anchors and supports the epithelium and endothelium and comprises the basal lamina (i.e. comprising laminin).

The phrase "inhibiting or preventing laminin assembly" refers to reducing, reversing, attenuating, minimizing, suppressing or halting laminin assembly in a basement membrane. According to one embodiment, inhibiting or preventing laminin assembly is by at least about 10%, by at least about 20%, by at least about 30%, by at least about 40%, by at least about 50%, by at least about 60%, by at least about 70%, by at least about 80%, by at least about 90% or by about 100%, as compared to laminin assembly in the absence of the anti-QSOX1 antibody or antibody fragment (as described hereinabove). Thus, according to an embodiment of the invention laminin is not incorporated into the basement membrane.

Laminin which is not incorporated into the basal membrane can be found in soluble form (e.g., in the culture medium of in vitro cultured cells). Thus, monitoring reduction in laminin assembly can be monitored by e.g., immunofluorescence (IF) staining of the extracellular matrix or by Western blotting of the soluble laminin (i.e. that which was not incorporated into the basal membrane).

According to an embodiment of the invention, the activity of the antibody in inhibiting QSOX1 activity is assayed by at least one of an immunofluorescence (IF) staining assay of the extracellular matrix or Western blot assay for soluble laminin (i.e. that which is not incorporated into the basal membrane, as further described in the Examples section which follows).

It will be appreciated that inhibiting or preventing laminin assembly may be advantageous in situations in which excess connective tissue is produced in a non-structured manner in an organ or tissue in a reparative or reactive process, such as fibrosis. Thus, while further reducing the present invention to practice, inhibition of QSOX1 and subsequently generation of soluble laminin may be therapeutic for fibrotic processes.

It will be appreciated that laminins are an important biologically active part of the basal lamina and basal membrane influencing cell adhesion, signaling, migration, phenotype, differentiation and survival. An exemplary cell migration of the present invention comprises tumor cell migration leading to metastasis.

Accordingly, inhibiting or preventing laminin assembly may be advantageous in situations in which inhibition of cell migration is warranted. The cell may comprise, for example, a brain cell, a neuron, a cardiac cell, a muscle cell, a skin cell, a bone cell, a pancreatic cell, a liver cell, a kidney cell, an intestinal cell, a spleen cell, a respiratory cell, a lung cell, a lymphocyte or a monocyte. The cell of the present invention may comprise a healthy cell or may alternately comprise a mutated cell (e.g., a tumor cell).

According to one embodiment, inhibiting or preventing cell migration refers to reducing, reversing, attenuating, minimizing, suppressing or halting migration of a cell (e.g., tumor cell) via a laminin-comprising basement membrane.

According to one embodiment, inhibiting or preventing cell migration is by at least about 10%, by at least about 20%, by at least about 30%, by at least about 40%, by at least about 50%, by at least about 60%, by at least about 70%, by at least about 80%, by at least about 90% or by at least about 100%, as compared to cell migration via a laminin-comprising basement membrane in the absence of the anti-QSOX1 antibody or antibody fragment (as described hereinabove). Thus, according to an embodiment of the invention cell migration is completely inhibited through the basement membrane.

The methods of the present invention (e.g., inhibiting cell migration) may be effected in vitro, in vivo or ex vivo.

As mentioned, the ability to modulate cell migration can be used as a therapeutic modality.

Accordingly, one specific use for the antibodies of the present invention is for preventing or treating a laminin-associated disease or condition in a subject in need thereof.

The phrase "preventing or treating" refers to inhibiting or arresting the development of a disease, disorder or condition and/or causing the reduction, remission, or regression of a disease, disorder or condition or keeping a disease, disorder or medical condition from occurring in a subject who may be at risk for the disease disorder or condition, but has not yet been diagnosed as having the disease disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" refers to an animal, preferably a mammal, most preferably a human being, including both young and old human beings of both genders who suffer from or are predisposed to a laminin-associated disease or condition.

As used herein, the term "laminin-associated disease or condition" refers to a disease or condition in which laminin function is associated with the onset or progression of a disease.

According to one embodiment, the laminin-associated disease or condition is a tumor.

Examples of tumors include, but are not limited to, carcinoma, blastoma and sarcoma. Particular examples of cancerous diseases but are not limited to: myeloproliferative diseases, such as solid tumors benign meningioma, mixed tumors of salivary gland, colonic adenomas; adenocarcinomas, such as small cell lung cancer, kidney, uterus, prostate, bladder, ovary, colon, sarcomas, liposarcoma, myxoid, synovial sarcoma, rhabdomyosarcoma (alveolar), extraskeletal myxoid chonodrosarcoma, Ewing's tumor; other include testicular and ovarian dysgerminoma, retinoblastoma, Wilms' tumor, neuroblastoma, malignant melanoma, mesothelioma, breast, skin, prostate, and ovarian.

According to an embodiment, the tumor is a metastasizing solid tumor (e.g., formed by metastatic cancer cells).

According to an embodiment, the tumor is an adenocarcinoma.

According to one embodiment the tumor is a cancer.

Types of cancerous diseases amenable to treatment by the methods of some embodiments of the invention include benign tumors, warts, polyps, pre-cancers, and malignant tumors/cancers.

Specific examples of cancerous diseases which can be treated using the methods of the present invention include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypemrnephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to a specific embodiment of this aspect of the present invention, the cancers which may be treated in accordance with the present teachings, include but are not limited to, prostate cancer, lung cancer, breast cancer, cervical cancer, urachus cancer, vaginal cancer, colon cancer, esophagus cancer, pancreatic cancer, throat cancer, stomach cancer and myeloid leukemia.

According to one embodiment, the laminin-associated disease or condition is associated with fibrosis.

The term "fibrosis" refers to a formation or a presence of excess connective tissue in an organ or tissue. It may occur as a repair or replacement response to a stimulus such as tissue injury or inflammation.

Examples of disorders involving fibrosis include, but are not limited to, liver fibrosis, pulmonary fibrosis, renal fibrosis, pancreatic fibrosis, scleroderma, connective tissue diseases, scarring, skin fibrosis, cardiac fibrosis, organ transplant, vascular stenosis, restenosis, arterial fibrosis, arthrofibrosis, breast fibrosis, muscle fibrosis, retroperitoneal fibrosis, thyroid fibrosis, lymph node fibrosis, bladder fibrosis, pleural fibrosis and COPD.

According to one embodiment, the laminin-associated disease or condition is a bacterial disease, a viral disease or a parasitic disease.

An exemplary parasitic disease which may be treated by the teachings of the present invention includes African trypanosomiasis.

According to the present teachings, in order to treat the laminin-associated disease or condition, the subject is administered with the anti-QSOX1 antibody (or antibody fragment) of some embodiments of the invention, as further detailed hereinabove.

Each of the antibody or antibody fragments described hereinabove can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the anti-QSOX1 antibody or fragment thereof accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (anti-QSOX1 antibody or fragment thereof) effective to prevent, alleviate or ameliorate symptoms of a disorder (e.g., laminin-associated disease or condition) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Animal models for laminin-associated diseases include, for example, the murine animal model for liver fibrosis [see e.g., review paper by Hiromitsu Hayashi and Takao Sakai 1, *Amer Journal Physiol—GI*(2011) 300(5): G729-G738] and the murine animal model for metastatic breast cancer [Anna Fantozzi and Gerhard Christofori, *Breast Cancer Research* (2006) 8:212].

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

It will be appreciated that the antibodies of some embodiments of the invention exhibiting cross-species reactivity (e.g., recognizing both human and mouse QSOX1) are particularly useful for preclinical trials to determine the therapeutic effective amount, toxicity and the efficacy of the antibodies for treatment. Furthermore, the anti-mouse QSOX1 antibodies of some embodiments of the invention may also be used for preclinical trials to determine the therapeutic effective amount, toxicity and the efficacy of the antibodies for treatment.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one embodiment, the antibody of some embodiments of the invention is used in conjunction with another agent capable of treating a laminin-associated disease or condition in a subject (e.g. tumor). In such cases, the antibody may be administered to the subject prior to, concomitantly with, or following said other agent (e.g. within a time frame of 30 minutes, 1 hour, 2 hours, 4 hours, 6 hours, 12 hours, 24 hours, 36 hours, 48 hours, 3 days, 4 days, 5 days, 6 days, 7 days, 10 days, 14 days, 21 days, 30 days, 60 days, 90 days or 120 days of each other).

Exemplary agents include, but are not limited to, chemotherapeutic agents (e.g. cytotoxic drugs), hormonal therapeutic agents, radiotherapeutic agents, anti-proliferative agents, and combinations thereof.

Non-limiting examples of chemotherapeutic agents include, but are not limited to, platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

According to a specific embodiment the chemotherapeutic agent is Doxorubicin.

It will be appreciated that the antibody may allow lower doses of chemotherapeutic agents to be used (e.g. doses which are less than the current gold standard), thus minimizing adverse toxicity typically associated with the use of such treatments.

Examples of hormonal therapeutic agents include, but are not limited to, aromatase inhibitors (e.g., aminoglutethimide, anastrozole (Arimidex®, letrozole (Femora®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Radiation therapy includes, but is not limited to, fractionated radiotherapy, non-fractionated radiotherapy and hyperfractionated radiotherapy, and combination radiation and chemotherapy. Types of radiation also include ionizing (gamma) radiation, particle radiation, low energy transmission (LET), high energy transmission (HET), ultraviolet radiation, infrared radiation, visible light, and photosensitizing radiation.

Exemplary anti-proliferative agents include mTOR inhibitors such as sirolimus (rapamycin), temsirolimus (CCI-779), and everolimus (RAD001); Akt inhibitors such as IL6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)me-thyl)-4-piperidinyl)-2H-benzimidazol-2-one, 10-(4'-(N-diethylamino)butyl)-2-chlorophenoxazine, 3-formylchromone thiosemicarbazone (Cu(II)Cl.sub.2 complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125:1144-1145 (2003) and Kau et al., *Cancer Cell*, 4:463-476 (2003); and combinations thereof.

It will be appreciated that since the anti-QSOX1 antibody or antibody fragment of the present invention is capable of specifically binding human QSOX1 and mouse QSOX1, and since QSOX1 levels are elevated in medical conditions associated with laminin (e.g., tumors or fibrosis), such an antibody can be used in assessing the efficiency of treatment (e.g., in preclinical trials prior to human therapeutics).

Thus, according to an aspect of the present invention there is provided a method for in vivo determining the efficiency of an antibody in reducing a laminin-associated disease or condition in a murine animal, the method comprising administering to the murine animal the antibody of some embodiments of the invention and monitoring progression of a laminin-associated disease or condition in the murine animal, thereby determining the efficiency of the antibody.

As used herein, the term "in vivo" refers to a process occurring within a living organism.

According to one embodiment, the organism is a murine animal including a mouse or a rat. Alternatively, other animal models known in the art, including e.g., guinea pigs, hamsters, rabbits or gerbils, can be used in accordance with the present teachings.

According to a specific embodiment, the murine animal is a mouse.

According to one embodiment, the murine animal (e.g., mouse) can lack all or part of a functional immune system (e.g., SCID mouse) or a full or part of a gene (e.g., knockout mouse or transgenic mouse). The murine animal may also be a xenograft animal model (e.g., wherein a graft from another organism e.g., human graft, such as a patient-derived tumor, is engrafted into immunodeficient mice) or and tumor graft animal model (e.g., wherein a tumor, from any source, is engrafted into the animal). The murine animal can also be a model in which the disease spontaneously occurs or wherein a tumor is induced by a carcinogen (for further details see e.g., www.emice(dot)nci(dot)nih(dot)gov/aam/mouse/carcinogen-induced-and-spontaneous-mouse-models).

As used herein the phrase "determining the efficiency" refers to monitoring disease progression using the antibody of the invention as compared to disease progression without the use of the antibody.

For example, when the disease is a tumor or metastasizing tumor, efficiency of treatment is determined when a reduction of about 10%, about 20%, about 30%, about 40%, about 50%, about 60%, about 70%, about 80%, about 90% or about 100% is observed in tumor size, in the number of metastatic lesions (e.g., one lesion), and/or in the number of areas of metastatic lesions (e.g., in the bone, brain, liver, lymph nodes, etc) as compared to disease progression without the use of the antibody.

For example, when the disease is a fibrosis, efficiency of treatment is determined when a reduction of about 10%, about 20%, about 30%, about 40%, about 50%, about 60%, about 70%, about 80%, about 90% or about 100% is observed in excess connective tissue (in an organ or tissue) as compared to excess connective tissue without the use of the antibody.

In order to determine the efficiency of the antibody or antibody fragment of some embodiments of the invention, the antibody is administered to the animal (e.g., at different doses and intervals) and disease progression is monitored using any method known in the art, for example, by surgery (e.g., dissecting the animal after a predetermined time), by ultrasound, CT, PET, MRI, by blood test, etc.

Alternatively, a biological sample may be obtained from the animal and analyzed for disease parameters (e.g., for expression levels of liver peptides, pulmonary peptides, renal peptides, pancreatic peptides, tumor peptides, etc.).

A biological sample may refer to a sample of tissue or fluid isolated from a subject, including but not limited to, cells (e.g., liver cells, pulmonary cells, renal cells, etc.), tissues, organs, various tumors (e.g., tumor biopsy sample) and fluids such as blood, serum, plasma, lymph, bile fluid, urine, saliva, sputum, synovial fluid, semen, tears, cerebrospinal fluid, bronchioalveolar large fluid, ascites fluid, pus, conditioned medium, and also samples of in vivo cell culture constituents.

It will be appreciated that the antibody of some embodiments of the present invention may be attached to a detectable moiety in order to enable detection (e.g., in vivo detection) of the antibody.

Various types of detectable or reporter moieties may be conjugated to the antibody of the invention. These include, but not are limited to, a radioactive isotope (such as $^{[125]}$ iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. *J Immunoassay* 20:151-83; Wisdom G B., 1994. *Methods Mol Biol.* 32:433-40; Ishikawa E. et al., 1983. *J Immunoassay* 4:209-327; Oellerich M., 1980. *J Clin Chem Clin Biochem.* 18:197-208; Schuurs A H. and van Weemen B K., 1980. *J Immunoassay* 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimer or tetramer form of the antibody).

Table 1A provides non-limiting examples of identifiable moieties which can be conjugated to the antibody of the invention.

TABLE 1A

| Identifiable Moiety | Amino Acid sequence (GenBank Accession No.) | Nucleic Acid sequence (GenBank Accession No.) |
| --- | --- | --- |
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin ligase tag | LHHILDAQKMVWNHR | |
| orange fluorescent protein | AAL33917 | AF435432 |
| Beta galactosidase | ACH42114 | EU626139 |
| Streptavidin | AAM49066 | AF283893 |

According to one embodiment, the antibody of some embodiments of the invention can be used for in vitro or ex vivo applications (e.g., for detection of QSOX1 levels in biological samples).

According to one embodiment, the antibody of the invention may be immobilized on a solid support (e.g., for formation of an immunocomplex between the antibody and QSOX1 proteins in ex vivo or in vitro settings). As used herein the phrase "solid support" refers to a non-aqueous matrix to which a reagent of interest (e.g., the antibody of this aspect of the present invention) can adhere. Examples of solid supports include, but are not limited to, solid supports formed partially or entirely of glass (e.g., controlled pore glass), polysaccharides (e.g., agarose), polyacrylamides, polystyrene, polyvinyl alcohol and silicones. In certain embodiments, depending on the context, the solid support can comprise the well of an assay plate; in others it is a purification column (e.g., an affinity chromatography column). This term also includes a discontinuous solid phase of discrete particles, such as those described in U.S. Pat. No. 4,275,149.

The agents described hereinabove may be included in a diagnostic kit/article of manufacture preferably along with appropriate instructions for use and labels indicating FDA approval for use in diagnosing and/or assessing efficiency of treatment of a laminin-associated disease.

According to another aspect of the present invention, there is provided a kit for detecting a level of QSOX1 in a biological sample.

Such a kit can include, for example, at least one container including at least one of the above described diagnostic agents (e.g., antibodies comprising an antigen recognition domain to QSOX1) and an imaging reagent packed in another container (e.g., enzymes, secondary antibodies, buffers, chromogenic substrates, fluorogenic material). The kit may also include appropriate buffers and preservatives for improving the shelf-life of the kit.

According to another aspect of the present invention, there is provided a kit for preventing or treating a laminin-associated disease or condition.

Such a kit can include, for example, at least one container including at least one of the above described antibodies comprising an antigen recognition domain to QSOX1 and an additional therapeutic agent packed in another container (e.g., chemotherapeutic agents, hormonal therapeutic agents, radiotherapeutic agents, anti-proliferative agents). According to another embodiment, the therapeutic agent (e.g., antibody comprising an antigen recognition domain to QSOX1) and the additional therapeutic agent are packed in the same container. The kit may also include appropriate buffers and preservatives for improving the shelf-life of the kit.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which, together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Plasmid Construction

HsQSOX1 and MmQSOX1 mutants were made by restriction-free cloning based on the published HsQSOX1 [Grossman I. et al. (2013) *J. Mol. Biol.* 425: 4366-4378] and MmQSOX1 [Alon A. et al. (2012) *Nature* 488: 414-418] expression plasmids. MmQSOX1$_{Trx}$ and MmQSOX1$_{Erv}$ span residues 36-275 and 289-550, respectively, of *Mus musculus* QSOX1. The RnQSOX1 construct was previously described [Gat Y. et al. (2014) *Protein Sci.* 23: 1102-1112]. The CpQSOX1 protein spans residues 34-547 of *Cavia porcellus* QSOX1. A synthetic gene (Genescript) codon-optimized for CpQSOX1 production in *E. coli* was cloned between the NdeI and BamHI sites of the pET-15b vector (Novagen). For production of biotinylated MmQSOX1$_{Trx}$ an AviTag [Kay B et al. (2009) *Methods Mol. Biol.* 498: 185-196] was added at the carboxy terminus.

QSOX1 Expression and Purification

Recombinant HsQSOX1 [Grossman I. et al. (2013), supra] and RnQSOX1 [Gat Y. et al. (2014), supra] were expressed and purified as described. MmQSOX1, MmQSOX1$_{Erv}$, and CpQSOX1 were prepared as for HsQSOX1. MmQSOX1$_{Trx}$ used for crystallization was produced in the BL21 (DE3) *E. coli* strain. Cells were grown in LB media to OD$_{600\ nm}$ 0.5 at 37° C. Isopropyl-1-thio-β-D-galactopyranoside (IPTG) was added to a final concentration of 0.5 mM, and the cultures were grown for a further 40 hours at 15° C. Cells were lysed in 20 mM Tris buffer, pH 8.5, 500 mM NaCl, 20 mM imidazole, sonicated, and centrifuged for 1 hour at 40,000×g. The supernatant was applied to a Ni-NTA column (GE healthcare), and protein was eluted in 20 mM Tris buffer, pH 8.5, 500 mM NaCl, and a gradient of imidazole (20 to 500 mM). Eluted protein was further purified by size exclusion chromatography on a Superdex 75 16/60 column in 10 mM Tris buffer, pH 8, 100 mM NaCl. Purified MmQSOX1$_{Trx}$ was concentrated to 12 mg/ml, and immediately before crystallization was mixed with thrombin (3 units/mg MmQSOX1$_{Trx}$). Biotinylated MmQSOX1$_{Trx}$ for yeast-surface display screening was co-expressed with an expression plasmid for biotin ligase. Upon induction of protein expression with 500 μM IPTG, biotin was added to the growth medium at a concentration of 50 μM, and the cultures were grown for a further 24 hours at 20° C. Purification of biotinylated MmQSOX1$_{Trx}$ was as for MmQSOX1$_{Trx}$. Biotinylation was verified by ELISA.

Oxygen Consumption Assays for Testing QSOX1 Enzymes Activity and Inhibition

Recombinant mammalian QSOX1 enzymes (100 nM) were assayed with 200 μM DTT and various MAb492.1 concentrations in a Clarke-type oxygen electrode (Hansatech Instruments) as previously described [Grossman I. et al. (2013), supra]. Reactions were initiated by DTT injection, and oxygen consumption rates were obtained from initial slopes. For testing inhibition of MmQSOX1 and HsQSOX1 mutants by MAb492.1 and MAb316.1, respectively, 50 nM enzyme was assayed with 200 μM DTT, with and without 250 nM antibody. Measurements were performed 3 times, and resulting rates were averaged. For each mutant, the rate in the presence of inhibitory antibody was divided by the rate in the absence of antibody to get percent activity.

Generation and Selection of MAb316.1

Hybridomas were generated, and supernatants of approximately 1000 clones were screened for MmQSOX1 binding as previously described [Ilani T. et al. (2013) *Science* 341: 74-76]. Twenty top binders were tested for MmQSOX1 inhibition in the in vitro oxygen consumption assay, in which hybridoma supernatants were mixed with 100 nM MmQSOX1 and 200 μm DTT. Two inhibitory clones in addition to three strong binders were chosen for sub-cloning. Each of the sub-clones was tested for binding by ELISA. Approximately 40 sub-clones were chosen for inhibition assays. Supernatants of sub-clones 316.1 and 947.3 inhibited MmQSOX1 activity repeatedly, and so were chosen for further studies. MAb316.1 used for inhibition assays was produced in a miniPERM bioreactor (Sarstedt) in serum-free medium (DCCM) and was purified as previously described [Ilani T. et al. (2013), supra]. Variable region sequencing of both monoclonal antibodies was performed as previously described [Grossman I. et al. (2013), supra]. Briefly, the variable region was reverse transcribed from hybridomal mRNA and amplified by PCR using sets of degenerate primers [described in Benhar I. and Reiter Y. (2002) In *Curr. Protoc. Immunol*. Chapter 10: Unit 10.19B; and Zhou, H. et al. (1994) *Nucleic Acids Res.* 22: 888-889]. Amplified fragments of the heavy chain and light chain were then cloned into the pGEM-T Easy vector, sequenced, and analyzed in the ImMunoGeneTics database [Lefranc M. P. et al. (2005) *Nucleic Acids Res.* 33: 593-597]. A productively rearranged sequence was confirmed for each fragment and verified on the protein level by liquid chromatography-tandem mass spectrometry of purified MAb316.1 (Table 2, below).

Screening of scFv492.1 Mutants with Yeast-Surface Display

The scFv492.1 construct, without the His-tag and thrombin cleavage site [Grossman I. et al. (2013), supra], was cloned between the NdeI and BamHI sites in the yeast display plasmid pETCON [Fleishman S. J. et al. (2011) *Science* 332: 816-821]. Mutants of scFv492.1 were prepared on the basis of this plasmid by in vivo recombination in EBY 100 yeast using the LiAc method. Yeast growth and induction of scFv expression were carried out as previously described [Chao G. et al. (2006) *Nat. Protoc.* 1: 755-768], except that for induction 10 g raffinose per liter were added to the media and the cultures were grown for 16 hours at 20° C. Yeast were labeled with anti-cMyc (Santa Cruz Biotechnology) at a dilution 1:50 to monitor scFv expression, and with biotinylated MmQSOX1$_{Trx}$ (for concentrations see Table 3, below) for 45 minutes. After washing, secondary labeling was performed with streptavidin-allophycocyanin (streptavidin-APC) from Jackson Immunoresearch Laboratories, Inc. at a 1:50 dilution and with goat anti-mouse IgG1 secondary antibody Alexa fluor 488 conjugate (Life technologies) at a 1:100 dilution, for the anti-cMyc labeling. Alternatively, in the first rounds of screening (Table 3, below), yeast were labeled with anti-cMyc, washed, and then labeled with goat anti-mouse IgG1 secondary antibody Alexa fluor 488 conjugate and with biotinylated MmQSOX1$_{Trx}$ pre-loaded with streptavidin-APC in a 1:4 molar ratio [Chao G. et al. (2006), supra]. Display of scFv clones and MmQSOX1$_{Trx}$ binding was monitored by Alexa 488 and APC fluorescence, respectively, using an Accuri C6 flow cytometer. Anti-fluorescein scFv (PDB code: 1X9Q) was used as a positive control for scFv display. Yeast displaying scFv492.1 labeled with biotinylated HsQSOX1$_{Trx}$ were used as a positive control for binding.

Small scFv libraries were constructed by fully randomizing specific residue positions (Table 3, below) using the NNS codon. Oligonucleotides with NNS codons in desired positions and wild-type flanking regions were ordered from Sigma. NdeI and BamHI sites were deleted from the N- and C-termini of the scFv construct in the pETCON plasmid and inserted flanking the desired region for randomization. The plasmid was restricted, and the oligonucleotide pool was inserted through in vivo recombination using the LiAc method. In all libraries constructed, the number of colonies obtained was at least an order of magnitude larger than the potential size of the library ($20^{number\ of\ randomized\ positions}$). Libraries were induced and labeled as described above. Cells were sorted using a FACSAria III Cell Sorter in 3 iterative rounds of enrichment. In the first sorting round, the top 5% cells found within the green and red fluorescence area were collected into growth media. In the following sorting rounds, the top 1-4% cells were collected. Plasmids from the last cycle of FACS enrichment were sequenced. Eighteen colonies enriched from the library constructed in CDR H3 were sequenced, yielding two distinct sequences. Each of the two sequences was tested separately for MmQSOX1$_{Trx}$ binding, and the better binder (Table 3, below) was chosen for further study. Enrichment of the library constructed in L1 yielded a single clone, verified by sequencing 12 colonies. Enrichment of the library constructed in L2 yielded eight clones, which were tested for MmQSOX1$_{Trx}$ binding separately. The enriched L1 sequence was incorporated to the top binder. After verifying that the combined clone showed increased MmQSOX1$_{Trx}$ binding compared to the clones enriched directly from the L1 and L2 libraries, this clone was subjected to epPCR on the entire scFv sequence using the Agilent GeneMorph II Random Mutagenesis kit. Recombination in vivo was performed by electroporation, yielding a library of size 5*10$^7$. The library was subjected to 3 rounds of selection as described above, recovering scFv492gen.

Recombinant MAb492gen Production

The light chain and heavy chain variable regions of scFv492gen were amplified and cloned separately into mammalian expression vectors for human IgG1 antibodies [Tiller T. et al. (2008) *J. Immunol. Methods* 329: 112-124].

MAb492gen was expressed by transient co-transfection of the two plasmids in human embryonic kidney (HEK) 293T cells using polyethylenimine. Cell supernatants were collected and replaced with fresh medium every 4 days. Expression and secretion to the medium was verified by western blot. MAb492gen was purified from the media using protein G [Ilani T. et al. (2013), supra]. Purified MAb492gen with human constant regions was used for inhibition assays.

Inhibitory Constant Determination

Colorimetric assays of RNase A oxidation were performed as described previously to obtain IC$_{50}$ values [Grossman I. et al. (2013), supra]. K$_i$ values were obtained in oxygen consumption assays as previously described [Grossman I. et al. (2013), supra].

Laminin Staining and Cell Adhesion Assay

The assays were conducted essentially as previously described [Ilani T. et al. (2013), supra]. Instead of human fibroblasts, mouse fibroblasts were grown for three days in the presence of various antibodies. HEK 293T cells were used as adhering cells.

Analytical Size-Exclusion Chromatography

MsQSOX1, its fragments, MAb316.1, or MAb947.3 were loaded onto a Superdex 200 column (GE HealthCare) equilibrated with phosphate buffered saline (PBS) at a flow rate of 0.8 mL/min. MsQSOX1-antibody complexes were injected after a 30 min co-incubation at 4° C. Elution of proteins was monitored by absorbance at 280 nm.

Fab-MmQSOX1$_{Trx}$ Complex Formation

MAb492.1 light chain and heavy chain were amplified from hybridomal cDNA [Grossman I. et al. (2013), supra] and cloned into the MAb492gen expression vectors, separately. Variable regions of scFv492gen were amplified and cloned into these vectors instead of the 492.1 variable regions. A stop codon was inserted after the CH1 segment of the heavy chain, to obtain a coding sequence for a Fab fragment. Fab492gen was expressed and purified as was MAb492gen. The heavy and light variable regions of MAb316.1 were amplified from hybridomal cDNA and cloned separately into the above mentioned MAb492gen expression vectors. MAb316.1 was expressed and purified as for MAb492gen. Fab316.1 was prepared by papain digestion as previously described [Grossman I. et al. (2013), supra]. Purified Fab492gen or Fab316.1 was mixed with purified MmQSOX1$_{Trx}$ at a 1:2 ratio for 30 minutes at 4° C. to form complexes, which were purified from excess MmQSOX1$_{Trx}$ by size-exclusion chromatography. Prior to crystallization the complexes were concentrated to 10 mg/ml.

Protein Crystallization

Crystals were grown by hanging-drop vapor diffusion at 293 K. MmQSOX1$_{Trx}$ crystals used for seeding were grown over a well solution containing 0.2 M ammonium sulfate, 0.1 M sodium acetate, pH 4.6, 21% w/v polyethylene glycol (PEG) 4 kD. These crystals were crushed and seeded into drops of MmQSOX1$_{Trx}$ grown over a well solution containing 5% w/v dimethyl sulfoxide, 0.1 M sodium acetate, pH 4.6, 7% w/v PEG monomethyl ether 2 kD. Crystals were transferred to a solution containing 0.1 M sodium acetate, pH 4.6, 15% w/v PEG monomethyl ether 2 kD, 25% glycerol and flash frozen in a nitrogen stream at 100 K. Crystals of the MmQSOX1$_{Trx}$-Fab316.1 complex were grown over a well solution containing 50 mM ammonium sulfate, 0.1 M bis-tris methane buffer, pH 5.5, 22% w/v PEG 3.35 kD. Crystals were transferred to a solution with the same content and 25% w/v glycerol for freezing. Crystals of the MmQSOX1$_{Trx}$-Fab492gen complex were grown over a well solution containing 50 mM $CaCl_2$, 0.1 M 2-(N-morpholino)ethanesulfonic acid buffer, pH 6, 22.5% w/v PEG 6 kD, and were transferred to the same solution containing 25% w/v glycerol prior to freezing.

Data Collection

Diffraction data for MmQSOX1$_{Trx}$, MmQSOX1$_{Trx}$-Fab316.1 complex, and MmQSOX1$_{Trx}$-Fab492gen complex were collected at 100 K on a RU-H3R generator (Rigaku) equipped with a RaxisIV++ image plate system and Osmic mirrors. For MmQSOX1$_{Trx}$, data were collected to 2.05 Å resolution from a crystal of space group P2$_1$. MmQSOX1$_{Trx}$-Fab316.1 complex data were collected to 2.2 Å resolution from a crystal of space group P2$_1$2$_1$2$_1$. Diffraction data for MmQSOX1$_{Trx}$-Fab492gen were collected to 2.3 Å resolution from a crystal of space group P2$_1$. All data sets were processed and scaled using DENZO and SCALEPACK [Broennimann Ch. et al. (2006) *J. Synchrotron Radiat.* 13: 120-130].

Structure Solution

All three structures were determined by molecular replacement using Phaser [McCoy A. J. et al. (2007) *J. Appl. Crystallogr.* 40: 658-674]. The HsQSOX1$_{Trx}$ structure (PDB code: 3Q6O) was used as a search model for MmQSOX1$_{Trx}$, and model rebuilding and mutagenesis was done in Coot [Emsley P. and Cowtan K. (2004) *Acta Crystallogr. D. Biol. Crystallogr.* 60: 2126-2132]. The resulting MmQSOX1$_{Trx}$ structure (PDB code: 5D8I) was used as a search model for both MmQSOX1$_{Trx}$-Fab complexes. After translation and rotation functions were found for MmQSOX1$_{Trx}$, a search for the constant region of Fab316.1 was performed using an identical constant region (PDB code: 3D85, chain A spanning residues 108-213 and chain B spanning residues 116-217). The variable region of Fab316.1 heavy chain was searched with a model having 87% identity (PDB code: 4Q0X, chain H spanning residues 1-118 without CDR H3), and the light chain variable region was searched with a 94% identical model (PDB code: 3AB0, chain C spanning residues 1-106). For Fab492gen, three search models from Fab492.1 (PDB code: 4IJ3, chains B and C) were used: the constant region, the light chain variable region without the mutated residues in Fab492gen, and the heavy chain variable region without CDRs H1 and H3. For both complexes addition of CDR loops and model rebuilding were done using Coot [Emsley P. and Cowtan K. (2004), supra]. Refinement was performed using Phenix [Afonine P. V. et al. (2005) *CCP4 Newsletter* 42, contribution 8]. Validation was done using MolProbity [Lovell S. C. et al. (2003) *Proteins* 50, 437-450], according to which there are no Ramachandran outliers in the structures reported herein.

Treatment Regime in Marine 4T1 Breast Cancer Model

4T1 mCherry cells were suspended in Hanks' Balanced Salt Solution at a concentration of 2.5×10$^6$ cells/ml and mixed 1:1 with Cultrex® Basement Membrane Extract. 250,000 cells were injected into the mammary fat pad of 45 BALB/c female mice. Animals were divided into 5 groups containing 9 animals each (as depicted in Table 1B, below). Treatments were administered by intraperitoneal injection, beginning 3 days after cell injection. Tumor dimensions (x,y,z) were measured with a caliper twice a week. Tumor volumes were calculated according to: x*y*z*6/π. Animals were weighed once a week. Twenty days post cell injection all animals were sacrificed by $CO_2$ asphyxiation. Tumors and lungs were removed into 4% formaldehyde solution and prepared for histology.

TABLE 1B

Treatment regime in murine 4T1 breast cancer model

| Group | Treatment | Frequency of administration | Vehicle |
|---|---|---|---|
| 1 | 50 mg/kg control IgG antibody | twice a week | PBS |
| 2 | 30 mg/kg MAb316.1 | twice a week | PBS |
| 3 | 8 mg/kg doxorubicin | once a week | PBS |
| 4 | 8 mg/kg doxorubicin | once a week | PBS |
|   | 30 mg/kg MAb316.1 | twice a week |   |
| 5 | 8 mg/kg doxorubicin | once a week | PBS |
|   | 15 mg/kg MAb316.1 | twice a week |   |

Example 1

The QSOX1 Inhibitor MAb492.1 is Species-Specific

MAb492.1, which inhibits HsQSOX1 activity in vitro and in cell culture at a near-stoichiometric concentration [Grossman I. et al. (2013) supra], was tested on other mammalian QSOX1 enzymes to find a suitable model for assessing QSOX1 inhibition in vivo. Three mammalian QSOX1 enzymes, from common experimental organisms and having 78-79% sequence identity with HsQSOX1, were chosen: *Mus musculus* QSOX1 (MmQSOX1), *Rattus norvegicus* QSOX1 (RnQSOX1), and *Cavia porcellus* (CpQSOX1). Enzyme activity was assessed in an oxygen consumption assay on the model substrate dithiothreitol (DTT). According to the assay, MAb492.1 had no effect on MmQSOX1, RnQSOX1, or CpQSOX1, even at 1 μM, a 10:1 molar ratio of antibody to enzyme (FIG. 2A).

To understand the molecular basis for MAb492.1 species restriction, the epitope on HsQSOX1 was compared with the corresponding regions of RnQSOX1, CpQSOX1, and particularly MmQSOX1 by crystallizing and solving the structure of the Trx module of MmQSOX1 (MmQSOX1$_{Trx}$) to 2.05 Å resolution (Table 1C, below). Two MmQSOX1$_{Trx}$ molecules were present in the crystal asymmetric unit. The atomic coordinates of these two molecules were overlaid on the previously solved structure of a complex between HsQSOX1$_{Trx}$ and a Fab fragment of MAb492.1 (Fab492.1) [Grossman I. et al. (2013) supra]. Although the regions near the CXXC redox-active site are identical in sequence among QSOX1 orthologs, a few other positions of contact between Fab492.1 and HsQSOX1 differ (FIG. 2B). In particular, HsQSOX1 P116, which fits well into a cleft between hydrophobic complementary determining regions (CDRs) L3, H2, and H3 of Fab492.1, is replaced with alanine in other mammalian QSOX1 enzymes. The MmQSOX1$_{Trx}$ structure showed that this alanine residue cannot fill the hydrophobic cleft in a hypothetical complex between MmQSOX1 and Fab492.1. Moreover, the replacement of proline by alanine affects the position of the backbone nearby, such that a clash would form between MmQSOX1 N117 and CDR L3 (FIG. 2C, left). Another region that is not conserved among the QSOX1 enzymes examined is VFPV(135-138) from HsQSOX1. The corresponding TLPG(138-141) loop in one of the MmQSOX1 molecules is displaced from the antibody CDRs L1 and L2 and is found closer to CDR H3 than the VFPV(135-138) loop of HsQSOX1 (FIG. 2C, right). As a result, MAb492.1 CDR H3 would clash sterically with this loop, eliminating potential interactions of MmQSOX1 with CDRs L1 and L2.

TABLE 1C

Summary of crystallographic data collection and refinement statistics

| | MmQSOX1$_{Trx}$ | Fab492gen-MmQSOX1$_{Trx}$ complex | Fab316.1-MmQSOX1$_{Trx}$ complex |
|---|---|---|---|
| *Date collection* | | | |
| Space group | P2$_1$ | P2$_1$ | P2$_1$2$_1$2$_1$ |
| *Cell dimensions* | | | |
| a, b, c (Å) | 42.5, 116.4, 50.0 | 78.8, 204.8, 44.7 | 65.5, 112.7, 193.4 |
| α, β, γ (°) | 90, 103, 90 | 90, 90, 90 | 90, 90, 90 |
| Copies in asymmetric unit | 2 | 2 | 2 |
| Resolution (Å) | 50-2.05 (2.05-2.09) | 50-2.30 (2.30-2.34) | 50-2.20 (2.20-2.24) |
| Measured reflections | 104,982 | 190,891 | 358,728 |
| Unique reflections | 28,528 (1197) | 62,461 (3167) | 72,630 (3564) |
| Completeness (%) | 95.8 (79.2) | 99.7 (100) | 98.9 (98.8) |
| Redundancy | 3.7 (2.9) | 3.1 (3.0) | 4.9 (3.8) |
| <I/σI> | 11.3 (2.2) | 8.3 (2.2) | 7.6 (2.0) |
| R$_{sym}$ | 0.063 (0.318) | 0.084 (0.418) | 0.088 (0.408) |
| *Refinement* | | | |
| Resolution (Å) | 28.5-2.05 | 27.4-2.3 | 23.2-2.2 |
| Number of reflections in working set | 28,485 | 62,422 | 72,573 |
| Number of reflections in test set | 1957 | 2002 | 3588 |
| R$_{work}$/R$_{free}$ | 0.201/0.252 | 0.167/0.228 | 0.174/0.236 |
| Number of protein atoms | 3774 | 10180 | 10156 |
| Number of water molecules | 288 | 425 | 751 |
| Mean B-factor | 31.50 | 34.98 | 32.65 |
| *Root mean square deviations* | | | |
| Bond length (Å) | 0.006 | 0.004 | 0.008 |
| Bond angle (°) | 1.275 | 1.013 | 1.113 |
| *Ramachandran plot* | | | |
| Favored regions (%) | 96.0 | 98.1 | 96.6 |
| Additional allowed regions (%) | 4.0 | 1.9 | 3.4 |
| Disallowed regions (%) | 0 | 0 | 0 |

Values in parentheses are for the highest-resolution shell.

To confirm that the structural differences noted between HsQSOX1 and MmQSOX1 are the cause of MAb492.1 species specificity, three MmQSOX1 mutants that mimic HsQSOX1 in distinct positions were constructed. MAb492.1 inhibition was tested on these mutants to identify the residues that interfere with MAb492.1-MmQSOX1 complex formation. The first mutant, A116P, was inhibited by about 60% (FIG. 2D), and the second mutant, TLPG(138-141)VFPV, by about 50%. The third mutant, which comprises both the above mutations, was inhibited by MAb492.1 to the same extent as HsQSOX1 (100%), confirming the identity of residues that determine the specificity of MAb492.1 towards HsQSOX1.

Example 2

Generation and Characterization of a Murine Antibody Inhibitor Targeting MmQSOX1

The species-specificity exhibited by MAb492.1 is a common feature shared by natural monoclonal antibodies. Although differences in antigen structure might be small among orthologs, they are exploited by the immune system to bind the foreign antigen and avoid self-reactivity. In the large antigen surface area buried by antibodies, minor differences between orthologs can cause steric clashes that cannot be remedied by a simple corresponding change in the antibody. QSOX1 knock-out (QSOX1-KO) mice produced in the laboratory were then exploited to generate surrogate antibodies against MmQSOX1, which is a foreign antigen for these animals. Hybridoma supernatants were screened for binding of MmQSOX1 using a standard enzyme-linked immunosorbent assay (ELISA). Top binders were tested for MmQSOX1 inhibition, and five were chosen for sub-cloning (described in the materials and experimental procedures section above). Antibody sub-clones derived from one particular clone inhibited MmQSOX1, and one sub-clone, designated MAb316.1 and classified to be of the IgG1 isotype, was selected for further study. The sequences of the MAb316.1 variable regions (described in the materials and experimental procedures section above) are presented in Table 2, below.

TABLE 2

MAb316.1 variable region amino acid sequences

| Chain | Sequence |
|---|---|
| light | QWLTQSPAIMSASPGEKVTISCSASSSVSYMYWYHQKPGSSPKPWIYRTSNLASGVPARFSG SGSGTSYSLTISSMEAEDAATYYCQQYHSYPLTFGAGTKLELK (SEQ ID NO: 9) |

TABLE 2-continued

MAb316.1 variable region amino acid sequences heavy QVQLQQSGPELVKPGASVKISCKASGYSFTSYYIHWVKQRPGQGLEWIGWIYPGSYNTEYSEK
FKGKATLTADTSSSTAYMQLSSLTSEDSAVYYCARSEDWFAYWGQGTLVTVS (SEQ ID NO: 10)

|  | MW (calc) | MW (exp) | peptide | enzyme |
|---|---|---|---|---|
| light | 1855.9729 | 1855.9713 | QIVLTQSPAIMSASPGEK (SEQ ID NO: 11) | trypsin |
|  | 2936.3419 | 2936.3473 | VTISCSASSSVSYMYWYHKPGSSPK (SEQ ID NO: 12) |  |
|  | 1071.5671 | 1071.5673 | TSNLASGVPAR (SEQ ID NO: 13) |  |
|  | 3389.4864 | 3389.4856 | TISSMEAEDAATYYCQQYHSYPLTFGAGTK (SEQ ID NO: 14) |  |
|  | 1650.8829 | 1650.8842 | IYRTSNLASGVPARF (SEQ ID NO: 15) | chymotrypsin/ Asp-N |
|  | 1374.7352 | 1374.7368 | RTSNLASGVPARF (SEQ ID NO: 16) |  |
|  | 1586.7319 | 1586.7325 | ASGVPARFSGSGSGTSY (SEQ ID NO: 17) |  |
|  | 793.4351 | 793.4334 | TFGAGTKLEL (SEQ ID NO: 18) |  |
| heavy | 1992.0977 | 1992.1004 | QVQLQQSGPELVKPGASVK (SEQ ID NO: 19) | trypsin |
|  | 1807.8521 | 1807.8570 | ASGYSFTSYYIHWVK (SEQ ID NO: 20) |  |
|  | 2957.3959 | 2957.3984 | QRPGQGLEWIGWIYPGSYNTEYSEK (SEQ ID NO: 21) |  |
|  | 2079.9242 | 2079.9241 | MQLSSLTSEDSAVYYCAR (SEQ ID NO: 22) |  |
|  | 2390.2278 | 2390.2264 | QQSGPELVKPGASVKISCKASGY (SEQ ID NO: 23) | chymotrypsin/ Asp-N |
|  | 1652.8761 | 1652.8787 | VKQRPGQGLEWIGW (SEQ ID NO: 24) |  |
|  | 1420.6153 | 1420.6147 | PGSYNTEYSEKF (SEQ ID NO: 25) |  |

The table displays representative peptides detected by lipid chromatography-tandem mass spectrometry.

Example 3

Generation of a MAb492.1 Variant Targeting MmQSOX1

In parallel to obtaining an antibody targeting MmQSOX1$_{Trx}$ from hybridoma clones, a variant of MAb492.1 that inhibits MmQSOX1 was developed. Though occasionally a single point mutation may modulate antibody species specificity to some extent, substantial re-engineering is often required to obtain the desired target-recognition properties. According to the observation that mutating four residues of MmQSOX1 was sufficient to achieve inhibition by MAb492.1 (FIG. 2D), inventors reasoned that inhibiting MmQSOX1 would be possible by making a set of mutations in the MAb492.1 CDRs or surrounding regions. However, in contrast to modifying MmQSOX1 to mimic HsQSOX1, modification of the antibody had to be made without a guiding structure. Furthermore, the four QSOX1 residues controlling reactivity with MAb492.1 affected the position of the QSOX1 polypeptide backbone (FIG. 2C), hinting that substantial compensating mutations affecting CDR loop position and/or structure would be needed to convert MAb492.1 into a cross-reactive reagent. Candidate residues for mutation to improve MmQSOX1$_{Trx}$ binding were identified based on the structures of MmQSOX1$_{Trx}$ and the Fab492.1-HsQSOX1$_{Trx}$ complex (Table 3, below). Specific point mutations were tested and small libraries were constructed, varying up to four CDR residues in specific locations, from which binding mutants were enriched. This careful approach was taken to increase the likelihood of gaining functionality against MmQSOX1 without losing binding to the targeted epitope.

Screening was performed using yeast-surface display of single-chain variable fragments (scFv) (described in the materials and experimental procedures section above) [Chao G. et al. (2006) Nat. Protoc. 1: 755-768]. A scFv variant of MAb492.1 (scFv492.1) had been constructed, expressed in E. coli, and shown to inhibit HsQSOX1 successfully [Grossman I. et al. (2013), supra], laying the groundwork for using yeast-surface display to select for MmQSOX1 inhibitors. A scFv variant carrying ten mutations in the CDRs achieved by specific rational mutations and consecutive rounds of library sorting and enrichment (Table 3, below) bound MmQSOX1$_{Trx}$ on the surface of yeast (FIG. 3A). Since mutations in other CDR residues did not improve MmQSOX1$_{Trx}$ binding further, one round of affinity maturation was performed on the scFv492.1 mutant for fine-tuning. To this end a gene library (total size of 5*10$^7$ clones) was constructed by error-prone polymerase chain reaction (epPCR), with an average of three mutations per gene, and subjected the library to three rounds of flow-cytometry selection for MmQSOX1$_{Trx}$ binding. A mutant with a total of 12 mutations on scFv492.1, designated scFv492gen (FIG. 3J), was isolated and characterized, yielding an apparent K$_d$ of 65 nM on the surface of yeast (FIGS. 3K-L). Based on the scFv492gen sequence, a recombinant full-length antibody, MAb492gen, was produced in mammalian cells.

TABLE 3

MAb492.1 residues mutated to generate MAb492gen

| Template name | Template for mutations | Residue[a] | Mutation | Strategy | MmQSOX1$_{Trx}$ concentration used for binding tests | Positive mutations[b] |
|---|---|---|---|---|---|---|
| wt | scFv492.1 | Y92 (light chain) | N/D | 25 of the possible combinatorial mutants involving these three residues were tested | 500 nM pre-loaded with streptavidin-APC | S93A |
|  |  | S93 (light chain) | G/A |  |  |  |
|  |  | Y100 (heavy chain) | D/N/G/S |  |  |  |

TABLE 3-continued

MAb492.1 residues mutated to generate MAb492gen

| Template name | Template for mutations | Residue[a] | Mutation | Strategy | MmQSOX1$_{Trx}$ concentration used for binding tests | Positive mutations[b] |
|---|---|---|---|---|---|---|
| a | scFv492.1 S93A | Y99-S102 (heavy chain) | All possible amino acids | Library in potential size of $20^4$ clones subjected to three rounds of selection | 250 nM pre-loaded with streptavidin-APC | Y99S Y100K G101D S102P |
| b | scFv492.1 S93A Y99S Y100K G101D S102P | Y92-P95 (light chain) T30-Y32 (heavy chain) W52-D54, R56 (heavy chain) D58 (heavy chain) | All possible amino acids All possible amino acids All possible amino acids E/Q | Library in potential size of $20^4$ clones subjected to three rounds of selection Library in potential size of $20^3$ clones subjected to three rounds of selection Library in potential size of $20^4$ clones subjected to three rounds of selection Tested point mutations for MmQSOX1$_{Trx}$ binding | 250 nM pre-loaded with streptavidin-APC 250 nM pre-loaded with streptavidin-APC 250 nM pre-loaded with streptavidin-APC 250 nM pre-loaded with streptavidin-APC | — — — D58E |
| c | scFv492.1 S93A Y99S Y100K G101D S102P D58E | S30-T31 (light chain) H49-S50, Y52 (light chain) | All possible amino acids All possible amino acids | Library in potential size of $20^2$ clones subjected to three rounds of selection Library in potential size of $20^3$ clones subjected to three rounds of selection | 250 nM pre-loaded with streptavidin-APC 250 nM pre-loaded with streptavidin-APC | T31G H49S S50M Y52Q |
| d | scFv492.1 S93A Y99S Y100K G101D S102P D58E T31G H49S S50M Y52Q | All | All | Library was created by epPCR and its size was evaluated as $5*10^7$ clones. Library was subjected to three rounds of selection | 250 nM (not pre-loaded) | G33S N35I S100M (heavy chain) |

[a]Numbering is according to structure of HsQSOX1$_{Trx}$-Fab492.1 complex (PDB code: 4IJ3).
[b]Mutations that improved MmQSOX1$_{Trx}$ binding.

Example 4

Comparison of Inhibition Constants

MmQSOX1 inhibition by MAb492gen was next quantified and compared to inhibition by the natural antibody MAb316.1. In one assay, MmQSOX1 activity was measured by the number of free thiols remaining at the end of the oxidation reaction of denatured and reduced RNase A. Various MAb492gen concentrations were scanned against two MmQSOX1 concentrations. In both cases the IC$_{50}$ values were similar to the MmQSOX1 concentration used in the assay (FIG. 3B), indicating tight-binding inhibition. In a second assay MmQSOX1 catalytic activity on DTT was measured using the oxygen consumption assay, providing data that were fitted to a model of tight-binding inhibition [Bieth, J. G. (1995) *Methods Enzymol.* 248: 59-84] to yield an inhibitory constant (K$_i$) of 2.2±0.5 nM (FIG. 3C and Table 4, below). Like MAb492gen, MAb316.1 exhibited tight-binding inhibition of MmQSOX1, but with a slightly larger K$_i$ value of 16±2 nM (FIG. 3D and Table 4, below).

TABLE 4

Inhibition constants for antibodies targeting QSOX1

| | enzyme | |
|---|---|---|
| Antibody | HsQSOX1 | MmQSOX1 |
| MAb492.1 | 0.9 ± 0.1 nM | No inhibition at 1 μM |
| MAb492gen | 1.6 ± 0.6 nM | 2.2 ± 0.5 nM |
| MAb316.1 | No inhibition at 1 μM | 16 ± 2 nM |

Example 5

Antibodies Inhibit MmQSOX1 Activity in Cell Culture

MmQSOX1 inhibition by MAb316.1 and MAb492gen was examined in cell culture using two readouts of QSOX1 activity [Ilani T. et al. (2013), supra]. QSOX1 and laminin are secreted from quiescent fibroblasts into the ECM, where QSOX1 promotes laminin incorporation, and consequently the adherence of epithelial cells to the fibroblast monolayer. Thus, intact laminin networks in the ECM and cell adherence indicate functional QSOX1 activity in the ECM [Ilani T. et al. (2013), supra]. Inventors first verified that MmQSOX1 is secreted from confluent mouse embryonic fibroblasts (MEFs) (FIG. 4A). Next, extracellular laminin secreted by MEFs grown for three days in the presence of MAb492.1, MAb316.1, or MAb492gen was stained. As in human fibroblast cultures [Ilani T. et al. (2013), supra], an extensive laminin network was observed only in ECM produced with active QSOX1 (FIGS. 3E-H and FIGS. 4B-I). A quantitative assay of epithelial cell adhesion to MEF monolayers was performed next. Fluorescently labeled epithelial cells were added to MEFs grown in the absence or presence of the antibodies, and adherent cells were quantified. As expected, more epithelial cells adhered to MEFs grown in the absence of inhibitory antibody compared to MEFs grown in the presence of either 250 nM or 1 μM antibody targeting MmQSOX1 (MAb316.1 and MAb492gen). MAb492.1, which inhibits HsQSOX1 but not MmQSOX1, did not affect the laminin network or epithelial cell adherence in the mouse fibroblast cultures (FIGS. 3E-I and FIGS. 4J-O).

Example 6

MAb492gen Binds MmQSOX1 Due to Alterations at the Interface of the Heavy and Light Chains After attaining a MAb492.1 mutant that inhibits MmQ-SOX1, X-ray crystallography was used to examine the structural effects of mutations that enabled antigen recognition. A complex between a Fab fragment of MAb492gen (Fab492gen) and MmQSOX1$_{Trx}$ was formed, and its structure was solved to 2.3 Å resolution (Table 1C). Two complexes were found in the asymmetric unit, deviating from one another mainly in the angle between the constant and the variable regions of the Fab fragment. As expected, the MAb492gen epitope on MmQSOX1 corresponds to the HsQSOX1 region bound by MAb492.1 (FIG. 5A). MmQSOX1$_{Trx}$ bound by MAb492gen takes the conformation of chain B from the unbound MmQSOX1$_{Trx}$, in which the TLPG(138-141) loop approaches the CXXC motif. MAb492gen differs from MAb492.1 primarily around this QSOX1$_{Trx}$ region (FIG. 5B). The complex structure revealed how a combination of relieving steric clashes and introducing new favorable interactions enabled recognition of MmQSOX1.

Based on the Fab492gen-MmQSOX$_{Trx}$ structure, inventors suspected that mutations introduced into CDR L3 and H3 prevented collisions between MmQSOX1 and the antibody. CDR H3 is the most variable CDR in sequence and structure among antibodies and is usually responsible for most of the paratope [Xu J. L. and Davis M. M. (2000) *Immunity* 13: 37-45]. The YYGS-to-SMDP mutation of CDR H3 in Fab492gen both eliminated a clashing tyrosine and caused a rearrangement of the backbone conformation (FIGS. 5B and 5F), resulting in the first significant improvement in binding. Changing the structure of the CDR H3 loop also allowed closer approach of CDR L2, together with the rest of the light chain, toward the heavy chain (FIG. 5B). This movement appears to have helped relieve the expected clash between CDR L3 and N117 in MmQSOX1 (FIG. 2C).

A second effect of the slight change in the relative orientations of the heavy and light chain variable regions observed in the Fab492gen-MmQSOX1$_{Trx}$ structure was the introduction of new interactions. Some interactions were generated between the heavy and light chains, and some with the target. Mutating H49 in CDR L2 to serine enabled an interaction with the new CDR H3 SMDP loop (FIG. 5C), potentially contributing to pre-organization of the paratope. Mutating T31 in CDR L1 to glycine enabled formation of hydrogen bonds between CDR L1 and the MmQSOX1 TLPG(138-141) loop that could not form between MAb492.1 and MmQSOX1 (FIGS. 5D and 5E).

Example 7

MAb316.1 Exhibits a New Inhibition Mode of QSOX1

MAb492.1 and MAb492gen bind the N-terminal QSOX1 Trx domain. Since MAb316.1 was generated in mice injected with full-length MmQSOX1, inventors sought to localize its epitope. Size exclusion chromatography was used to compare the elution profiles of MmQSOX1, or each of its constituent modules, to their elution profiles when mixed with MAb316.1. In size exclusion chromatography, this antibody shifted the elution of both full-length MmQSOX1 and the Trx module to higher apparent molecular weights (FIG. 6A). In contrast, migration of the MmQSOX1 Erv module, responsible for the sulfihydryl oxidase activity, was not affected, pointing at the Trx module as the MAb316.1 binding region in MmQSOX1.

To localize the MAb316.1 epitope to specific residues in MmQSOX1$_{Trx}$, a Fab fragment of MAb316.1 (Fab316.1) was co-crystallized with MmQSOX1$_{Trx}$ and the structure was solved to 2.2 Å resolution (see Table 1C, above). Two MmQSOX1$_{Trx}$-Fab316.1 complexes were present in the crystal asymmetric unit. The complex structure revealed a distinct QSOX1 inhibition mode from the one displayed by MAb492.1 and MAb492gen. Fab316.1 envelopes the helix containing the Trx redox-active site at its amino terminus but does not block access to the CXXC motif itself (FIG. 6B). It seems that a small substrate like DTT might be able to reduce the Trx active site even in the presence of MAb316.1. Nevertheless, MAb316.1 would physically prevent formation of the inter-domain electron-transfer intermediate of MmQSOX1 (FIG. 6C), thus interrupting a different step in the catalytic cycle than MAb492.1 and MAb492gen (transition from state 2 to 3, rather than 1 to 2 in FIG. 1C).

Example 8

MAb492gen is the Only QSOX1 Inhibitory Antibody Cross-Reactive with Mouse and Human Orthologs A QSOX1-targeting antibody with dual species specificity, i.e., that inhibits HsQSOX1 as well as MmQSOX1, would be a valuable tool that could be used in animal models, and in turn, with minimal engineering, in clinical trials. Inventors therefore tested for MAb492gen and MAb316.1 inhibition of HsQSOX1. MAb316.1 up to a concentration of 1 μM did not inhibit HsQSOX1 (FIG. 7A). In contrast, though no selection for binding of HsQSOX1 was performed during its development, MAb492gen retained tight-binding activity against HsQSOX1, having a $K_i$ value of 1.6±0.6 nM for HsQSOX1 (FIG. 7B and Table 4, above) compared to 0.9±0.1 nM previously measured for MAb492.1 [Grossman I. et al. (2013), supra].

A comparison of the three available QSOX1-antibody complex structures suggests features that prevent or contribute to target species specificity. Lack of binding of HsQSOX1$_{Trx}$ by MAb316.1 can be explained once again by the VFPV(135-138) loop, which was a major specificity determinant for MAb492.1. In the Fab316.1-MmQSOX1$_{Trx}$ complex, however, the corresponding TLPG(138-141) loop is not directly in the interface, but rather affects the position of the conserved downstream residues AGA(139-142). These downstream residues in HsQSOX1 are expected to clash sterically with CDR H2 of MAb316.1 (FIG. 7C). The constellation of aromatic residues (light chain: Y31, Y90, Y93; heavy chain: Y33, W50, Y52) that mediates interaction between Fab316.1 and MmQSOX1 presumably does not accommodate minor differences in backbone position between the mouse and human QSOX1 orthologs. Mutating HsQSOX1 to mimic MmQSOX1 by converting TLPG(138-141) to VFPV(138-141) made MAb316.1 inhibition of HsQSOX1 possible, confirming this region as the block to cross-reactivity (FIG. 7D).

As opposed to MAb316.1 and MAb492.1, MAb492gen accommodates both the TLPG(138-141) loop from MmQSOX1 and presumably the corresponding VFPV(135-138)

from HsQSOX1 between its H3, L1, and L2 CDRs, resulting in dual specificity (FIG. 5F). One key difference between MAb492gen and the species-specific antibodies (MAb492.1 and MAb316.1) is its lower content of tyrosines and other aromatic residues in the CDRs. Tyrosines are highly prevalent and effective in antibody CDRs, where they can make van der Waals, hydrogen bonding, and cation-π interactions. In MAb492gen, however, three tyrosines were replaced with more flexible residues. Another difference is the introduction of a charged residue, D101, into CDR H3, which becomes buried at the QSOX1-antibody interface. D101 forms water-mediated interactions with the MmQSOX1 TLPG (138-141) loop, while also hydrogen bonding to the light chain (FIG. 5C). The bulky aromatic residues within the corresponding YYGS sequence of MAb492.1 H3 were apparently unable to accommodate the deviation of MmQSOX1 TLPG(138-141) from HsQSOX1 VFPV(135-138). Though the structural variability of this QSOX1 loop likely positions backbone hydrogen bond donor and acceptor groups differently in space, the water network through which Asp101 interacts with its target in the Fab492gen-MmQSOX$_{Trx}$ complex suggests that MAb492gen can accommodate these differences through a re-organized water structure. Through features offering greater flexibility, MAb492gen acquired expanded capabilities, but it presumably retained its specificity towards QSOX1 antigens by maintaining CDRs that interact with the CXXC motif region (CDRs H1 and H2), the universal catalytic element in QSOX1 Trx domains.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Example 9

MAb316.1 is Therapeutic In Vivo in a Breast Cancer Murine Model

The ability of an antibody inhibiting MmQSOX1 to control tumor growth and metastasis was evaluated in vivo in the 4T1 murine mammary carcinoma breast cancer model previously described [Pulaski and Ostrand-Rosenberg (2001) Mouse 4T1 breast tumor model. *Curr. Protoc. Immunol.* Chapter 20, Unit 20.2.]. Mice were injected with 4T1 cells together with matrigel, which aided in formation of a localized tumor, and then divided into five groups (as described in Table 1B, above). Each group received a different treatment: 50 mg/kg control IgG antibody twice a week, 8 mg/kg doxorubicin (a common chemotherapeutic agent) once a week, 30 mg/kg MAb316.1 twice a week, a combination of 8 mg/kg doxorubicin and 30 mg/kg MAb316.1, or a combination of 8 mg/kg doxorubicin and 15 mg/kg MAb316.1. Tumor volumes were measured twice a week. Animals were sacrificed after 20 days, and their tumors and lungs were removed for evaluation.

During the entire experiment, mice treated with doxorubicin alone had smaller tumors than control mice, as previously reported [Gao et al. (2011) *J. Control Release* 152: 84-89]. Interestingly, treatment with the higher concentration of MAb316.1 used (30 mg/kg) reduced tumor volumes, and treatment with a combination of doxorubicin and 30 mg/kg MAb316.1 decreased tumor volumes compared to treatment with doxorubicin alone (FIG. 8). Treatment with the lower MAb316.1 concentration and doxorubicin resulted in tumors with a comparable size to tumors in the group treated with only doxorubicin. These results show that treatment with 30 mg/kg MAb316.1 twice a week slows the progression of an aggressive breast cancer in mice.

What is claimed is:

1. An antibody comprising an antigen recognition domain exhibiting species cross reactivity to human QSOX1 and murine QSOX1, said antigen recognition domain comprising complementarity determining regions (CDRs) as set forth in SEQ ID NOs: 46-51.

2. The antibody of claim 1, wherein said antibody is an antibody fragment, a single chain antibody or a monoclonal antibody.

3. The antibody of claim 2, wherein said monoclonal antibody is MAb492gen and comprises CDRs SEQ ID NOs: 46-51.

4. The antibody of claim 2, wherein said single chain antibody is scFV492gen and comprises CDRs SEQ ID NOs: 46-51.

* * * * *